(12) United States Patent
Jakobsen

(10) Patent No.: US 8,361,794 B2
(45) Date of Patent: Jan. 29, 2013

(54) CELLS EXPRESSING A MODIFIED T CELL RECEPTOR

(75) Inventor: Bent Karsten Jakobsen, Abingdon (GB)

(73) Assignee: Immunocore Limited, Oxon (GB)

( * ) Notice: Subject to any disclaimer, the term of this patent is extended or adjusted under 35 U.S.C. 154(b) by 966 days.

(21) Appl. No.: 11/597,252

(22) PCT Filed: Jun. 29, 2005

(86) PCT No.: PCT/GB2005/002570
§ 371 (c)(1),
(2), (4) Date: Apr. 28, 2009

(87) PCT Pub. No.: WO2006/000830
PCT Pub. Date: Jan. 5, 2006

(65) Prior Publication Data
US 2010/0047220 A1    Feb. 25, 2010

(30) Foreign Application Priority Data

Jun. 29, 2004 (GB) .................................. 0414499.4
Oct. 1, 2004 (GB) .................................. 0421831.9
Jun. 1, 2005 (GB) .................................. 0511123.2

(51) Int. Cl.
*C12N 5/0783* (2010.01)
*C12N 5/10* (2006.01)

(52) U.S. Cl. .................. 435/372.3; 424/93.71; 435/325; 435/361

(58) Field of Classification Search ................ 435/372.3, 435/325, 361; 424/93.71
See application file for complete search history.

(56) References Cited

U.S. PATENT DOCUMENTS 6,558,672 B1    5/2003    Pastan et al.

FOREIGN PATENT DOCUMENTS

| WO | WO 01/55366 A | 8/2001 |
| WO | WO 03/020763 A | 3/2003 |
| WO | WO 2004033685 A1 * | 4/2004 |
| WO | WO 2004/074322 A | 9/2004 |

OTHER PUBLICATIONS

Pecorari F et al: "Folding, heterodimeric association and specific peptide recognition of a murine alphabeta T-cell receptor expressed in *Escherichia coli*" Journal of Molecular Biology, London, GB, vol. 285, No. 4, Jan. 29, 1999, pp. 1831-1843, XP004457383, ISSN: 0022-2836.

Li Z G et al: "Structural Mutations in the Constant Region of the T-Cell Antigen Receptor (TCR) Beta Chain and Their Effect on TCR Alpha and Beta Chain Interaction" Immunology, Blackwell Publishing, Oxford, GB, vol. 88, No. 4, Aug. 1996, pp. 524-530, XP008028134, ISSN: 0019-2805.

Reiter Y et al: "Construction of a functional disulfide-stabilized TCR FV indicates that antibody and TCR FV frameworks are very similar in structure." Immunity, Cell Press, US, vol. 2, No. 3, Mar. 1995, pp. 281-287, XP009004075 ISSN: 1074-7613.

* cited by examiner

*Primary Examiner* — Taeyoon Kim
(74) *Attorney, Agent, or Firm* — Vedder Price. P.C.; Thomas J. Kowalski; Smitha B. Uthaman

(57) ABSTRACT

This invention provides a cell presenting at least one T cell receptor (TCR) anchored to the membrane by a transmembrane sequence, said TCR comprising an interchain disulfide bond between extracellular constant domain residues which is not present in native TCRs.

25 Claims, 27 Drawing Sheets

Figure 1
TCR α Chain
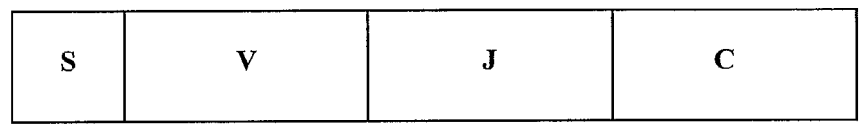
TCR β Chain
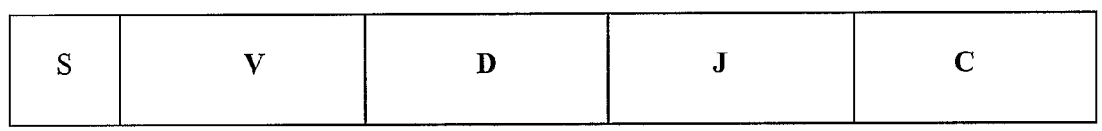

Figure 2
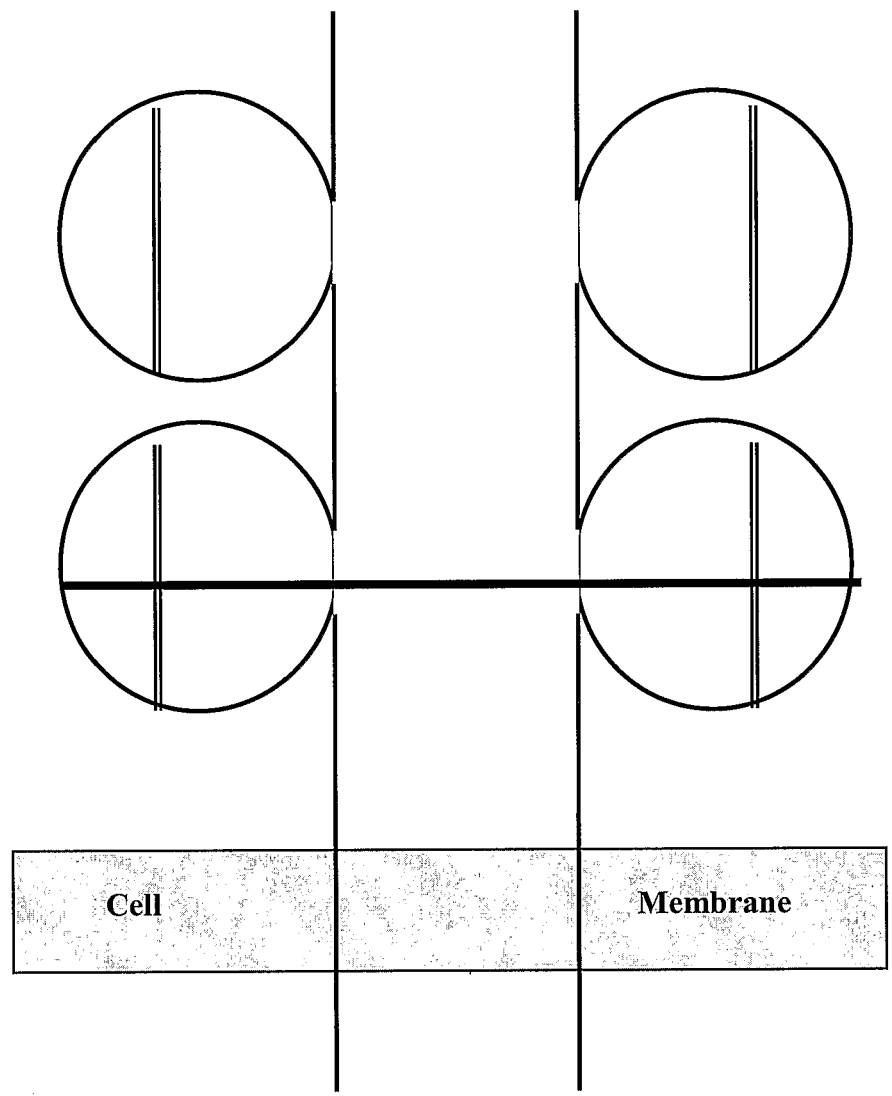
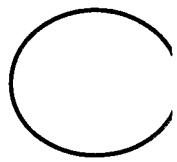 TCR domain === Native intra-chain disulfide bond
Non-native inter-chain disulfide bond

Figure 3a atgcagaaggaagtggagcagaactctggacccctcagtgttccagagggagccattg
cctctctcaactgcacttacagtgaccgaggttcccagtccttcttctggtacagaca
atattctgggaaaagccctgagttgataatgtccatatactccaatggtgacaaagaa
gatggaaggtttacagcacagctcaataaagccagccagtatgtttctctgctcatca
gagactccagcccagtgattcagccacctacctctgtgccgttacaactgacagctg
ggggaaattgcagtttggagcagggacccaggttgtggtcacccagatatccagaac
cctgaccctgccgtgtaccagctgagagactctaaatccagtgacaagtctgtctgcc
tattcaccgatttttgattctcaaacaaatgtgtcacaaagtaaggattctgatgtgta
tatcacagacaaatgtgtgctagacatgaggtctatggacttcaagagcaacagtgct
gtggcctggagcaacaaatctgactttgcatgtgcaaacgccttcaacaacagcatta
ttccagaagacaccttcttccccagcccagaaagttcctaa

Figure 3b atgaacgctggtgtcactcagaccccaaaattccaggtcctgaagacaggacagagca
tgacactgcagtgtgcccaggatatgaaccatgaatacatgtcctggtatcgacaaga
cccaggcatggggctgaggctgattcattactcagttggtgctggtatcactgaccaa
ggagaagtccccaatggctacaatgtctccagatcaaccacagaggatttcccgctca
ggctgctgtcggctgctccctcccagacatctgtgtacttctgtgccagcaggccggg
actagcgggagggcgaccagagcagtacttcgggccgggcaccaggctcacggtcaca
gaggacctgaaaaacgtgttcccacccgaggtcgctgtgtttgagccatcagaagcag
agatctcccacacccaaaaggccacactggtgtgcctggccacaggcttctaccccga
ccacgtggagctgagctggtgggtgaatgggaaggaggtgcacagtgggtctgcaca
gacccgcagccctcaaggagcagccgccctcaatgactccagatacgctctgagca
gccgcctgagggtctcggccaccttctggcaggaccccgcaaccacttccgctgtca
agtccagttctacgggctctcggagaatgacgagtggacccaggatagggccaaccc
gtcacccagatcgtcagcgccgaggcctggggtagagcagactaa

Figure 4a

```
MQ
KEVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDKCVL DMRSMDFKSN SAVAWSNKSD FACANAFNNS IIPEDTFFPS
PESS*
```

Figure 4b

```
M
NAGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VCTDPQPLKE QPALNDSRYA LSSRLRVSAT
FWQDPRNHFR CQVQFYGLSE NDEWTQDRAK PVTQIVSAEA WGRAD*
```

Figure 5
5a
Full length A6 Tax TCR cDNA
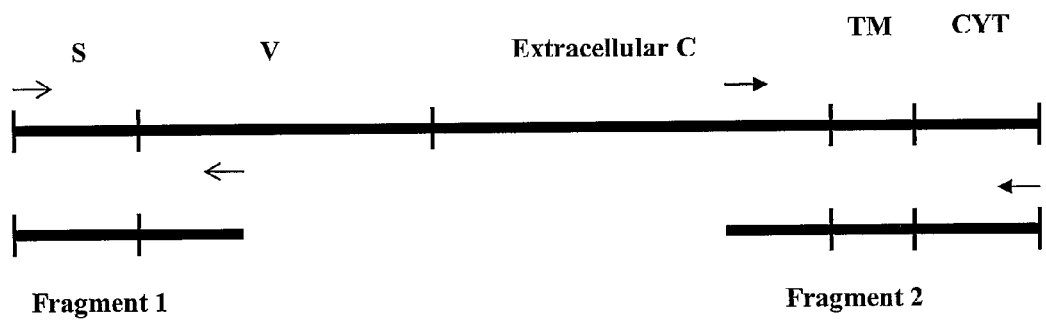
Fragment 1　　　　　　　　　　　　　　Fragment 2
5b
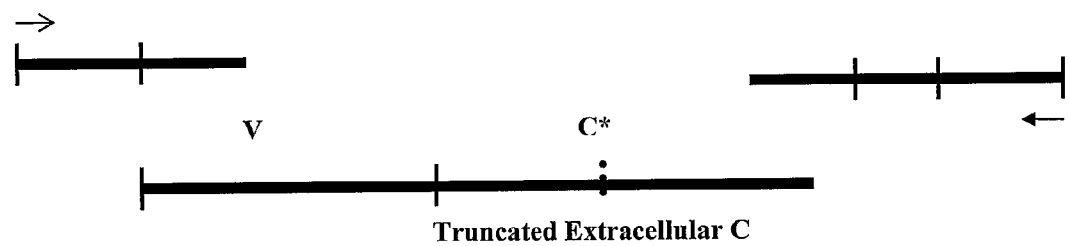
Sol DiS A6 Tax TCR
5c
Full length DiS A6 Tax TCR DNA

Figure 6a

```
        M   M   K   S   L   R   V     L   L   V     I   L   W   L     Q   L   S     W   V   W
  1   ATGATGAAAT CCTTGAGAGT TTTACTAGTG ATCCTGTGGC TTCAGTTGAG CTGGGTTTGG
        S   Q   Q   K   E   V   E     Q   N   S     G   P   L   S     V   P   E     G   A   I
 61   AGCCAACAGA AGGAAGTGGA GCAGAACTCT GGACCCCTCA GTGTTCCAGA GGGAGCCATT
        A   S   L   N   C   T   Y     S   D   R     G   S   Q   S     F   F   W     Y   R   Q
121   GCCTCTCTCA ACTGCACTTA CAGTGACCGA GGTTCCCAGT CCTTCTTCTG GTACAGACAA
        Y   S   G   K   S   P   E     L   I   M     S   I   Y   S     N   G   D     K   E   D
181   TATTCTGGGA AAAGCCCTGA GTTGATAATG TCCATATACT CCAATGGTGA CAAAGAAGAT
        G   R   F   T   A   Q   L     N   K   A     S   Q   Y   V     S   L   L     I   R   D
241   GGAAGGTTTA CAGCACAGCT CAATAAAGCC AGCCAGTATG TTTCTCTGCT CATCAGAGAC
        S   Q   P   S   D   S   A     T   Y   L     C   A   V   T     D   S   W     G   K
301   TCCCAGCCCA GTGATTCAGC CACCTACCTC TGTGCCGTTA CAACTGACAG CTGGGGGAAA
        L   Q   F   G   A   G   T     Q   V   V     V   T   P   D     I   Q   N     P   D   P
361   TTGCAGTTTG GAGCAGGGAC CCAGGTTGTG GTCACCCCAG ATATCCAGAA CCCTGACCCT
        A   V   Y   Q   L   R   D     S   K   S     S   D   K   S     V   C   L     F   T   D
421   GCCGTGTACC AGCTGAGAGA CTCTAAATCC AGTGACAAGT CTGTCTGCCT ATTCACCGAT
        F   D   S   Q   T   N   V     S   Q   S     K   D   S   D     V   Y   I     T   D   K
481   TTTGATTCTC AAACAAATGT GTCACAAAGT AAGGATTCTG ATGTGTATAT CACAGACAAA
        C   V   L   D   M   R   S     M   D   F     K   S   N   S     A   V   A     W   S   N
541   TGTGTGCTAG ACATGAGGTC TATGGACTTC AAGAGCAACA GTGCTGTGGC CTGGAGCAAC
        K   S   D   F   A   C   A     N   F   N     N   S   I   I     P   E   D     T   F
601   AAATCTGACT TTGCATGTGC AAACGCCTTC AACAACAGCA TTATTCCAGA AGACACCTTC
        F   P   S   P   E   S   S     S   D   V     K   L   V   E     K   S   F     E   T   D
661   TTCCCCAGCC CAGAAAGTTC CTCTGATGTC AAGCTGGTCG AGAAAAGCTT TGAAACAGAT
        T   N   L   N   F   Q   N     L   S   V     I   G   F   R     I   L   L     L   K   V
721   ACGAACCTAA ACTTTCAAAA CCTGTCAGTG ATTGGGTTCC GAATCCTCCT CCTGAAAGTG
        A   G   F   N   L   L   M     T   L   R     L   W   S   S     *
781   GCCGGGTTTA ATCTGCTCAT GACGCTGCGG CTGTGGTCCA GCTAA
```

Figure 6b

```
         M  S  I  G  L  L  C     C  A  A     L  S  L  L     W  A  G     P  V  N
  1   ATGAGCATCG GCCTCCTGTG CTGTGCAGCC TTGTCTCTCC TGTGGGCAGG TCCAGTGAAC
         A  G  V  T     Q  T  P     K  F  Q     V  L  K  T     G  Q  S     M  T  L
 61   GCTGGTGTCA CTCAGACCCC AAAATTCCAG GTCCTGAAGA CAGGACAGAG CATGACACTG
         Q  C  A  Q     D  M  N     H  E  Y     M  S  W  Y     R  Q  D     P  G  M
121   CAGTGTGCCC AGGATATGAA CCATGAATAC ATGTCCTGGT ATCGACAAGA CCCAGGCATG
         G  L  R  L     I  H  Y     S  V  G     A  G  I  T     D  Q  G     E  V  P
181   GGGCTGAGGC TGATTCATTA CTCAGTTGGT GCTGGTATCA CTGACCAAGG AGAAGTCCCC
         N  G  Y  N     V  S  R     S  T  T     E  D  F  P     L  R  L     L  S  A
241   AATGGCTACA ATGTCTCCAG ATCAACCACA GAGGATTTCC CGCTCAGGCT GCTGTCGGCT
         A  P  S  Q     T  S  V     Y  F  C     A  S  R  P     G  L  A     G  G  R
301   GCTCCCTCCC AGACATCTGT GTACTTCTGT GCCAGCAGGC CGGGACTAGC GGGAGGGCGA
         P  E  Q  Y     F  G  P     G  T  R     L  T  V  T     E  D  L     K  N  V
361   CCAGAGCAGT ACTTCGGGCC GGGCACCAGG CTCACGGTCA CAGAGGACCT GAAAAACGTG
         F  P  P  E     V  A  V     F  E  P     S  E  A  E     I  S  H     T  Q  K
421   TTCCCACCCG AGGTCGCTGT GTTTGAGCCA TCAGAAGCAG AGATCTCCCA CACCCAAAAG
         A  T  L  V     C  L  A     T  G  F     Y  P  D  H     V  E  L     S  W  W
481   GCCACACTGG TGTGCCTGGC CACAGGCTTC TACCCCGACC ACGTGGAGCT GAGCTGGTGG
         V  N  G  K     E  V  H     S  G  V     C  T  D  P     Q  P  L     K  E  Q
541   GTGAATGGGA AGGAGGTGCA CAGTGGGGTC TGCACAGACC CGCAGCCCCT CAAGGAGCAG
         P  A  L  N     D  S  R     Y  C  L     S  S  R  L     R  V  S     A  T  F
601   CCCGCCCTCA ATGACTCCAG ATACTGCCTG AGCAGCCGCC TGAGGGTCTC GGCCACCTTC
         W  Q  D  P     R  N  H     F  R  C     Q  V  Q  F     Y  G  L     S  E  N
661   TGGCAGGACC CCCGCAACCA CTTCCGCTGT CAAGTCCAGT TCTACGGGCT CTCGGAGAAT
         D  E  W  T     Q  D  R     A  K  P     V  T  Q  I     V  S  A     E  A  W
721   GACGAGTGGA CCCAGGATAG GGCCAAACCC GTCACCCAGA TCGTCAGCGC CGAGGCCTGG
         G  R  A  D     S  G  F     T  S  E     S  Y  Q  Q     G  V  L     S  A  T
781   GGTAGAGCAG ACTCTGGCTT CACCTCCGAG TCTTACCAGC AAGGGGTCCT GTCTGCCACC
         I  L  Y  E     I  L  L     G  K  A     T  L  Y  A     V  L  V     S  A  L
841   ATCCTCTATG AGATCTTGCT AGGGAAGGCC ACCTTGTATG CCGTGCTGGT CAGTGCCCTC
         V  L  M  A     V  K  R     K  D     S  R  G  *
901   GTGCTGATGG CCATGGTAAA GAGAAAGGAT TCCAGAGGCT AA
```

Figure 7a

TRAC:
aatatccagaaccctgaccctgccgtgtaccagctgagagactctaaatccagtgacaagtctgtctgcctattcaccgattttgattctca
aacaaatgtgtcacaaagtaaggattctgatgtgtatatcacagacaaaactgtgctagacatgaggtctatggacttcaagagcaacag
tgctgtggcctggagcaacaaatctgactttgcatgtgcaaacgccttcaacaacagcattattccagaagacaccttcttccccagccc
agaaagttcctgtgatgtcaagctggtcgagaaaagctttgaaacagatacgaacctaaactttcaaaacctgtcagtgattgggttccg
aatcctcctcctgaaagtggccgggtttaatctgctcatgacgctgcggctgtggtccagctga TRAV1-1:
atgtggggagctttccttctctatgtttccatgaagatgggaggcactgcaggacaaagccttgagcagccctctgaagtgacagctgt
ggaaggagccattgtccagataaactgcacgtaccagacatctgggttttatgggctgtcctggtaccagcaacatgatggcggagca
cccacatttctttcttacaatgctctggatggtttggaggagacaggtcgtttttcttcattccttagtcgctctgatagttatggttacctcctt
ctacaggagctccagatgaaagactctgcctcttacttctgcgctgtgagaga TRAV1-2:
atgtggggagttttccttcttatgtttccatgaagatgggaggcactacaggacaaaacattgaccagcccactgagatgacagctacg
gaaggtgccattgtccagatcaactgcacgtaccagacatctgggttcaacgggctgttctggtaccagcaacatgctggcgaagcac
ccacatttctgtcttacaatgttctggatggtttggaggagaaaggtcgttttcttcattccttagtcggtctaaagggtacagttacctcctt
ttgaaggagctccagatgaaagactctgcctcttacctctgtgctgtgagaga TRAV2:
atggctttgcagagcactctgggggcggtgtggctagggcttctcctcaactctctctggaaggttgcagaaagcaaggaccaagtgtt
tcagccttccacagtggcatcttcagagggagctgtggtggaaatcttctgtaatcactctgtgtccaatgcttacaacttcttctggtacct
tcacttcccgggatgtgcaccaagactccttgttaaaggctcaaagccttctcagcagggacgatacaacatgacctatgaacggttctc
ttcatcgctgctcatcctccaggtgcgggaggcagatgctgctgtttactactgtgctgtggagga TRAV3:
Atggcctctgcacccatctcgatgcttgcgatgctcttcacattgagtgggctgagagctcagtcagtggctcagccggaagatcaggt
caacgttgctgaagggaatcctctgactgtgaaatgcacctattcagtctctggaaaccccttatctttttttggtatgttcaataccccaaccg
aggcctccagttcctctgaaatacatcacaggggataacctggttaaaggcagctatggctttgaagctgaatttaacaagagccaaac
ctccttccacctgaagaaaccatctgcccttgtgagcgactccgctttgtacttctgtgctgtgagagaca TRAV4:
atgaggcaagtggcgagagtgatcgtgttcctgaccctgagtactttgagccttgctaagaccacccagcccatctccatggactcatat
gaaggacaagaagtgaacataacctgtagccacaacaacattgctacaaatgattatatcacgtggtaccaacagtttcccagccaag
gaccacgatttattattcaaggatacaagacaaaagttacaaacgaagtggcctccctgtttatccctgccgacagaaagtccagcactc
tgagcctgcccgggtttccctgagcgacactgctgtgtactactgcctcgtgggtgaca

Figure 7b

TRAV5:
atgaagacatttgctggattttcgttcctgtttttgtggctgcagctggactgtatgagtagaggagaggatgtggagcagagtctttcct
gagtgtccgagagggagacagctccgttataaactgcacttacacagacagctcctccacctacttatactggtataagcaagaacctg
gagcaggtctccagttgctgacgtatattttcaaatatggacatgaaacaagaccaaagactcactgttctattgaataaaaaggataa
acatctgtctctgcgcattgcagacacccagactggggactcagctatctacttctgtgcagagagta TRAV6:
atggagtcattcctgggaggtgttttgctgattttgtggcttcaagtggactgggtgaagagccaaaagatagaacagaattccgaggcc
ctgaacattcaggagggtaaaacggccaccctgacctgcaactatacaaactattccccagcatacttacagtggtaccgacaagatcc
aggaagaggccctgttttcttgctactcatacgtgaaaatgagaaagaaaaaaggaaagaaagactgaaggtcacctttgataccacc
cttaaacagagtttgtttcatatcacagcctcccagcctgcagactcagctacctacctctgtgctctagaca TRAV7:
atggagaagatgcggagacctgtcctaattatattttgtctatgtcttggctgggcaaatggagaaaaccaggtggagcacagccctcat
tttctgggaccccagcagggagacgttgcctccatgagctgcacgtactctgtcagtcgttttaacaatttgcagtggtacaggcaaaat
acagggatgggtcccaaacacctattatccatgtattcagctggatatgagaagcagaaaggaagactaaatgctacattactgaagaa
tggaagcagcttgtacattacagccgtgcagcctgaagattcagccacctatttctgtgctgtagatg TRAV8-1:
atgctcctgttgctcataccagtgctggggatgattttttgccctgagagatgccagagcccagtctgtgagccagcataaccaccacgta
attctctctgaagcagcctcactggagttgggatgcaactattcctatggtggaactgttaatctcttctggtatgtccagtaccctggtcaa
caccttcagcttctcctcaagtacttttcaggggatccactggttaaaggcatcaagggctttgaggctgaatttataaagagtaaattctc
ctttaatctgaggaaaccctctgtgcagtggagtgacacagctgagtacttctgtgccgtgaatgc TRAV8-2:
atgctcctgctgctcgtcccagtgctcgaggtgatttttactctgggaggaaccagagcccagtcggtgacccagcttgacagccacgt
ctctgtctctgaaggaaccccggtgctgctgaggtgcaactactcatcttcttattcaccatctctcttctggtatgtgcaacaccccaaca
aaggactccagcttctcctgaagtacacatcagcggccaccctggttaaaggcatcaacggttttgaggctgaatttaagaagagtgaa
acctccttccacctgacgaaaccctcagcccatatgagcgacgcggctgagtacttctgtgttgtgagtga TRAV8-3:
atgctcctggagcttatcccactgctggggatacattttgtcctgagaactgccagagcccagtcagtgacccagcctgacatccacatc
actgtctctgaaggagcctcactggagttgagatgtaactattcctatgggcaacaccttatctcttctggtatgtccagtcccccggcc
aaggcctccagctgctcctgaagtacttttcaggagacactctggttcaaggcattaaaggctttgaggctgaatttaagaggagtcaat
cttccttcaatctgaggaaaccctctgtgcattggagtgatgctgctgagtacttctgtgctgtgggtgc

Figure 7c

TRAV8-4:
atgctcctgctgctcgtcccagtgctcgaggtgatttttaccctgggaggaaccagagcccagtcggtgacccagcttggcagccacg
tctctgtctctgaaggagcccctggttctgctgaggtgcaactactcatcgtctgttccaccatatctcttctggtatgtgcaatacccaacc
aaggactccagcttctcctgaagtacacatcagcggccaccctggttaaaggcatcaacggttttgaggctgaatttaagaagagtgaa
acctccttccacctgacgaaaccctcagcccatatgagcgacgcggctgagtacttctgtgctgtgagtga TRAV8-6:
atgctcctgctgctcgtcccagcgttccaggtgatttttaccctgggaggaaccagagcccagtctgtgacccagcttgacagccaagt
ccctgtctttgaagaagcccctgtggagctgaggtgcaactactcatcgtctgtttcagtgtatctcttctggtatgtgcaatacccaacc
aaggactccagcttctcctgaagtatttatcaggatccaccctggttaaaggcatcaacggttttgaggctgaatttaacaagagtcaaac
ttccttccacttgaggaaaccctcagtccatataagcgacacggctgagtacttctgtgctgtgagtga TRAV8-7:
atgctcttagtggtcattctgctgcttggaatgttcttcacactgagaggaaccagaacccagtcggtgacccagcttgatggccacatc
actgtctctgaagaagcccctctggaactgaagtgcaactattcctatagtggagttccttctctcttctggtatgtccaatactctagccaa
agcctccagcttctcctcaaagacctaacagaggccaccccaggttaaaggcatcagaggttttgaggctgaatttaagaagagcgaaa
cctccttctacctgaggaaaccatcaacccatgtgagtgatgctgctgagtacttctgtgctgtgggtgacaggag TRAV9-1:
atgaattcttctccaggaccagcgattgcactattcttaatgtttgggggaatcaatggagattcagtggtccagacagaaggccaagtg
ctccccctctgaaggggattccctgattgtgaactgctcctatgaaaccacacagtaccctccctttttggtatgtccaatatcctggagaa
ggtccacagctccacctgaaagccatgaaggccaatgacaagggaaggaacaaaggttttgaagccatgtaccgtaaagaaaccac
ttctttccacttggagaaagactcagttcaagagtcagactccgctgtgtacttctgtgctctgagtga TRAV9-2:
atgaactattctccaggcttagtatctctgatactcttactgcttggaagaacccgtggaaattcagtgacccagatggaagggccagtg
actctctcagaagaggccttcctgactataaactgcacgtacacagccacaggataccctttcccttttctggtatgtccaatatcctggag
aaggtctacagctcctcctgaaagccacgaaggctgatgacaagggaagcaacaaaggttttgaagccacataccgtaaagaaacca
cttctttccacttggagaaaggctcagttcaagtgtcagactcagcggtgtacttctgtgctctgagtga TRAV10:
atgaaaaagcatctgacgaccttcttggtgattttgtggctttattttttataggggggaatggcaaaaaccaagtggagcagagtcctcagt
ccctgatcatcctggagggaaagaactgcactcttcaatgcaattatacagtgagcccttcagcaacttaaggtggtataagcaagata
ctgggagaggtcctgtttccctgacaatcatgactttcagtgagaacacaaagtcgaacggaagatatacagcaactctggatgcagac
acaaagcaaagctctctgcacatcacagcctcccagctcagcgattcagcctcctacatctgtgtggtgagcg

Figure 7d

TRAV12-1:
atgatatccttgagagttttactggtgatcctgtggcttcagttaagctgggtttggagccaacggaaggaggtggagcaggatcctgga
cccttcaatgttccagagggagccactgtcgcttcaactgtacttacagcaacagtgcttctcagtctttcttctggtacagacaggattg
caggaaagaacctaagttgctgatgtccgtatactccagtggtaatgaagatggaaggtttacagcacagctcaatagagccagccag
tatatttccctgctcatcagagactccaagctcagtgattcagccacctacctctgtgtggtgaaca TRAV12-2:
atgatgaaatccttgagagttttactagtgatcctgtggcttcagttgagctgggtttggagccaacagaaggaggtggagcagaattct
ggaccccctcagtgttccagagggagccattgcctctctcaactgcacttacagtgaccgaggttcccagtccttcttctggtacagacaa
tattctgggaaaagccctgagttgataatgttcatatactccaatggtgacaaagaagatggaaggtttacagcacagctcaataaagcc
agccagtatgtttctctgctcatcagagactcccagcccagtgattcagccacctacctctgtgccgtgaaca TRAV12-3:
atgatgaaatccttgagagttttactggtgatcctgtggcttcagttaagctgggtttggagccaacagaaggaggtggagcaggatcct
ggaccactcagtgttccagagggagccattgtttctctcaactgcacttacagcaacagtgcttttcaatacttcatgtggtacagacagta
ttccagaaaaggccctgagttgctgatgtacacatactccagtggtaacaaagaagatggaaggtttacagcacaggtcgataaatcca
gcaagtatatctccttgttcatcagagactcacagcccagtgattcagccacctacctctgtgcaatgagcg TRAV13-1:
atgacatccattcgagctgtatttatattcctgtggctgcagctggacttggtgaatggagagaatgtggagcagcatccttcaaccctga
gtgtccaggagggagacagcgctgttatcaagtgtacttattcagacagtgcctcaaactacttcccttggtataagcaagaacttggaa
aaggacctcagcttattatagacattcgttcaaatgtgggcgaaaagaaagaccaacgaattgctgttacattgaacaagacagccaaa
catttctccctgcacatcacagagacccaacctgaagactcggctgtctacttctgtgcagcaagta TRAV13-2:
atggcaggcattcgagctttatttatgtacttgtggctgcagctggactgggtgagcagaggagagagtgtggggctgcatcttcctacc
ctgagtgtccaggagggtgacaactctattatcaactgtgcttattcaaacagcgcctcagactacttcatttggtacaagcaagaatctg
gaaaaggtcctcaattcattatagacattcgttcaaatatggacaaaaggcaaggccaaagagtcaccgttttattgaataagacagtga
acatctctctctgcaaattgcagctactcaacctggagactcagctgtctacttttgtgcagagaata TRAV14:
atgtcactttctagcctgctgaaggtggtcacagcttcactgtggctaggacctggcattgcccagaagataactcaaacccaaccagg
aatgttcgtgcaggaaaaggaggctgtgactctggactgcacatatgacaccagtgatcaaagttatggtctattctggtacaagcagc
ccagcagtggggaaatgattttcttatttatcagggggtcttatgacgagcaaaatgcaacagaaggtcgctactcattgaatttccagaa
ggcaagaaaatccgccaaccttgtcatctccgcttcacaactgggggactcagcaatgtatttctgtgcaatgagagaggg

Figure 7e

TRAV16:
atgaagcccaccctcatctcagtgcttgtgataatatttatactcagaggaacaagagcccagagagtgactcagcccgagaagctcct
ctctgtctttaaaggggcccagtggagctgaagtgcaactattcctattctgggagtcctgaactcttctggtatgtccagtactccagac
aacgcctccagttactcttgagacacatctctagagagagcatcaaaggcttcactgctgaccttaacaaaggcgagacatctttccacc
tgaagaaaccatttgctcaagaggaagactcagccatgtattactgtgctctaagtgg TRAV17:
atggaaactctcctgggagtgtctttggtgattctatggcttcaactggctagggtgaacagtcaacagggagaagaggatcctcaggc
cttgagcatccaggagggtgaaaatgccaccatgaactgcagttacaaaactagtataaacaatttacagtggtatagacaaaattcag
gtagaggccttgtccacctaattttaatacgttcaaatgaaagagagaaacacagtggaagattaagagtcacgcttgacacttccaaga
aaagcagttccttgttgatcacggcttcccgggcagcagacactgcttcttacttctgtgctacggacg TRAV18:
atgctgtctgcttcctgctcaggacttgtgatcttgttgatattcagaaggaccagtggagactcggttacccagacagaaggcccagtta
ccctccctgagagggcagctctgacattaaactgcacttatcagtccagctattcaacttttctattctggtatgtccagtatctaaacaaag
agcctgagctcctcctgaaaagttcagaaaaccaggagacggacagcagaggttttcaggccagtcctatcaagagtgacagttcctt
ccacctggagaagccctcggtgcagctgtcggactctgccgtgtactactgcgctctgagaga TRAV19:
atgctgactgccagcctgttgagggcagtcatagcctccatctgtgttgtatccagcatggctcagaaggtaactcaagcgcagactga
aatttctgtggtggagaaggaggatgtgaccttggactgtgtgtatgaaacccgtgatactacttattacttattctggtacaagcaaccac
caagtggagaattggttttccttattcgtcggaactctttttgatgagcaaaatgaaataagtggtcggtattcttggaacttccagaaatcca
ccagttccttcaacttcaccatcacagcctcacaagtcgtggactcagcagtatacttctgtgctctgagtgaggc TRAV20:
atggagaaaatgttggagtgtgcattcatagtcttgtggcttcagcttggctggttgagtggagaagaccaggtgacgcagagtcccga
ggccctgagactccaggaggggagagagtagcagtcttaactgcagttacacagtcagcggtttaagagggctgttctggtataggcaa
gatcctgggaaaggccctgaattcctcttcaccctgtattcagctggggaagaaaaggagaaagaaaggctaaaagccacattaacaa
agaaggaaagctttctgcacatcacagcccctaaacctgaagactcagccacttatctctgtgctgtgcagg TRAV21:
atggagaccctcttgggcctgcttatcctttggctgcagctgcaatgggtgagcagcaaacaggaggtgacgcagattcctgcagctct
gagtgtcccagaaggagaaaacttggttctcaactgcagtttcactgatagcgctatttacaacctccagtggtttaggcaggaccctgg
gaaaggtctcacatctctgttgcttattcagtcaagtcagagagagcaaacaagtggaagacttaatgcctcgctggataaatcatcagg
acgtagtactttatacattgcagcttctcagcctggtgactcagccacctacctctgtgctgtgagg

Figure 7f

TRAV22:
atgaagaggatatttgggagctctgctgggggctcttgagtgcccaggtttgctgtgtgagaggaatacaagtggagcagagtcctccag
acctgattctccaggagggagccaattccacgctgcggtgcaatttttctgactctgtgaacaatttgcagtggtttcatcaaaaccottgg
ggacagctcatcaacctgttttacattccctcagggacaaaacagaatggaagattaagcgccacgactgtcgctacggaacgctaca
gcttattgtacatttcctcttcccagaccacagactcaggcgtttatttctgtgctgtggagc TRAV23:
atggacaagatcttaggagcatcattttagttctgtggcttcaactatgctgggtgagtggccaacagaaggagaaaagtgaccagca
gcaggtgaaacaaagtcctcaatctttgatagtccagaaaggagggatttcaattataaactgtgcttatgagaacactgcgtttgactac
tttccatggtaccaacaattccctgggaaaggccctgcattattgatagccatacgtccagatgtgagtgaaaagaaagaaggaagatt
cacaatctccttcaataaaagtgccaagcagttctcattgcatatcatggattcccagcctggagactcagccacctacttctgtgcagca
agca TRAV24:
atggagaagaatcctttggcagccccattactaatcctctggtttcatcttgactgcgtgagcagcatactgaacgtggaacaaagtcctc
agtcactgcatgttcaggagggagacagcaccaatttcacctgcagcttcccttccagcaatttttatgccttacactggtacagatggga
aactgcaaaaagccccgaggccttgtttgtaatgactttaaatggggatgaaaagaagaaaggacgaataagtgccactcttaatacca
aggagggttacagctatttgtacatcaaaggatcccagcctgaagactcagccacatacctctgtgcccttta TRAV25:
atgctactcatcacatcaatgttggtcttatggatgcaattgtcacaggtgaatggacaacaggtaatgcaaattcctcagtaccagcatgt
acaagaaggagaggacttcaccacgtactgcaattcctcaactactttaagcaatatacagtggtataagcaaaggcctggtggacatc
ccgttttttgatacagttagtgaagagtggagaagtgaagaagcagaaaagactgacatttcagtttggagaagcaaaaaagaacagc
tccctgcacatcacagccacccagactacagatgtaggaacctacttctgtgcaggg TRAV26-1:
atgaggctggtggcaagagtaactgtgtttctgacctttggaactataattgatgctaagaccacccagccccccctccatggattgcgct
gaaggaagagctgcaaacctgccttgtaatcactctaccatcagtggaaatgagtatgtgtattggtatcgacagattcactcccaggggg
ccacagtatatcattcatggtctaaaaaacaatgaaaccaatgaaatggcctctctgatcatcacagaagacagaaagtccagcaccttg
atcctgccccacgctacgctgagagacactgctgtgtactattgcatcgtcagagtcg TRAV26-2:
atgaagttggtgacaagcattactgtactcctatctttgggtattatgggtgatgctaagaccacacagccaaattcaatggagagtaacg
aagaagagcctgttcacttgccttgtaaccactccacaatcagtggaactgattacatacattggtatcgacagcttccctcccagggtcc
agagtacgtgattcatggtcttacaagcaatgtgaacaacagaatggcctctctggcaatcgctgaagacagaaagtccagtaccttga
tcctgcaccgtgctaccttgagagatgctgctgtgtactactgcatcctgagagac TRAV27:
atggtcctgaaattctccgtgtccattctttggattcagttggcatgggtgagcacccagctgctggagcagagccctcagtttctaagca
tccaagagggagaaaatctcactgtgtactgcaactcctcaagtgttttttccagcttacaatggtacagacaggagcctggggaaggtc
ctgtcctcctggtgacagtagttacgggtggagaagtgaagaagctgaagagactaaccttcagtttggtgatgcaagaaaggacagt
tctctccacatcactgcagcccagcctggtgatacaggcctctacctctgtgcaggag

Figure 7g

TRAV29:
atggccatgctcctgggggcatcagtgctgattctgtggcttcagccagactgggtaaacagtcaacagaagaatgatgaccagcaag
ttaagcaaaattcaccatccctgagcgtccaggaaggaagaatttctattctgaactgtgactatactaacagcatgtttgattatttcctat
ggtacaaaaaatacccctgctgaaggtcctacattcctgatatctataagttccattaaggataaaaatgaagatggaagattcactgtcttc
ttaaacaaaagtgccaagcacctctctctgcacattgtgccctcccagcctggagactctgcagtgtacttctgtgcagcaagcg TRAV30:
atggagactctcctgaaagtgctttcaggcaccttgttgtggcagttgacctgggtgagaagccaacaaccagtgcagagtcctcaagc
cgtgatcctccgagaaggggaagatgctgtcatcaactgcagttcctccaaggctttatattctgtacactggtacaggcagaagcatg
gtgaagcacccgtcttcctgatgatattactgaagggtggagaacagaagggtcatgaaaaaatatctgcttcatttaatgaaaaaaagc
agcaaagctccctgtaccttacggcctcccagctcagttactcaggaacctacttctgcggcacagaga TRAV34:
atggagactgttctgcaagtactcctagggatattgggggttccaagcagcctgggtcagtagccaagaactggagcagagtcctcagt
ccttgatcgtccaagagggaaagaatctcaccataaactgcacgtcatcaaagacgttatatggcttatactggtataagcaaaagtatg
gtgaaggtcttatcttcttgatgatgctacagaaaggtggggaagagaaaagtcatgaaaagataactgccaagttggatgagaaaaa
gcagcaaagttccctgcatatcacagcctcccagcccagccatgcaggcatctacctctgtggagcagaca TRAV35:
atgctccttgaacatttattaataatcttgtggatgcagctgacatgggtcagtggtcaacagctgaatcagagtcctcaatctatgtttatc
caggaaggagaagatgtctccatgaactgcacttcttcaagcatatttaacacctggctatggtacaagcaggaacctggggaaggtc
ctgtcctcttgatagcctatataaggctggtgaattgacctcaaatggaagactgactgctcagtttggtataaccagaaaggacagctt
cctgaatatctcagcatccatacctagtgatgtaggcatctacttctgtgctgggcag TRAV36:
atgatgaagtgtccacaggctttactagctatcttttggcttctactgagctgggtgagcagtgaagacaaggtggtacaaagccctctat
ctctggttgtccacgagggagacaccgtaactctcaattgcagttatgaagtgactaactttcgaagcctactatggtacaagcaggaaa
agaaagctcccacatttctatttatgctaacttcaagtggaattgaaaagaagtcaggaagactaagtagcatattagataagaaagaact
ttccagcatcctgaacatcacagccacccagaccggagactcggccatctacctctgtgctgtggagg TRAV38-1:
atgacacgagttagcttgctgtgggcagtcgtggtctccacctgtcttgaatccggcatggcccagacagtcactcagtctcaaccaga
gatgtctgtgcaggaggcagagactgtgacccctgagttgcacatatgacaccagtgagaataattattatttgttctggtacaagcagcct
cccagcaggcagatgattctcgttattcgccaagaagcttataagcaacagaatgcaacggagaatcgtttctctgtgaacttccagaaa
gcagccaaatccttcagtctcaagatctcagactcacagctgggggacactgcgatgtatttctgtgctttcatgaagca

Figure 7h

TRAV38-2:
atggcatgccctggcttcctgtgggcacttgtgatctccacctgtcttgaatttagcatggctcagacagtcactcagtctcaaccagaga
tgtctgtgcaggaggcagagaccgtgaccctgagctgcacatatgacaccagtgagagtgattattatttattctggtacaagcagcctc
ccagcaggcagatgattctcgttattcgccaagaagcttataagcaacagaatgcaacagagaatcgtttctctgtgaacttccagaaag
cagccaaatccttcagtctcaagatctcagactcacagctgggggatgccgcgatgtatttctgtgcttataggagcg TRAV39:
atgaagaagctactagcaatgattctgtggcttcaactagaccggttaagtggagagctgaaagtggaacaaaaccctctgttcctgag
catgcaggagggaaaaaaactataccatctactgcaattattcaaccacttcagacagactgtattggtacaggcaggatcctgggaaaa
gtctggaatctctgtttgtgttgctatcaaatggagcagtgaagcaggagggacgattaatggcctcacttgataccaaagcccgtctca
gcaccctccacatcacagctgccgtgcatgacctctctgccacctacttctgtgccgtggaca TRAV40:
atgaactcctctctggactttctaattctgatcttaatgtttggaggaaccagcagcaattcagtcaagcagacgggccaaataaccgtct
cggagggagcatctgtgactatgaactgcacatacacatccacgggggtaccctacccttttctggtatgtggaatacccagcaaacct
ctgcagcttcttcagagagagacaatggaaaacagcaaaaacttcggaggcggaaatattaaagacaaaaactcccccattgtgaaat
attcagtccaggtatcagactcagccgtgtactactgtcttctgggaga TRAV41:
atggtgaagatccggcaattttttgttggctattttgtggcttcagctaagctgtgtaagtgccgccaaaaatgaagtggagcagagtcctc
agaacctgactgcccaggaaggagaatttatcacaatcaactgcagttactcggtaggaataagtgccttacactggctgcaacagcat
ccaggaggaggcattgtttccttgtttatgctgagctcagggaagaagaagcatggaagattaattgccacaataaacatacaggaaaa
gcacagctccctgcacatcacagcctcccatcccagagactctgccgtctacatctgtgctgtcaga

Figure 8a

TRBC1:
aggacctgaacaaggtgttcccacccgaggtcgctgtgtttgagccatcagaagcagagatctcccacacccaaaaggccacactgg
tgtgcctggccacaggcttcttccccgaccacgtggagctgagctggtgggtgaatgggaaggaggtgcacagtggggtcagcaca
gacccgcagcccctcaaggagcagcccgccctcaatgactccagatactgcctgagcagccgcctgagggtctcggccaccttctg
gcagaaccccgcaaccacttccgctgtcaagtccagttctacgggctctcggagaatgacgagtggacccaggatagggccaaac
ccgtcacccagatcgtcagcgccgaggcctggggtagagcagactgtggctttacctcggtgtcctaccagcaaggggtcctgtctg
ccaccatcctctatgagatcctgctagggaaggccaccctgtatgctgtgctggtcagcgcccttgtgttgatggccatggtcaagaga
aaggatttctga TRBC2:
aggacctgaaaaacgtgttcccacccgaggtcgctgtgtttgagccatcagaagcagagatctcccacacccaaaaggccacactgg
tatgcctggccacaggcttctaccccgaccacgtggagctgagctggtgggtgaatgggaaggaggtgcacagtggggtcagcaca
gacccgcagcccctcaaggagcagcccgccctcaatgactccagatactgcctgagcagccgcctgagggtctcggccaccttctg
gcagaaccccgcaaccacttccgctgtcaagtccagttctacgggctctcggagaatgacgagtggacccaggatagggccaaac
ccgtcacccagatcgtcagcgccgaggcctggggtagagcagactgtggcttcacctccgagtcttaccagcaaggggtcctgtctg
ccaccatcctctatgagatcttgctagggaaggccaccttgtatgccgtgctggtcagtgccctcgtgctgatggccatggtcaagaga
aaggattccagaggctag TRBV2:
atggatacctggctcgtatgctgggcaattttagtctcttgaaagcaggactcacagaacctgaagtcacccagactcccagccatcag
gtcacacagatgggacaggaagtgatcttgcgctgtgtccccatctctaatcacttatacttctattggtacagacaaatcttggggcaga
aagtcgagtttctggtttcctttataataatgaaatctcagagaagtctgaaatattcgatgatcaattctcagttgaaaggcctgatggatc
aaatttcactctgaagatccggtccacaaagctggaggactcagccatgtacttctgtgccagcagtgaagc TRBV3-1:
atgggctgcaggctcctctgctgtgtggtcttctgcctcctccaagcaggtcccttggacacagctgtttcccagactccaaaatacctg
gtcacacagatgggaaacgacaagtccattaaatgtgaacaaaatctgggccatgatactatgtattggtataaacaggactctaagaa
atttctgaagataatgtttagctacaataataaggagctcattataaatgaaacagttccaaatcgcttctcacctaaatctccagacaaag
ctcacttaaatcttcacatcaattccctggagcttggtgactctgctgtgtatttctgtgccagcagccaaga TRBV4-1:
atgggctgcaggctgctctgctgtgcggttctctgtctcctgggagcagttcccatagacactgaagttacccagacaccaaaacacct
ggtcatgggaatgacaaataagaagtctttgaaatgtgaacaacatatggggcacagggctatgtattggtacaagcagaaagctaag
aagccaccggagctcatgtttgtctacagctatgagaaactctctataaatgaaagtgtgccaagtcgcttctcacctgaatgccccaac
agctctctcttaaaccttcacctacacgccctgcagccagaagactcagccctgtatctctgcgccagcagccaaga

Figure 8b

TRBV4-2:
atgggctgcaggctgctctgctgtgcggttctctgtctcctgggagcggtccccatggaaacgggagttacgcagacaccaagacac
ctggtcatgggaatgacaaataagaagtctttgaaatgtgaacaacatctggggcataacgctatgtattggtacaagcaaagtgctaag
aagccactggagctcatgtttgtctacaactttaaagaacagactgaaaacaacagtgtgccaagtcgcttctcacctgaatgccccaac
agctctcacttattccttcacctacacaccctgcagccagaagactcggccctgtatctctgtgccagcagccaaga TRBV4-3:
atgggctgcaggctgctctgctgtgcggttctctgtctcctgggagcggtccccatggaaacgggagttacgcagacaccaagacac
ctggtcatgggaatgacaaataagaagtctttgaaatgtgaacaacatctgggtcataacgctatgtattggtacaagcaaagtgctaag
aagccactggagctcatgtttgtctacagtcttgaagaacgggttgaaaacaacagtgtgccaagtcgcttctcacctgaatgccccaac
agctctcacttattccttcacctacacaccctgcagccagaagactcggccctgtatctctgcgccagcagccaaga TRBV5-1:
atgggctccaggctgctctgttgggtgctgctttgtctcctgggagcaggcccagtaaaggctggagtcactcaaactccaagatatct
gatcaaaacgagaggacagcaagtgacactgagctgctccctatctctgggcataggagtgtatcctggtaccaacagaccccagg
acagggccttcagttcctctttgaatacttcagtgagacacagagaaacaaaggaaacttccctggtcgattctcagggcgccagttctc
taactctcgctctgagatgaatgtgagcaccttggagctgggggactcggccctttatctttgcgccagcagcttgg TRBV5-3:
atgggccccgggctcctctgctgggaactgctttatctcctgggagcaggcccagtggaggctggagtcacccaaagtcccacacac
ctgatcaaaacgagaggacagcaagtgactctgagatgctctcctatctctgggcacagcagtgtgtcctggtaccaacaggcccgg
gtcaggggccccagtttatctttgaatatgctaatgagttaaggagatcagaaggaaacttccctaatcgattctcagggcgccagttcc
atgactgttgctctgagatgaatgtgagtgccttggagctgggggactcggccctgtatctctgtgccagaagctt TRBV5-4:
atgggccctgggctcctctgctgggtgctgctttgtctcctgggagcaggctcagtggagactggagtcacccaaagtcccacacacc
tgatcaaaacgagaggacagcaagtgactctgagatgctcttctcagtctgggcacaacactgtgtcctggtaccaacaggccctggg
tcaggggccccagtttatctttcagtattatagggaggaagagaatggcagaggaaacttccctcctagattctcaggtctccagttccct
aattatagctctgagctgaatgtgaacgccttggagctggacgactcggccctgtatctctgtgccagcagcttgg TRBV5-5:
atgggccctgggctcctctgctgggtgctgctttgtctcctgggagcaggcccagtggacgctggagtcacccaaagtcccacacacc
tgatcaaaacgagaggacagcaagtgactctgagatgctctcctatctctgggcacaagagtgtgtcctggtaccaacaggtcctgggt
caggggccccagtttatctttcagtattatgagaaagaagagagaggaagaggaaacttccctgatcgattctcagctcgccagttccct
aactatagctctgagctgaatgtgaacgccttgttgctgggggactcggccctgtatctctgtgccagcagcttgg

Figure 8c

TRBV5-6:
atgggccccgggctcctctgctgggcactgctttgtctcctgggagcaggcttagtggacgctggagtcacccaaagtcccacacacc
tgatcaaaacgagaggacagcaagtgactctgagatgctctcctaagtctgggcatgacactgtgtcctggtaccaacaggccctggg
tcaggggccccagtttatctttcagtattatgaggaggaagagagacagagaggcaacttccctgatcgattctcaggtcaccagttccc
taactatagctctgagctgaatgtgaacgccttgttgctgggggactcggccctctatctctgtgccagcagcttgg TRBV5-7:
atgggccccgggctcctctgctgggtgctgctttgtcccctaggagaaggcccagtggacgctggagtcacccaaagtcccacacac
ctgatcaaaacgagaggacagcacgtgactctgagatgctctcctatctctgggcacaccagtgtgtcctcgtaccaacaggccctgg
gtcaggggccccagtttatctttcagtattatgagaaagaagagagaggaagaggaaacttccctgatcaattctcaggtcaccagttcc
ctaactatagctctgagctgaatgtgaacgccttgttgctagggactcggccctctatctctgtgccagcagcttgg TRBV5-8:
atgggacccaggctcctcttctgggcactgctttgtctcctcggaacaggcccagtggaggctggagtcacacaaagtcccacacacc
tgatcaaaacgagaggacagcaagcgactctgagatgctctcctatctctgggcacaccagtgtgtactggtaccaacaggccctggg
tctgggcctccagttcctcctttggtatgacgagggtgaagagagaaacagaggaaacttccctcctagattttcaggtcgccagttccc
taattatagctctgagctgaatgtgaacgccttggagctggaggactcggccctgtatctctgtgccagcagcttgg TRBV6-1:
atgagcatcgggctcctgtgctgtgtggcctttctctcctgtgggcaagtccagtgaatgctggtgtcactcagaccccaaaattccag
gtcctgaagacaggacagagcatgacactgcagtgtgcccaggatatgaaccataactccatgtactggtatcgacaagacccaggc
atgggactgaggctgatttattactcagcttctgagggtaccactgacaaaggagaagtccccaatggctacaatgtctccagattaaac
aaacgggagttctcgctcaggctggagtcggctgctccctcccagacatctgtgtacttctgtgccagcagtgaagc TRBV6-2:
atgagcctcgggctcctgtgctgtgggggccttttctctcctgtgggcaggtccagtgaatgctggtgtcactcagaccccaaaattccgg
gtcctgaagacaggacagagcatgacactgctgtgtgcccaggatatgaaccatgaatacatgtactggtatcgacaagacccaggc
atgggggctgaggctgattcattactcagttggtgagggtacaactgccaaaggagaggtccctgatggctacaatgtctccagattaaa
aaaacagaatttcctgctggggttggagtcggctgctccctcccaaacatctgtgtacttctgtgccagcagttactc TRBV6-3:
atgagcctcgggctcctgtgctgtgggggtcttttctctcctgtgggcaggtccagtgaatgctggtgtcactcagaccccaaaattccgg
gtcctgaagacaggacagagcatgacactgctgtgtgcccaggatatgaaccatgaatacatgtactggtatcgacaagacccaggc
atgggggctgaggctgattcattactcagttggtgagggtacaactgccaaaggagaggtccctgatggctacaatgtctccagattaaa
aaaacagaatttcctgctggggttggagtcggctgctccctcccaaacatctgtgtacttctgtgccagcagttactc

Figure 8d

TRBV6-4:
atgagaatcaggctcctgtgctgtgtggccttttctctcctgtgggcaggtccagtgattgctgggatcacccaggcaccaacatctcag
atcctggcagcaggacggcgcatgacactgagatgtacccaggatatgagacataatgccatgtactggtatagacaagatctaggac
tggggctaaggctcatccattattcaaatactgcaggtaccactggcaaaggagaagtccctgatggttatagtgtctccagagcaaac
acagatgatttcccctcacgttggcgtctgctgtaccctctcagacatctgtgtacttctgtgccagcagtgactc TRBV6-5:
atgagcatcggcctcctgtgctgtgcagccttgtctctcctgtgggcaggtccagtgaatgctggtgtcactcagaccccaaaattccag
gtcctgaagacaggacagagcatgacactgcagtgtgcccaggatatgaaccatgaatacatgtcctggtatcgacaagacccaggc
atggggctgaggctgattcattactcagttggtgctggtatcactgaccaaggagaagtccccaatggctacaatgtctccagatcaacc
acagaggatttcccgctcaggctgctgtcggctgctccctcccagacatctgtgtacttctgtgccagcagttactc TRBV6-6:
atgagcatcagcctcctgtgctgtgcagcctttcctctcctgtgggcaggtccagtgaatgctggtgtcactcagaccccaaaattccgc
atcctgaagataggacagagcatgacactgcagtgtacccaggatatgaaccataactacatgtactggtatcgacaagacccaggca
tggggctgaagctgatttattattcagttggtgctggtatcactgataaaggagaagtcccgaatggctacaacgtctccagatcaacca
cagaggatttcccgctcaggctggagttggctgctccctcccagacatctgtgtacttctgtgccagcagttactc TRBV6-7:
atgagcctcgggctcctgtgctgtgtggccttttctctcctgtgggcaggtccaatgaatgctggtgtcactcagaccccaaaattccacg
tcctgaagacaggacagagcatgactctgctgtgtgcccaggatatgaaccatgaatacatgtatcggtatcgacaagacccaggcaa
ggggctgaggctgatttactactcagttgctgctgctctcactgacaaaggagaagttcccaatggctacaatgtctccagatcaaacac
agaggatttccccctcaagctggagtcagctgctccctctcagacttctgtttacttctgtgccagcagttactc TRBV6-8:
atgagcctcgggctcctgtgctgtgcggccttttctctcctgtgggcaggtcccgtgaatgctggtgtcactcagaccccaaaattccac
atcctgaagacaggacagagcatgacactgcagtgtgcccaggatatgaaccatggatacatgtcctggtatcgacaagacccaggc
atggggctgagactgatttactactcagctgctgctggtactactgacaaagaagtccccaatggctacaatgtctctagattaaacaca
gaggatttcccactcaggctggtgtcggctgctccctcccagacatctgtgtacttgtgtgccagcagttactc TRBV6-9:
atgagcatcgggctcctgtgctgtgtggccttttctctcctgtgggcaggtccagtgaatgctggtgtcactcagaccccaaaattccaca
tcctgaagacaggacagagcatgacactgcagtgtgcccaggatatgaaccatggatacttgtcctggtatcgacaagacccaggcat
ggggctgaggcgcattcattactcagttgctgctggtatcactgacaaaggagaagtccccgatggctacaatgtatccagatcaaaca
cagaggatttcccgctcaggctggagtcagctgctccctcccagacatctgtatacttctgtgccagcagttattc

Figure 8e

TRBV7-1:
atgggcacaaggctcctctgctgggcagccatatgtctcctgggggcagatcacacaggtgctggagtctcccagtccctgagacac
aaggtagcaaagaagggaaaggatgtagctctcagatatgatccaatttcaggtcataatgcccttattggtaccgacagagcctggg
gcagggcctggagttccaatttacttccaaggcaaggatgcagcagacaaatcggggcttccccgtgatcggttctctgcacagagg
tctgagggatccatctccactctgaagttccagcgcacacagcaggggggacttggctgtgtatctctgtgccagcagctcagc TRBV7-2:
atgggcaccaggctcctcttctgggtggccttctgtctcctgggggcagatcacacaggagctggagtctcccagtcccccagtaaca
aggtcacagagaagggaaaggatgtagagctcaggtgtgatccaatttcaggtcatactgcccttactggtaccgacagagcctggg
gcagggcctggagttttaatttacttccaaggcaacagtgcaccagacaaatcagggctgcccagtgatcgcttctctgcagagagga
ctgggggatccgtctccactctgacgatccagcgcacacagcaggaggactcggccgtgtatctctgtgccagcagcttagc TRBV7-3:
atgggcaccaggctcctctgctgggcagccctgtgcctcctgggggcagatcacacaggtgctggagtctcccagacccccagtaac
aaggtcacagagaagggaaaatatgtagagctcaggtgtgatccaatttcaggtcatactgcccttactggtaccgacaaagcctggg
gcagggcccagagtttctaatttacttccaaggcacgggtgcggcagatgactcagggctgcccaacgatcggttctttgcagtcagg
cctgagggatccgtctctactctgaagatccagcgcacagagcggggggactcagccgtgtatctctgtgccagcagcttaac TRBV7-4:
atgggcaccaggctcctctgctgggtggtcctgggtttcctagggacagatcacacaggtgctggagtctcccagtccccaaggtaca
aagtcgcaaagaggggacgggatgtagctctcaggtgtgattcaatttcgggtcatgtaaccctttattggtaccgacagaccctgggg
cagggctcagaggttctgacttactcccagagtgatgctcaacgagacaaatcagggcggcccagtggtcggttctctgcagagagg
cctgagagatccgtctccactctgaagatccagcgcacagagcaggggactcagctgtgtatctctgtgccagcagcttagc TRBV7-6:
atgggcaccagtctcctatgctgggtggtcctgggtttcctagggacagatcacacaggtgctggagtctcccagtctcccaggtacaa
agtcacaaagaggggacaggatgtagctctcaggtgtgatccaatttcgggtcatgtatcccttattggtaccgacaggccctggggc
agggcccagagtttctgacttacttcaattatgagcccaacaagacaaatcagggctgcccaatgatcggttctctgcagagaggcct
gagggatccatctccactctgacgatccagcgcacagagcagcgggactcggccatgtatcgctgtgccagcagcttagc TRBV7-7:
atgggtaccagtctcctatgctgggtggtcctgggtttcctagggacagatcacacaggtgctggagtctcccagtctcccaggtacaa
agtcacaaagaggggacaggatgtaactctcaggtgtgatccaatttcgagtcatgcaacccttattggtatcaacaggccctggggc
agggcccagagtttctgacttacttcaattatgagctcaaccagacaaatcagggctgcccagtgatcggttctctgcagagaggcct
gagggatccatctccactctgacgattcagcgcacagagcagcgggactcagccatgtatcgctgtgccagcagcttagc

Figure 8f

TRBV7-8:
atgggcaccaggctcctctgctgggtggtcctgggtttcctagggacagatcacacaggtgctggagtctcccagtcccctaggtaca
aagtcgcaaagagaggacaggatgtagctctcaggtgtgatccaatttcgggtcatgtatcccttttttggtaccaacaggccctggggc
aggggccagagtttctgacttatttccagaatgaagctcaactagacaaatcggggctgcccagtgatcgcttctttgcagaaaggcct
gagggatccgtctccactctgaagatccagcgcacacagcaggaggactccgccgtgtatctctgtgccagcagcttagc TRBV7-9:
atgggcaccagcctcctctgctggatggccctgtgtctcctgggggcagatcacgcagatactggagtctcccagaaccccagacac
aagatcacaaagaggggacagaatgtaactttcaggtgtgatccaatttctgaacacaaccgcctttattggtaccgacagaccctggg
gcagggcccagagtttctgacttacttccagaatgaagctcaactagaaaaatcaaggctgctcagtgatcggttctctgcagagaggc
ctaagggatctttctccaccttggagatccagcgcacagagcaggggggactcggccatgtatctctgtgccagcagcttagc TRBV9:
atgggcttcaggctcctctgctgtgtggccttttgtctcctgggagcaggcccagtggattctggagtcacacaaacccccaaagcacct
gatcacagcaactggacagcgagtgacgctgagatgctcccctaggtctggagacctctctgtgtactggtaccaacagagcctgga
ccagggcctccagttcctcattcagtattataatggagaagagagagcaaaaggaaacattcttgaacgattctccgcacaacagttcc
ctgacttgcactctgaactaaacctgagctctctggagctgggggactcagctttgtatttctgtgccagcagcgtag TRBV10-1:
atgggcacgaggctcttcttctatgtggcccttgtctgctgtgggcaggacacagggatgctgaaatcacccagagcccaagacaca
agatcacagagacaggaaggcaggtgaccttggcgtgtcaccagacttggaaccacaacaatatgttctggtatcgacaagacctgg
gacatgggctgaggctgatccattactcatatggtgttcaagacactaacaaaggagaagtctcagatggctacagtgtctctagatcaa
acacagaggacctcccccctcactctggagtctgctgcctcctcccagacatctgtatatttctgcgccagcagtgagtc TRBV10-2:
atgggcaccaggctcttcttctatgtggcccttgtctgctgtgggcaggacacagggatgctggaatcacccagagcccaagatacaa
gatcacagagacaggaaggcaggtgaccttgatgtgtcaccagacttggagccacagctatatgttctggtatcgacaagacctggga
catgggctgaggctgatctattactcagcagctgctgatattacagataaaggagaagtccccgatggctatgttgtctccagatccaag
acagagaatttccccctcactctggagtcagctacccgctcccagacatctgtatttctgcgccagcagtgagtc TRBV10-3:
atgggcacaaggttgttcttctatgtggcccttgtctcctgtggacaggacacatggatgctggaatcacccagagcccaagacacaa
ggtcacagagacaggaacaccagtgactctgagatgtcaccagactgagaaccaccgctatatgtactggtatcgacaagacccggg
gcatgggctgaggctgatccattactcatatggtgttaaagatactgacaaaggagaagtctcagatggctatagtgtctctagatcaaa
gacagaggatttcctcctcactctggagtccgctaccagctcccagacatctgtgtacttctgtgccatcagtgagtc

Figure 8g

TRBV11-1:
atgagcaccaggcttctctgctggatggccctctgtctcctgggggcagaactctcagaagctgaagttgcccagtcccccagatataa
gattacagagaaaagccaggctgtggcttttggtgtgatcctatttctggccatgctacccttactggtaccggcagatcctgggacag
ggcccggagcttctggttcaatttcaggatgagagtgtagtagatgattcacagttgcctaaggatcgattttctgcagagaggctcaaa
ggagtagactccactctcaagatccagcctgcagagcttggggactcggccatgtatctctgtgccagcagcttagc TRBV11-2:
atgggcaccaggctcctctgctgggcggccctctgtctcctgggagcagaactcacagaagctggagttgcccagtctcccagatata
agattatagagaaaaggcagagtgtggcttttggtgcaatcctatatctggccatgctacccttactggtaccagcagatcctgggaca
gggcccaaagcttctgattcagtttcagaataacggtgtagtggatgattcacagttgcctaaggatcgattttctgcagagaggctcaaa
ggagtagactccactctcaagatccagcctgcaaagcttgaggactcggccgtgtatctctgtgccagcagcttaga TRBV11-3:
atgggtaccaggctcctctgctgggtggccttctgtctcctggtggaagaactcatagaagctggagtggttcagtctcccagatataag
attatagagaaaaaacagcctgtggcttttggtgcaatcctatttctggccacaataccctttactggtacctgcagaacttgggacagg
gcccggagcttctgattcgatatgagaatgaggaagcagtagacgattcacagttgcctaaggatcgattttctgcagagaggctcaaa
ggagtagactccactctcaagatccagcctgcagagcttggggactcggccgtgtatctctgtgccagcagcttaga TRBV12-3:
atggactcctggaccttctgctgtgtgtccctttgcatcctggtagcgaagcatacagatgctggagttatccagtcaccccgccatgag
gtgacagagatgggacaagaagtgactctgagatgtaaaccaatttcaggccacaactccctttctggtacagacagaccatgatgcg
gggactggagttgctcatttactttaacaacaacgttccgatagatgattcagggatgcccgaggatcgattctcagctaagatgcctaat
gcatcattctccactctgaagatccagccctcagaacccagggactcagctgtgtacttctgtgccagcagtttagc TRBV12-4:
atggactcctggaccctctgctgtgtgtccctttgcatcctggtagcaaagcacacagatgctggagttatccagtcaccccggcacga
ggtgacagagatgggacaagaagtgactctgagatgtaaaccaatttcaggacacgactaccttttctggtacagacagaccatgatg
cggggactggagttgctcatttactttaacaacaacgttccgatagatgattcagggatgcccgaggatcgattctcagctaagatgcct
aatgcatcattctccactctgaagatccagccctcagaacccagggactcagctgtgtacttctgtgccagcagtttagc TRBV12-5:
atggccaccaggctcctctgctgtgtggttctttgtctcctgggagaagagcttatagatgctagagtcacccagacaccaaggcacaa
ggtgacagagatgggacaagaagtaacaatgagatgtcagccaatttaggccacaatactgttttctggtacagacagaccatgatgc
aaggactggagttgctggcttacttccgcaaccgggctcctctagatgattcggggatgccgaaggatcgattctcagcagagatgcct
gatgcaactttagccactctgaagatccagccctcagaacccagggactcagctgtgtatttttgtgctagtggtttggt

Figure 8h

TRBV13:
atgcttagtcctgacctgcctgactctgcctggaacaccaggctcctctgccatgtcatgctttgtctcctgggagcagtttcagtggctg
ctggagtcatccagtccccaagacatctgatcaaagaaaagagggaaacagccactctgaaatgctatcctatccctagacacgacac
tgtctactggtaccagcagggtccaggtcaggaccccagttcctcatttcgttttatgaaaagatgcagagcgataaaggaagcatcc
ctgatcgattctcagctcaacagttcagtgactatcattctgaactgaacatgagctccttggagctgggggactcagccctgtacttctgt
gccagcagcttagg TRBV14:
atggtttccaggcttctcagtttagtgtcccttttgtctcctgggagcaaagcacatagaagctggagttactcagttccccagccacagcg
taatagagaagggccagactgtgactctgagatgtgacccaatttctggacatgataatctttattggtatcgacgtgttatgggaaaaga
aataaaatttctgttacattttgtgaaagagtctaaacaggatgagtccggtatgcccaacaatcgattcttagctgaaaggactggaggg
acgtattctactctgaaggtgcagcctgcagaactggaggattctggagtttatttctgtgccagcagccaaga TRBV15:
atgggtcctgggcttctccactggatggcccctttgtctccttggaacaggtcatggggatgccatggtcatccagaacccaagatacca
ggttaccccagtttggaaaagccagtgaccctgagttgttctcagactttgaaccataacgtcatgtactggtaccagcagaagtcaagtca
ggccccaaagctgctgttccactactatgacaaagatttaacaatgaagcagacacccctgataacttccaatccaggaggccgaaca
cttctttctgctttcttgacatccgctcaccaggcctgggggacacagccatgtacctgtgtgccaccagcagaga TRBV16:
atgagcccaatattcacctgcatcacaatcctttgtctgctggctgcaggttctcctggtgaagaagtcgcccagactccaaaacatcttg
tcagaggggaaggacagaaagcaaaattatattgtgccccaataaaaggacacagttaggtttttttggtaccaacaggtcctgaaaaac
gagttcaagttcttgatttccttccagaatgaaaatgtctttgatgaaacaggtatgcccaaggaaagattttcagctaagtgcctcccaaa
ttcaccctgtagccttgagatccaggctacgaagcttgaggattcagcagtgtattttgtgccagcagccaatc TRBV17:
atggatatctggctcctctgctgggtgaccctgtgtctcttggcggcaggacactcggagcctggagtcagccagacccccagacaca
aggtcaccaacatgggacaggaggtgattctgaggtgcgatccatcttctggtcacatgtttgttcactggtaccgacagaatctgaggc
aagaaatgaagttgctgatttccttccagtaccaaaacattgcagttgattcagggatgcccaaggaacgattcacagctgaaagaccta
acggaacgtcttccacgctgaagatccatcccgcagagccgagggactcagccgtgtatctctacagtagcggtgg TRBV18:
atggacaccagagtactctgctgtgcggtcatctgtcttctgggggcaggtctctcaaatgccggcgtcatgcagaacccaagacacct
ggtcaggaggaggggacaggaggcaagactgagatgcagcccaatgaaaggacacagtcatgtttactggtatcggcagctccca
gaggaaggtctgaaattcatggtttatctccagaaagaaaatatcatagatgagtcaggaatgccaaaggaacgattttctgctgaatttc
ccaaagagggccccagcatcctgaggatccagcaggtagtgcgaggagattcggcagcttatttctgtgccagctcaccacc

Figure 8i

TRBV19:
atgagcaaccaggtgctctgctgtgtggtcctttgtttcctgggagcaaacaccgtggatggtggaatcactcagtccccaaagtacctg
ttcagaaaggaaggacagaatgtgaccctgagttgtgaacagaatttgaaccacgatgccatgtactggtaccgacaggacccaggg
caagggctgagattgatctactactcacagatagtaaatgactttcagaaaggagatatagctgaagggtacagcgtctctcgggagaa
gaaggaatcctttcctctcactgtgacatcggcccaaaagaacccgacagctttctatctctgtgccagtagtataga TRBV20-1:
atgctgctgcttctgctgcttctggggccaggctccgggcttggtgctgtcgtctctcaacatccgagctgggttatctgtaagagtggaa
cctctgtgaagatcgagtgccgttccctggactttcaggccacaactatgttttggtatcgtcagttcccgaaacagagtctcatgctgatg
gcaacttccaatgagggctccaaggccacatacgagcaaggcgtcgagaaggacaagtttctcatcaaccatgcaagcctgaccttgt
ccactctgacagtgaccagtgcccatcctgaagacagcagcttctacatctgcagtgctagaga TRBV23-1:
atgggcaccaggctcctcggctgtgcagccctgtgtctcctggcagcagactcttttcatgccaaagtcacacagactccaggacattt
ggtcaaaggaaaaggacagaaaacaaagatggattgtaccccgaaaaaggacatactttttgtttattggtatcaacagaatcagaata
aagagtttatgcttttgatttcctttcagaatgaacaagttcttcaagaaacggagatgcacaagaagcgattctcatctcaatgccccaag
aacgcaccctgcagcctggcaatcctgtcctcagaaccgggagacacggcactgtatctctgcgccagcagtcaatc TRBV24-1:
atggcctccctgctcttcttctgtggggccttttatctcctgggaacagggtccatggatgctgatgttacccagacccaaggaatagga
tcacaaagacaggaaagaggattatgctggaatgttctcagactaagggtcatgatagaatgtactggtatcgacaagacccaggact
gggcctacggttgatctattactcctttgatgtcaaagatataaacaaggagagatctctgatggatacagtgtctctcgacaggcaca
ggctaaattctccctgtccctagagtctgccatccccaaccagacagctctttacttctgtgccaccagtgatttg TRBV25-1:
atgactatcaggctcctctgctacatgggcttttattttctgggggcaggcctcatggaagctgacatctaccagacccaagataccttg
ttatagggacaggaaagaagatcactctggaatgttctcaaaccatgggccatgacaaaatgtactggtatcaacaagatccaggaatg
gaactacacctcatccactattcctatggagttaattccacagagaagggagatctttcctctgagtcaacagtctccagaataaggacg
gagcattttcccctgaccctggagtctgccaggccctcacatacctctcagtacctctgtgccagcagtgaata TRBV27:
atgggccccccagctccttggctatgtggtcctttgccttctaggagcaggcccctggaagcccaagtgacccagaacccaagatacc
tcatcacagtgactggaaagaagttaacagtgacttgttctcagaatatgaaccatgagtatatgtcctggtatcgacaagacccagggc
tgggcttaaggcagatctactattcaatgaatgttgaggtgactgataagggagatgttcctgaagggtacaaagtctctcgaaaagaga
agaggaatttcccctgatcctggagtcgcccagccccaaccagacctctctgtacttctgtgccagcagtttatc

Figure 8j

TRBV28:
atgggaatcaggctcctctgtcgtgtggccttttgtttcctggctgtaggcctcgtagatgtgaaagtaacccagagctcgagatatctag
tcaaaaggacgggagagaaagtttttctggaatgtgtccaggatatggaccatgaaaatatgttctggtatcgacaagacccaggtctg
gggctacggctgatctatttctcatatgatgttaaaatgaaagaaaaaggagatattcctgaggggtacagtgtctctagagagaagaag
gagcgcttctccctgattctggagtccgccagcaccaaccagacatctatgtacctctgtgccagcagtttatg TRBV29-1:
Atgctgagtcttctgctccttctcctgggactaggctctgtgttcagtgctgtcatctctcaaaagccaagcagggatatctgtcaacgtg
gaacctccctgacgatccagtgtcaagtcgatagccaagtcaccatgatgttctggtaccgtcagcaacctggacagagcctgacact
gatcgcaactgcaaatcagggctctgaggccacatatgagagtggatttgtcattgacaagtttcccatcagccgcccaaacctaacatt
ctcaactctgactgtgagcaacatgagccctgaagacagcagcatatatctctgcagcgttgaaga TRBV30:
atgctctgctctctccttgcccttctcctgggcactttctttggggtcagatctcagactattcatcaatggccagcgaccctggtgcagcct
gtgggcagcccgctctctctggagtgcactgtggagggaacatcaaaccccaacctatactggtaccgacaggctgcaggcagggg
cctccagctgctcttctactccgttggtattggccagatcagctctgaggtgccccagaatctctcagcctccagaccccaggaccggc
agttcatcctgagttctaagaagctccttctcagtgactctggcttctatctctgtgcctggagtgt

Figure 9a atgaaggaggtggagcagaattctggacccctcagtgttccagagggagccattgcct
ctctcaactgcacttacagtgaccgaggttcccagtccttcttctggtacagacaata
ttctgggaaaagccctgagttgataatgttcatatactccaatggtgacaaagaagat
ggaaggtttacagcacagctcaataaagccagccagtatgtttctctgctcatcagag
actcccagcccagtgattcagccacctacctctgtgccgtgaaggggggtctggggg
ttaccagaaagttacctttggaactggaacaaagctccaagtcatcccaaatatccag
aacccggatcctgccgtgtaccagctgagagactctaaatccagtgacaagtctgtct
gcctattcaccgattttgattctcaaacaaatgtgtcacaaagtaaggattctgatgt
gtatatcacagacaaatgtgtgctagacatgaggtctatggacttcaagagcaacagt
gctgtggcctggagcaacaaatctgactttgcatgtgcaaacgccttcaacaacagca
ttattccagaagacaccttcttccccagcccagaaagttcctaa

Figure 9b atgggcgtcatgcagaacccaagacacctggtcaggaggaggggacaggaggcaagac
tgagatgcagcccaatgaaaggacacagtcatgtttactggtatcggcagctcccaga
ggaaggtctgaaattcatggtttatctccagaaagaaaatatcatagatgagtcagga
atgccaaaggaacgattttctgctgaatttcccaaagagggccccagcatcctgagga
tccagcaggtagtgcgaggagattcggcagcttattctgtgccagctcaccacagac
aggggggcacagatacgcagtattttggcccaggcacccggctgacagtgctcgaggac
ctgaaaaacgtgttcccacccgaggtcgctgtgtttgagccatcagaagcagagatct
cccacacccaaaaggccacactggtgtgcctggccacaggcttctaccccgaccacgt
ggagctgagctggtgggtgaatgggaaggaggtgcacagtgggtctgcacagacccg
cagcccctcaaggagcagcccgccctcaatgactccagatacgctctgagcagccgcc
tgagggtctcggccaccttctggcaggaccccgcaaccacttccgctgtcaagtcca
gttctacgggctctcggagaatgacgagtggacccaggatagggccaaacccgtcacc
cagatcgtcagcgccgaggcctggggtagagcagactaa

Figure 10a

MKEVEQNSGPLSVPEGAIASLNCTYSDRGSQSFFWYRQYSGK
SPELIMFIYSNGDKEDGRFTAQLNKASQYVSLLIRDSQPSDSA
TYLCAVKGGSGGYQKVTFGTGTKLQVIPNIQNPDPAVYQLR
DSKSSDKSVCLFTDFDSQTNVSQSKDSDVYITDKCVLDMRSM
DFKSNSAVAWSNKSDFACANAFNNSIIPEDTFFPSPESS Stop

Figure 10b

MGVMQNPRHLVRRRGQEARLRCSPMKGHSHVYWYRQLPEE
GLKFMVYLQKENIIDESGMPKERFSAEFPKEGPSILRIQQVVR
GDSAAYFCASSPQTGGTDTQYFGPGTRLTVLEDLKNVFPPEV
AVFEPSEAEISHTQKATLVCLATGFYPDHVELSWWVNGKEV
HSGVCTDPQPLKEQPALNDSRYALSSRLRVSATFWQDPRNHF
RCQVQFYGLSENDEWTQDRAKPVTQIVSAEAWGRAD Stop

SEQUENCE LISTING

<160> NUMBER OF SEQ ID NOS: 149

<210> SEQ ID NO 1
<211> LENGTH: 30
<212> TYPE: PRT
<213> ORGANISM: Artificial Sequence

```
<220> FEATURE:
<223> OTHER INFORMATION: scTCR Linker

<400> SEQUENCE: 1

Pro Gly Gly Gly Ser Gly Gly Gly Ser Gly Gly Gly Ser Gly
1               5                   10                  15

Gly Gly Gly Ser Gly Gly Gly Ser Gly Gly Gly Pro
            20                  25                  30

<210> SEQ ID NO 2
<211> LENGTH: 20
<212> TYPE: PRT
<213> ORGANISM: Homo sapiens

<400> SEQUENCE: 2

Asp Ser Asp Val Tyr Ile Thr Asp Lys Thr Val Leu Asp Met Arg Ser
1               5                   10                  15

Met Asp Phe Lys
            20

<210> SEQ ID NO 3
<211> LENGTH: 20
<212> TYPE: PRT
<213> ORGANISM: Homo sapiens

<400> SEQUENCE: 3

Gln Ser Lys Asp Ser Asp Val Tyr Ile Thr Asp Lys Thr Val Leu Asp
1               5                   10                  15

Met Arg Ser Met
            20

<210> SEQ ID NO 4
<211> LENGTH: 20
<212> TYPE: PRT
<213> ORGANISM: Homo sapiens

<400> SEQUENCE: 4

Asp Ile Gln Asn Pro Asp Pro Ala Val Tyr Gln Leu Arg Asp Ser Lys
1               5                   10                  15

Ser Ser Asp Lys
            20

<210> SEQ ID NO 5
<211> LENGTH: 20
<212> TYPE: PRT
<213> ORGANISM: Homo sapiens

<400> SEQUENCE: 5

Asp Pro Ala Val Tyr Gln Leu Arg Asp Ser Lys Ser Ser Asp Lys Ser
1               5                   10                  15

Val Cys Leu Phe
            20

<210> SEQ ID NO 6
<211> LENGTH: 20
<212> TYPE: PRT
<213> ORGANISM: Homo sapiens

<400> SEQUENCE: 6

Asn Gly Lys Glu Val His Ser Gly Val Ser Thr Asp Pro Gln Pro Leu
1               5                   10                  15

Lys Glu Gln Pro
            20
```

```
<210> SEQ ID NO 7
<211> LENGTH: 20
<212> TYPE: PRT
<213> ORGANISM: Homo sapiens

<400> SEQUENCE: 7

Ala Leu Asn Asp Ser Arg Tyr Ala Leu Ser Ser Arg Leu Arg Val Ser
1               5                   10                  15

Ala Thr Phe Trp
            20

<210> SEQ ID NO 8
<211> LENGTH: 20
<212> TYPE: PRT
<213> ORGANISM: Homo sapiens

<400> SEQUENCE: 8

Pro Pro Glu Val Ala Val Phe Glu Pro Ser Glu Ala Glu Ile Ser His
1               5                   10                  15

Thr Gln Lys Ala
            20

<210> SEQ ID NO 9
<211> LENGTH: 20
<212> TYPE: PRT
<213> ORGANISM: Homo sapiens

<400> SEQUENCE: 9

Lys Glu Val His Ser Gly Val Ser Thr Asp Pro Gln Pro Leu Lys Glu
1               5                   10                  15

Gln Pro Ala Leu
            20

<210> SEQ ID NO 10
<211> LENGTH: 20
<212> TYPE: PRT
<213> ORGANISM: Homo sapiens

<400> SEQUENCE: 10

Val Phe Pro Pro Glu Val Ala Val Phe Glu Pro Ser Glu Ala Glu Ile
1               5                   10                  15

Ser His Thr Gln
            20

<210> SEQ ID NO 11
<211> LENGTH: 91
<212> TYPE: PRT
<213> ORGANISM: Mus musculus

<400> SEQUENCE: 11

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
                20                  25                  30

Ile Asn Val Pro Lys Thr Met Glu Ser Gly Thr Phe Ile Thr Asp Lys
            35                  40                  45

Thr Val Leu Asp Met Lys Ala Met Asp Ser Lys Ser Asn Gly Ala Ile
        50                  55                  60

Ala Trp Ser Asn Gln Thr Ser Phe Thr Cys Gln Asp Ile Phe Lys Glu
65                  70                  75                  80
```

Thr Asn Ala Thr Tyr Pro Ser Ser Asp Val Pro
                85                  90

<210> SEQ ID NO 12
<211> LENGTH: 126
<212> TYPE: PRT
<213> ORGANISM: Mus musculus

<400> SEQUENCE: 12

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Arg Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp
        115                 120                 125

<210> SEQ ID NO 13
<211> LENGTH: 20
<212> TYPE: PRT
<213> ORGANISM: Mus musculus

<400> SEQUENCE: 13

Glu Ser Gly Thr Phe Ile Thr Asp Lys Thr Val Leu Asp Met Lys Ala
1               5                   10                  15

Met Asp Ser Lys
            20

<210> SEQ ID NO 14
<211> LENGTH: 20
<212> TYPE: PRT
<213> ORGANISM: Mus musculus

<400> SEQUENCE: 14

Lys Thr Met Glu Ser Gly Thr Phe Ile Thr Asp Lys Thr Val Leu Asp
1               5                   10                  15

Met Lys Ala Met
            20

<210> SEQ ID NO 15
<211> LENGTH: 20
<212> TYPE: PRT
<213> ORGANISM: Mus musculus

<400> SEQUENCE: 15

Tyr Ile Gln Asn Pro Glu Pro Ala Val Tyr Gln Leu Lys Asp Pro Arg
1               5                   10                  15

Ser Gln Asp Ser
            20

<210> SEQ ID NO 16
<211> LENGTH: 20

```
<212> TYPE: PRT
<213> ORGANISM: Mus musculus

<400> SEQUENCE: 16

Ala Val Tyr Gln Leu Lys Asp Pro Arg Ser Gln Asp Ser Thr Leu Cys
1               5                   10                  15

Leu Phe Thr Asp
            20

<210> SEQ ID NO 17
<211> LENGTH: 20
<212> TYPE: PRT
<213> ORGANISM: Mus musculus

<400> SEQUENCE: 17

Asn Gly Arg Glu Val His Ser Gly Val Ser Thr Asp Pro Gln Ala Tyr
1               5                   10                  15

Lys Glu Ser Asn
            20

<210> SEQ ID NO 18
<211> LENGTH: 20
<212> TYPE: PRT
<213> ORGANISM: Mus musculus

<400> SEQUENCE: 18

Lys Glu Ser Asn Tyr Ser Tyr Cys Leu Ser Ser Arg Leu Arg Val Ser
1               5                   10                  15

Ala Thr Phe Trp
            20

<210> SEQ ID NO 19
<211> LENGTH: 20
<212> TYPE: PRT
<213> ORGANISM: Mus musculus

<400> SEQUENCE: 19

Pro Pro Lys Val Ser Leu Phe Glu Pro Ser Lys Ala Glu Ile Ala Asn
1               5                   10                  15

Lys Gln Lys Ala
            20

<210> SEQ ID NO 20
<211> LENGTH: 20
<212> TYPE: PRT
<213> ORGANISM: Mus musculus

<400> SEQUENCE: 20

Arg Glu Val His Ser Gly Val Ser Thr Asp Pro Gln Ala Tyr Lys Glu
1               5                   10                  15

Ser Asn Tyr Ser
            20

<210> SEQ ID NO 21
<211> LENGTH: 20
<212> TYPE: PRT
<213> ORGANISM: Mus musculus

<400> SEQUENCE: 21

Val Thr Pro Pro Lys Val Ser Leu Phe Glu Pro Ser Lys Ala Glu Ile
1               5                   10                  15

Ala Asn Lys Gln
            20
```

<210> SEQ ID NO 22
<211> LENGTH: 9
<212> TYPE: PRT
<213> ORGANISM: Mus musculus

<400> SEQUENCE: 22

Ala Ser Asn Glu Asn Met Asp Ala Met
1               5

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
cacagacaaa tgtgtgctag acat                                             24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
atgtctagca cacatttgtc tgtg                                             24

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cagtggggtc tgcacagacc c                                                21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
gggtctgtgc agaccccact g                                                21

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
atgatgaaat ccttgagagt ttt                                              23

<210> SEQ ID NO 28
<211> LENGTH: 20
<212> TYPE: DNA
<213> ORGANISM: Artificial Sequence
<220> FEATURE:
<223> OTHER INFORMATION: Primer

```
<400> SEQUENCE: 28
gtaagtgcag ttgagagagg                                          20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
atgagcatcg gcctcctgt                                           19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ttcatatcct gggcacactg                                          20

<210> SEQ ID NO 31
<211> LENGTH: 46
<212> TYPE: DNA
<213> ORGANISM: Artificial Sequence
<220> FEATURE:
<223> OTHER INFORMATION: Primer

<400> SEQUENCE: 31
tccccagccc agaaagttcc tctgatgtca agctggtcga gaaaag             46

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ttagctggac cacagccgca g                                        21

<210> SEQ ID NO 33
<211> LENGTH: 48
<212> TYPE: DNA
<213> ORGANISM: Artificial Sequence
<220> FEATURE:
<223> OTHER INFORMATION: Primer

<400> SEQUENCE: 33
ccgaggcctg gggtagagca gactctggct tcacctccga gtcttacc           48

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ttagcctctg gaatcctttc tc                                       22

<210> SEQ ID NO 35
<211> LENGTH: 621
<212> TYPE: DNA
```

```
<213> ORGANISM: Artificial Sequence
<220> FEATURE:
<223> OTHER INFORMATION: DNA encoding the alpha chain of a soluble
      disulfide-linked A6 TCR

<400> SEQUENCE: 35
atgcagaagg aagtggagca gaactctgga cccctcagtg ttccagaggg agccattgcc      60
tctctcaact gcacttacag tgaccgaggt tcccagtcct tcttctggta cagacaatat     120
tctgggaaaa gccctgagtt gataatgtcc atatactcca atggtgacaa agaagatgga     180
aggtttacag cacagctcaa taaagccagc cagtatgttt ctctgctcat cagagactcc     240
cagcccagtg attcagccac ctacctctgt gccgttacaa ctgacagctg ggggaaattg     300
cagtttggag cagggaccca ggttgtggtc accccagata tccagaaccc tgaccctgcc     360
gtgtaccagc tgagagactc taaatccagt gacaagtctg tctgcctatt caccgatttt     420
gattctcaaa caaatgtgtc acaaagtaag gattctgatg tgtatatcac agacaaatgt     480
gtgctagaca tgaggtctat ggacttcaag agcaacagtg ctgtggcctg agcaacaaa     540 tctgactttg catgtgcaaa cgccttcaac aacagcatta ttccagaaga caccttcttc     600
cccagcccag aaagttccta a                                                621

<210> SEQ ID NO 36
<211> LENGTH: 741
<212> TYPE: DNA
<213> ORGANISM: Artificial Sequence
<220> FEATURE:
<223> OTHER INFORMATION: DNA encoding the beta chain of a soluble
      disulfide-linked A6 TCR

<400> SEQUENCE: 36
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg ctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatcag aagcagagat ctcccacacc     420
caaaaggcca cactggtgtg cctggccaca gccttctacc ccgaccacgt ggagctgagc     480
tggtgggtga atgggaagga ggtgcacagt ggggtctgca cagacccgca gccccctcaag     540 gagcagcccg ccctcaatga ctccagatac gctctgagca gcgcctgag ggtctcggcc     600 accttctggc aggacccccg caaccacttc cgctgtcaag tccagttcta cgggctctcg     660
gagaatgacg agtggaccca ggataggggcc aaacccgtca cccagatcgt cagcgccgag     720
gcctggggta gagcagacta a                                                741

<210> SEQ ID NO 37
<211> LENGTH: 206
<212> TYPE: PRT
<213> ORGANISM: Artificial Sequence
<220> FEATURE:
<223> OTHER INFORMATION: Alpha chain of a soluble disulfide-linked A6
      TCR

<400> SEQUENCE: 37

Met Gln Lys Glu Val Glu Gln Asn Ser Gly Pro Leu Ser Val Pro Glu
 1               5                  10                  15
```

```
Gly Ala Ile Ala Ser Leu Asn Cys Thr Tyr Ser Asp Arg Gly Ser Gln
             20                  25                  30

Ser Phe Phe Trp Tyr Arg Gln Tyr Ser Gly Lys Ser Pro Glu Leu Ile
         35                  40                  45

Met Ser Ile Tyr Ser Asn Gly Asp Lys Glu Asp Gly Arg Phe Thr Ala
 50                  55                  60

Gln Leu Asn Lys Ala Ser Gln Tyr Val Ser Leu Leu Ile Arg Asp Ser
 65                  70                  75                  80

Gln Pro Ser Asp Ser Ala Thr Tyr Leu Cys Ala Val Thr Thr Asp Ser
                 85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
        130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
            195                 200                 205

<210> SEQ ID NO 38
<211> LENGTH: 246
<212> TYPE: PRT
<213> ORGANISM: Artificial Sequence
<220> FEATURE:
<223> OTHER INFORMATION: Beta chain of a soluble disulfide-linked A6 TCR

<400> SEQUENCE: 38

Met Asn Ala Gly Val Thr Gln Thr Pro Lys Phe Gln Val Leu Lys Thr
 1               5                  10                  15

Gly Gln Ser Met Thr Leu Gln Cys Ala Gln Asp Met Asn His Glu Tyr
             20                  25                  30

Met Ser Trp Tyr Arg Gln Asp Pro Gly Met Gly Leu Arg Leu Ile His
         35                  40                  45

Tyr Ser Val Gly Ala Gly Ile Thr Asp Gln Gly Glu Val Pro Asn Gly
 50                  55                  60

Tyr Asn Val Ser Arg Ser Thr Thr Glu Asp Phe Pro Leu Arg Leu Leu
 65                  70                  75                  80

Ser Ala Ala Pro Ser Gln Thr Ser Val Tyr Phe Cys Ala Ser Arg Pro
                 85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
        130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Ala Leu
```

```
                180                 185                 190
Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
        210                 215                 220

Trp Thr Gln Asp Arg Ala Lys Pro Val Thr Gln Ile Val Ser Ala Glu
225                 230                 235                 240

Ala Trp Gly Arg Ala Asp
            245

<210> SEQ ID NO 39
<211> LENGTH: 274
<212> TYPE: PRT
<213> ORGANISM: Artificial Sequence
<220> FEATURE:
<223> OTHER INFORMATION: Membrane-anchored A6 TCR alpha chain with
      introduced disulfide in terchain bond

<400> SEQUENCE: 39

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Thr Thr Asp Ser Trp Gly Lys Leu Gln Phe Gly Ala Gly Thr Gln
        115                 120                 125

Val Val Val Thr Pro Asp Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Ser Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 40
```

```
<211> LENGTH: 825
<212> TYPE: DNA
<213> ORGANISM: Artificial Sequence
<220> FEATURE:
<223> OTHER INFORMATION: DNA encoding membrane-anchored A6 TCR alpha
      chain with introduced disulfide interchain bond

<400> SEQUENCE: 40
atgatgaaat ccttgagagt tttactagtg atcctgtggc ttcagttgag ctgggtttgg      60
agccaacaga aggaagtgga gcagaactct ggacccctca gtgttccaga gggagccatt     120
gcctctctca actgcactta cagtgaccga ggttcccagt ccttcttctg gtacagacaa     180
tattctggga aaagccctga gttgataatg tccatatact ccaatggtga caaagaagat     240
ggaaggttta cagcacagct caataaagcc agccagtatg tttctctgct catcagagac     300
tcccagccca gtgattcagc cacctacctc tgtgccgtta caactgacag ctggggggaaa    360 ttgcagtttg gagcagggac ccaggttgtg gtcaccccag atatccagaa ccctgaccct     420
gccgtgtacc agctgagaga ctctaaatcc agtgacaagt ctgtctgcct attcaccgat     480
tttgattctc aaacaaatgt gtcacaaagt aaggattctg atgtgtatat cacagacaaa     540
tgtgtgctag acatgaggtc tatggacttc aagagcaaca gtgctgtggc ctggagcaac     600
aaatctgact ttgcatgtgc aaacgccttc aacaacagca ttattccaga agacaccttc     660
ttccccagcc cagaaagttc ctctgatgtc aagctggtcg agaaaagctt tgaaacagat     720
acgaacctaa actttcaaaa cctgtcagtg attgggttcc gaatcctcct cctgaaagtg     780
gccgggttta atctgctcat gacgctgcgg ctgtggtcca gctaa                    825

<210> SEQ ID NO 41
<211> LENGTH: 313
<212> TYPE: PRT
<213> ORGANISM: Artificial Sequence
<220> FEATURE:
<223> OTHER INFORMATION: Membrane-anchored A6 TCR beta chain with
      introduced disulfide interchain bond

<400> SEQUENCE: 41

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Arg Pro Gly Leu Ala Gly Gly Arg Pro Glu Gln Tyr Phe Gly Pro Gly
        115                 120                 125

Thr Arg Leu Thr Val Thr Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175
```

Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asp Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Ser Gly Phe Thr Ser Glu Ser Tyr
        260                 265                 270

Gln Gln Gly Val Leu Ser Ala Thr Ile Leu Tyr Glu Ile Leu Leu Gly
    275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310

<210> SEQ ID NO 42
<211> LENGTH: 942
<212> TYPE: DNA
<213> ORGANISM: Artificial Sequence
<220> FEATURE:
<223> OTHER INFORMATION: DNA encoding membrane-anchored A6 TCR beta
      chain with introduced disulfide interchain bond

<400> SEQUENCE: 42
atgagcatcg gcctcctgtg ctgtgcagcc ttgtctctcc tgtgggcagg tccagtgaac     60
gctggtgtca ctcagacccc aaaattccag gtcctgaaga caggacagag catgacactg    120
cagtgtgccc aggatatgaa ccatgaatac atgtcctggt atcgacaaga cccaggcatg    180
gggctgaggc tgattcatta ctcagttggt gctggtatca ctgaccaagg agaagtcccc    240
aatggctaca atgtctccag atcaaccaca gaggatttcc cgctcaggct gctgtcggct    300
gctccctccc agacatctgt gtacttctgt gccagcaggc cgggactagc gggagggcga    360
ccagagcagt acttcgggcc gggcaccagg ctcacggtca cagaggacct gaaaaacgtg    420
ttcccacccg aggtcgctgt gtttgagcca tcagaagcag agatctccca cacccaaaag    480
gccacactgg tgtgcctggc cacaggcttc taccccgacc acgtggagct gagctggtgg    540
gtgaatggga aggaggtgca cagtggggtc tgcacagacc cgcagcccct caaggagcag    600
cccgccctca tgactccaga atactgcctg agcagccgcc tgagggtctc ggccaccttc    660
tggcaggacc ccgcaaccca cttccgctgt caagtccagt tctacgggct ctcggagaat    720
gacgagtgga cccaggatag gccaaaaccc gtcacccaga tcgtcagcgc cgaggcctgg    780
ggtagagcag actctggctt cacctccgag tcttaccagc aagggtcct gtctgccacc    840
atcctctatg agatcttgct agggaaggcc accttgtatg ccgtgctggt cagtgccctc    900
gtgctgatgg ccatggtaaa gagaaaggat tccagaggct aa                       942

<210> SEQ ID NO 43
<211> LENGTH: 425
<212> TYPE: DNA
<213> ORGANISM: Homo sapiens

<400> SEQUENCE: 43
atatccagaa ccctgaccct gccgtgtacc agctgagaga ctctaaatcc agtgacaagt     60

```
ctgtctgcct attcaccgat tttgattctc aaacaaatgt gtcacaaagt aaggattctg    120
atgtgtatat cacagacaaa actgtgctag acatgaggtc tatggacttc aagagcaaca    180
gtgctgtggc ctggagcaac aaatctgact ttgcatgtgc aaacgccttc aacaacagca    240
ttattccaga agacaccttc ttccccagcc cagaaagttc ctgtgatgtc aagctggtcg    300
agaaaagctt tgaaacagat acgaacctaa actttcaaaa cctgtcagtg attgggttcc    360
gaatcctcct cctgaaagtg gccgggttta atctgctcat gacgctgcgg ctgtggtcca    420
gctga                                                                425

<210> SEQ ID NO 44
<211> LENGTH: 326
<212> TYPE: DNA
<213> ORGANISM: Homo sapiens

<400> SEQUENCE: 44
atgtggggag ctttccttct ctatgtttcc atgaagatgg gaggcactgc aggacaaagc     60
cttgagcagc cctctgaagt gacagctgtg gaaggagcca ttgtccagat aaactgcacg    120
taccagacat ctgggtttta tgggctgtcc tggtaccagc aacatgatgg cggagcaccc    180
acatttcttt cttacaatgc tctggatggt ttggaggaga caggtcgttt tcttcattc     240 cttagtcgct ctgatagtta tggttacctc cttctacagg agctccagat gaaagactct    300
gcctcttact tctgcgctgt gagaga                                         326

<210> SEQ ID NO 45
<211> LENGTH: 326
<212> TYPE: DNA
<213> ORGANISM: Homo sapiens

<400> SEQUENCE: 45
atgtggggag ttttccttct ttatgtttcc atgaagatgg gaggcactac aggacaaaac     60
attgaccagc ccactgagat gacagctacg gaaggtgcca ttgtccagat caactgcacg    120
taccagacat ctgggttcaa cgggctgttc tggtaccagc aacatgctgg cgaagcaccc    180
acatttctgt cttacaatgt tctggatggt ttggaggaga aggtcgtttt tcttcattc     240 cttagtcggt ctaaagggta cagttacctc cttttgaagg agctccagat gaaagactct    300
gcctcttacc tctgtgctgt gagaga                                         326

<210> SEQ ID NO 46
<211> LENGTH: 338
<212> TYPE: DNA
<213> ORGANISM: Homo sapiens

<400> SEQUENCE: 46
atggctttgc agagcactct gggggcggtg tggctagggc ttctcctcaa ctctctctgg     60
aaggttgcag aaagcaagga ccaagtgttt cagccttcca cagtggcatc ttcagaggga    120
gctgtggtgg aaatcttctg taatcactct gtgtccaatg cttacaactt cttctggtac    180
cttcacttcc cggatgtgc accaagactc cttgttaaag ctcaaagcc ttctcagcag     240 ggacgataca acatgaccta tgaacggttc tcttcatcgc tgctcatcct ccaggtgcgg    300
gaggcagatg ctgctgttta ctactgtgct gtggagga                            338

<210> SEQ ID NO 47
<211> LENGTH: 343
<212> TYPE: DNA
<213> ORGANISM: Homo sapiens
```

<400> SEQUENCE: 47

```
atggcctctg cacccatctc gatgcttgcg atgctcttca cattgagtgg gctgagagct      60
cagtcagtgg ctcagccgga agatcaggtc aacgttgctg aagggaatcc tctgactgtg     120
aaatgcacct attcagtctc tggaaaccct tatcttttt ggtatgttca ataccccaac      180
cgaggcctcc agttccttct gaaatacatc acaggggata acctggttaa aggcagctat     240
ggctttgaag ctgaatttaa caagagccaa acctccttcc acctgaagaa accatctgcc     300
cttgtgagcg actccgcttt gtacttctgt gctgtgagag aca                       343
```

<210> SEQ ID NO 48
<211> LENGTH: 328
<212> TYPE: DNA
<213> ORGANISM: Homo sapiens

<400> SEQUENCE: 48

```
atgaggcaag tggcgagagt gatcgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga     180
ccacgattta ttattcaagg atacaagaca aaagttacaa cgaagtggc ctccctgttt      240
atccctgccg acagaaagtc cagcactctg agcctgcccc gggtttccct gagcgacact     300
gctgtgtact actgcctcgt gggtgaca                                        328
```

<210> SEQ ID NO 49
<211> LENGTH: 340
<212> TYPE: DNA
<213> ORGANISM: Homo sapiens

<400> SEQUENCE: 49

```
atgaagacat ttgctggatt ttcgttcctg ttttttgtggc tgcagctgga ctgtatgagt      60
agaggagagg atgtggagca gagtcttttc ctgagtgtcc gagagggaga cagctccgtt     120
ataaactgca cttacacaga cagctcctcc acctacttat actggtataa gcaagaacct     180
ggagcaggtc tccagttgct gacgtatatt ttttcaaata tggacatgaa acaagaccaa     240
agactcactg ttctattgaa taaaaaggat aaacatctgt ctctgcgcat tgcagacacc     300
cagactgggg actcagctat ctacttctgt gcagagagta                           340
```

<210> SEQ ID NO 50
<211> LENGTH: 340
<212> TYPE: DNA
<213> ORGANISM: Homo sapiens

<400> SEQUENCE: 50

```
atggagtcat tcctgggagg tgttttgctg attttgtggc ttcaagtgga ctgggtgaag      60
agccaaaaga tagaacagaa ttccgaggcc ctgaacattc aggagggtaa aacggccacc     120
ctgacctgca ctatacaaa ctattcccca gcatacttac agtggtaccg acaagatcca      180
ggaagaggcc ctgttttctt gctactcata cgtgaaaatg agaaagaaaa aaggaaagaa     240
agactgaagg tcacctttga taccaccctt aaacagagtt tgtttcatat cacagcctcc     300
cagcctgcag actcagctac ctacctctgt gctctagaca                           340
```

<210> SEQ ID NO 51
<211> LENGTH: 337
<212> TYPE: DNA
<213> ORGANISM: Homo sapiens
```

<400> SEQUENCE: 51

```
atggagaaga tgcggagacc tgtcctaatt atattttgtc tatgtcttgg ctgggcaaat        60
ggagaaaacc aggtggagca cagccctcat tttctgggac cccagcaggg agacgttgcc       120
tccatgagct gcacgtactc tgtcagtcgt tttaacaatt gcagtggta caggcaaaat        180
acagggatgg gtcccaaaca cctattatcc atgtattcag ctggatatga aagcagaaa        240
ggaagactaa atgctacatt actgaagaat ggaagcagct tgtacattac agccgtgcag       300
cctgaagatt cagccaccta tttctgtgct gtagatg                                337
```

<210> SEQ ID NO 52
<211> LENGTH: 341
<212> TYPE: DNA
<213> ORGANISM: Homo sapiens

<400> SEQUENCE: 52

```
atgctcctgt tgctcatacc agtgctgggg atgattttg ccctgagaga tgccagagcc         60
cagtctgtga gccagcataa ccaccacgta attctctctg aagcagcctc actggagttg       120
ggatgcaact attcctatgg tggaactgtt aatctcttct ggtatgtcca gtaccctggt       180
caacaccttc agcttctcct caagtacttt tcaggggatc cactggttaa aggcatcaag       240
ggctttgagg ctgaatttat aaagagtaaa ttctcccttta atctgaggaa accctctgtg       300
cagtggagtg acacagctga gtacttctgt gccgtgaatg c                           341
```

<210> SEQ ID NO 53
<211> LENGTH: 341
<212> TYPE: DNA
<213> ORGANISM: Homo sapiens

<400> SEQUENCE: 53

```
atgctcctgc tgctcgtccc agtgctcgag gtgattttta ctctgggagg aaccagagcc        60
cagtcggtga cccagcttga cagccacgtc tctgtctctg aaggaacccc ggtgctgctg       120
aggtgcaact actcatcttc ttattccacca tctctcttct ggtatgtgca acaccccaac      180
aaaggactcc agcttctcct gaagtacaca tcagcggcca cctggttaa aggcatcaac        240
ggttttgagg ctgaatttaa gaagagtgaa acctccttcc acctgacgaa accctcagcc       300
catatgagcg acgcggctga gtacttctgt gttgtgagtg a                           341
```

<210> SEQ ID NO 54
<211> LENGTH: 341
<212> TYPE: DNA
<213> ORGANISM: Homo sapiens

<400> SEQUENCE: 54

```
atgctcctgg agcttatccc actgctgggg atacattttg tcctgagaac tgccagagcc        60
cagtcagtga cccagcctga catccacatc actgtctctg aaggagcctc actggagttg       120
agatgtaact attcctatgg ggcaacacct tatctcttct ggtatgtcca gtcccccggc       180
caaggcctcc agctgctcct gaagtacttt tcaggagaca ctctggttca aggcattaaa       240
ggctttgagg ctgaatttaa gaggagtcaa tcttccttca atctgaggaa accctctgtg       300
cattggagtg atgctgctga gtacttctgt gctgtgggtg c                           341
```

<210> SEQ ID NO 55
<211> LENGTH: 341
<212> TYPE: DNA
<213> ORGANISM: Homo sapiens

```
<400> SEQUENCE: 55
atgctcctgc tgctcgtccc agtgctcgag gtgattttta ccctgggagg aaccagagcc      60
cagtcggtga cccagcttgg cagccacgtc tctgtctctg aaggagccct ggttctgctg     120
aggtgcaact actcatcgtc tgttccacca tatctcttct ggtatgtgca ataccccaac     180
caaggactcc agcttctcct gaagtacaca tcagcggcca ccctggttaa aggcatcaac     240
ggttttgagg ctgaatttaa aagagtgaa acctccttcc acctgacgaa accctcagcc     300
catatgagcg acgcggctga gtacttctgt gctgtgagtg a                         341

<210> SEQ ID NO 56
<211> LENGTH: 341
<212> TYPE: DNA
<213> ORGANISM: Homo sapiens

<400> SEQUENCE: 56
atgctcctgc tgctcgtccc agcgttccag gtgattttta ccctgggagg aaccagagcc      60
cagtctgtga cccagcttga cagccaagtc cctgtctttg aagaagcccc tgtggagctg     120
aggtgcaact actcatcgtc tgtttcagtg tatctcttct ggtatgtgca ataccccaac     180
caaggactcc agcttctcct gaagtattta tcaggatcca ccctggttaa aggcatcaac     240
ggttttgagg ctgaatttaa caagagtcaa acttccttcc acttgaggaa accctcagtc     300
catataagcg acacggctga gtacttctgt gctgtgagtg a                         341

<210> SEQ ID NO 57
<211> LENGTH: 347
<212> TYPE: DNA
<213> ORGANISM: Homo sapiens

<400> SEQUENCE: 57
atgctcttag tggtcattct gctgcttgga atgttcttca cactgagagg aaccagaacc      60
cagtcggtga cccagcttga tggccacatc actgtctctg aagaagcccc tctggaactg     120
aagtgcaact attcctatag tggagttcct tctctcttct ggtatgtcca atactctagc     180
caaagcctcc agcttctcct caaagaccta acagaggcca cccaggttaa aggcatcaga     240
ggttttgagg ctgaatttaa aagagcgaa acctccttct acctgaggaa accatcaacc     300
catgtgagtg atgctgctga gtacttctgt gctgtgggtg acaggag                   347

<210> SEQ ID NO 58
<211> LENGTH: 338
<212> TYPE: DNA
<213> ORGANISM: Homo sapiens

<400> SEQUENCE: 58
atgaattctt ctccaggacc agcgattgca ctattcttaa tgtttggggg aatcaatgga      60
gattcagtgg tccagacaga aggccaagtg ctcccctctg aagggattc cctgattgtg     120 aactgctcct atgaaaccac acagtaccct tccctttttt ggtatgtcca atatcctgga     180
gaaggtccac agctccacct gaaagccatg aaggccaatg acaagggaag gaacaaaggt     240
tttgaagcca tgtaccgtaa agaaaccact tctttccact ggagaaaga ctcagttcaa     300 gagtcagact ccgctgtgta cttctgtgct ctgagtga                             338

<210> SEQ ID NO 59
<211> LENGTH: 338
<212> TYPE: DNA
<213> ORGANISM: Homo sapiens
```

<400> SEQUENCE: 59

```
atgaactatt ctccaggctt agtatctctg atactcttac tgcttggaag aacccgtgga    60
aattcagtga cccagatgga agggccagtg actctctcag aagaggcctt cctgactata   120
aactgcacgt acacagccac aggataccct tccctttcct ggtatgtcca atatcctgga   180
gaaggtctac agctcctcct gaaagccacg aaggctgatg acaagggaag caacaaaggt   240
tttgaagcca cataccgtaa agaaaccact tctttccact tggagaaagg ctcagttcaa   300
gtgtcagact cagcggtgta cttctgtgct ctgagtga                           338
```

<210> SEQ ID NO 60
<211> LENGTH: 343
<212> TYPE: DNA
<213> ORGANISM: Homo sapiens

<400> SEQUENCE: 60

```
atgaaaaagc atctgacgac cttcttggtg attttgtggc tttattttta tagggggaat    60
ggcaaaaacc aagtggagca gagtcctcag tccctgatca tcctggaggg aaagaactgc   120
actcttcaat gcaattatac agtgagcccc ttcagcaact taaggtggta taagcaagat   180
actgggagag gtcctgtttc cctgacaatc atgactttca gtgagaacac aaagtcgaac   240
ggaagatata cagcaactct ggatgcagac acaaagcaaa gctctctgca catcacagcc   300
tcccagctca gcgattcagc tcctacatc tgtgtggtga gcg                       343
```

<210> SEQ ID NO 61
<211> LENGTH: 337
<212> TYPE: DNA
<213> ORGANISM: Homo sapiens

<400> SEQUENCE: 61

```
atgatatcct tgagagtttt actggtgatc ctgtggcttc agttaagctg ggtttggagc    60
caacggaagg aggtggagca ggatcctgga cccttcaatg ttccagaggg agccactgtc   120
gctttcaact gtacttacag caacagtgct tctcagtctt tcttctggta cagacaggat   180
tgcaggaaag aacctaagtt gctgatgtcc gtatactcca gtggtaatga agatggaagg   240
tttacagcac agctcaatag agccagccag tatatttccc tgctcatcag agactccaag   300
ctcagtgatt cagccaccta cctctgtgtg gtgaaca                             337
```

<210> SEQ ID NO 62
<211> LENGTH: 343
<212> TYPE: DNA
<213> ORGANISM: Homo sapiens

<400> SEQUENCE: 62

```
atgatgaaat ccttgagagt tttactagtg atcctgtggc ttcagttgag ctgggtttgg    60
agccaacaga aggaggtgga gcagaattct ggacccctca gtgttccaga gggagccatt   120
gcctctctca actgcactta cagtgaccga ggttcccagt ccttcttctg gtacagacaa   180
tattctggga aaagccctga gttgataatg ttcatatact ccaatggtga caaagaagat   240
ggaaggttta cagcacagct caataaagcc agccagtatg tttctctgct catcagagac   300
tcccagccca gtgattcagc cacctacctc tgtgccgtga aca                      343
```

<210> SEQ ID NO 63
<211> LENGTH: 343
<212> TYPE: DNA
<213> ORGANISM: Homo sapiens -continued

<400> SEQUENCE: 63

```
atgatgaaat ccttgagagt tttactggtg atcctgtggc ttcagttaag ctgggtttgg      60
agccaacaga aggaggtgga gcaggatcct ggaccactca gtgttccaga gggagccatt    120
gtttctctca actgcactta cagcaacagt gcttttcaat acttcatgtg gtacagacag    180
tattccagaa aaggccctga gttgctgatg tacacatact ccagtggtaa caaagaagat    240
ggaaggttta cagcacaggt cgataaatcc agcaagtata tctccttgtt catcagagac    300
tcacagccca gtgattcagc cacctacctc tgtgcaatga gcg                      343
```

<210> SEQ ID NO 64
<211> LENGTH: 337
<212> TYPE: DNA
<213> ORGANISM: Homo sapiens

<400> SEQUENCE: 64

```
atgacatcca ttcgagctgt atttatattc ctgtggctgc agctggactt ggtgaatgga      60
gagaatgtgg agcagcatcc ttcaaccctg agtgtccagg agggagacag cgctgttatc    120
aagtgtactt attcagacag tgcctcaaac tacttccctt ggtataagca agaacttgga    180
aaaggacctc agcttattat agacattcgt tcaaatgtgg gcgaaaagaa agaccaacga    240
attgctgtta cattgaacaa gacagccaaa catttctccc tgcacatcac agagacccaa    300
cctgaagact cggctgtcta cttctgtgca gcaagta                             337
```

<210> SEQ ID NO 65
<211> LENGTH: 340
<212> TYPE: DNA
<213> ORGANISM: Homo sapiens

<400> SEQUENCE: 65

```
atggcaggca ttcgagcttt atttatgtac ttgtggctgc agctggactg ggtgagcaga      60
ggagagagtg tggggctgca tcttcctacc ctgagtgtcc aggagggtga caactctatt    120
atcaactgtg cttattcaaa cagcgcctca gactacttca tttggtacaa gcaagaatct    180
ggaaaaggtc tcaattcat tatagacatt cgttcaaata tggacaaaag gcaaggccaa    240
agagtcaccg ttttattgaa taagacagtg aaacatctct ctctgcaaat tgcagctact    300
caacctggag actcagctgt ctactttgt gcagagaata                           340
```

<210> SEQ ID NO 66
<211> LENGTH: 350
<212> TYPE: DNA
<213> ORGANISM: Homo sapiens

<400> SEQUENCE: 66

```
atgtcacttt ctagcctgct gaaggtggtc acagcttcac tgtggctagg acctggcatt      60
gcccagaaga taactcaaac ccaaccagga atgttcgtgc aggaaaagga ggctgtgact    120
ctggactgca catatgacac cagtgatcaa agttatggtc tattctggta caagcagccc    180
agcagtgggg aaatgatttt tcttatttat caggggtctt atgacgagca aaatgcaaca    240
gaaggtcgct actcattgaa tttccagaag gcaagaaaat ccgccaacct tgtcatctcc    300
gcttcacaac tggggactc agcaatgtat ttctgtgcaa tgagagaggg                350
```

<210> SEQ ID NO 67
<211> LENGTH: 329
<212> TYPE: DNA
<213> ORGANISM: Homo sapiens

<400> SEQUENCE: 67

```
atgaagccca ccctcatctc agtgcttgtg ataatattta tactcagagg aacaagagcc      60
cagagagtga ctcagcccga gaagctcctc tctgtcttta aggggcccc agtggagctg      120 aagtgcaact attcctattc tgggagtcct gaactcttct ggtatgtcca gtactccaga      180
caacgcctcc agttactctt gagacacatc tctagagaga gcatcaaagg cttcactgct      240
gaccttaaca aaggcgagac atctttccac ctgaagaaac catttgctca gaggaagac      300 tcagccatgt attactgtgc tctaagtgg                                        329
```

<210> SEQ ID NO 68
<211> LENGTH: 337
<212> TYPE: DNA
<213> ORGANISM: Homo sapiens

<400> SEQUENCE: 68

```
atggaaactc tcctgggagt gtctttggtg attctatggc ttcaactggc tagggtgaac      60
agtcaacagg gagaagagga tcctcaggcc ttgagcatcc aggagggtga aaatgccacc      120
atgaactgca gttacaaaac tagtataaac aatttacagt ggtatagaca aaattcaggt      180
agaggccttg tccacctaat tttaatacgt tcaaatgaaa gagagaaaca cagtggaaga      240
ttaagagtca cgcttgacac ttccaagaaa agcagttcct tgttgatcac ggcttcccgg      300
gcagcagaca ctgcttctta cttctgtgct acggacg                               337
```

<210> SEQ ID NO 69
<211> LENGTH: 335
<212> TYPE: DNA
<213> ORGANISM: Homo sapiens

<400> SEQUENCE: 69

```
atgctgtctg cttcctgctc aggacttgtg atcttgttga tattcagaag gaccagtgga      60
gactcggtta cccagacaga aggcccagtt accctccctg agagggcagc tctgacatta      120
aactgcactt atcagtccag ctattcaact tttctattct ggtatgtcca gtatctaaac      180
aaagagcctg agctcctcct gaaaagttca gaaaaccagg agacggacag cagaggtttt      240
caggccagtc ctatcaagag tgacagttcc ttccacctgg agaagccctc ggtgcagctg      300
tcggactctg ccgtgtacta ctgcgctctg agaga                                 335
```

<210> SEQ ID NO 70
<211> LENGTH: 350
<212> TYPE: DNA
<213> ORGANISM: Homo sapiens

<400> SEQUENCE: 70

```
atgctgactg ccagcctgtt gagggcagtc atagcctcca tctgtgttgt atccagcatg      60
gctcagaagg taactcaagc gcagactgaa atttctgtgg tggagaagga ggatgtgacc      120
ttggactgtg tgtatgaaac ccgtgatact acttattact tattctgtgta caagcaacca      180 ccaagtggag aattggtttt ccttattcgt cggaactctt ttgatgagca aaatgaaata      240
agtggtcggt attcttggaa cttccagaaa tccaccagtt ccttcaactt caccatcaca      300
gcctcacaag tcgtggactc agcagtatac ttctgtgctc tgagtgaggc                 350
```

<210> SEQ ID NO 71
<211> LENGTH: 337
<212> TYPE: DNA
<213> ORGANISM: Homo sapiens

<400> SEQUENCE: 71

```
atggagaaaa tgttggagtg tgcattcata gtcttgtggc ttcagcttgg ctggttgagt      60
ggagaagacc aggtgacgca gagtcccgag gccctgagac tccaggaggg agagagtagc     120
agtcttaact gcagttacac agtcagcggt ttaagagggc tgttctggta taggcaagat    180
cctgggaaag gccctgaatt cctcttcacc ctgtattcag ctggggaaga aaaggagaaa    240
gaaaggctaa agccacatt aacaaagaag gaaagctttc tgcacatcac agcccctaaa    300
cctgaagact cagccactta tctctgtgct gtgcagg                              337
```

<210> SEQ ID NO 72
<211> LENGTH: 336
<212> TYPE: DNA
<213> ORGANISM: Homo sapiens

<400> SEQUENCE: 72

```
atggagaccc tcttgggcct gcttatcctt tggctgcagc tgcaatgggt gagcagcaaa     60
caggaggtga cgcagattcc tgcagctctg agtgtcccag aaggagaaaa cttggttctc    120
aactgcagtt tcactgatag cgctatttac aacctccagt ggtttaggca ggaccctggg    180
aaaggtctca catctctgtt gcttattcag tcaagtcaga gagcaaac aagtggaaga      240 cttaatgcct cgctggataa atcatcagga cgtagtactt tatacattgc agcttctcag    300
cctggtgact cagccaccta cctctgtgct gtgagg                               336
```

<210> SEQ ID NO 73
<211> LENGTH: 331
<212> TYPE: DNA
<213> ORGANISM: Homo sapiens

<400> SEQUENCE: 73

```
atgaagagga tattgggagc tctgctgggg ctcttgagtg cccaggtttg ctgtgtgaga     60
ggaatacaag tggagcagag tcctccagac ctgattctcc aggagggagc caattccacg    120
ctgcggtgca tttttctga ctctgtgaac aatttgcagt ggtttcatca aaacccttgg     180
ggacagctca tcaacctgtt ttacattccc tcagggacaa aacagaatgg aagattaagc    240
gccacgactg tcgctacgga acgctacagc ttattgtaca tttcctcttc ccagaccaca    300
gactcaggcg tttatttctg tgctgtggag c                                    331
```

<210> SEQ ID NO 74
<211> LENGTH: 364
<212> TYPE: DNA
<213> ORGANISM: Homo sapiens

<400> SEQUENCE: 74

```
atggacaaga tcttaggagc atcatttta gttctgtggc ttcaactatg ctgggtgagt      60
ggccaacaga aggagaaaag tgaccagcag caggtgaaac aaagtcctca atctttgata    120
gtccagaaag gagggatttc aattataaac tgtgcttatg agaacactgc gtttgactac    180
tttccatggt accaacaatt ccctgggaaa ggccctgcat tattgatagc catacgtcca    240
gatgtgagtg aaaagaaga aggaagattc acaatctcct tcaataaaag tgccaagcag    300
ttctcattgc atatcatgga ttcccagcct ggagactcag ccacctactt ctgtgcagca    360
agca                                                                  364
```

<210> SEQ ID NO 75
<211> LENGTH: 343

<210> SEQ ID NO 75
<211> LENGTH: 343
<212> TYPE: DNA
<213> ORGANISM: Homo sapiens

<400> SEQUENCE: 75

```
atggagaaga atcctttggc agccccatta ctaatcctct ggtttcatct tgactgcgtg      60
agcagcatac tgaacgtgga acaaagtcct cagtcactgc atgttcagga gggagacagc     120
accaatttca cctgcagctt cccttccagc aattttttatg ccttacactg gtacagatgg    180
gaaactgcaa aaagccccga ggccttgttt gtaatgactt taaatgggga tgaaaagaag     240
aaaggacgaa taagtgccac tcttaatacc aaggagggtt acagctattt gtacatcaaa     300
ggatcccagc ctgaagactc agccacatac ctctgtgcct tta                       343
```

<210> SEQ ID NO 76
<211> LENGTH: 327
<212> TYPE: DNA
<213> ORGANISM: Homo sapiens

<400> SEQUENCE: 76

```
atgctactca tcacatcaat gttggtctta tggatgcaat tgtcacaggt gaatggacaa      60
caggtaatgc aaattcctca gtaccagcat gtacaagaag gagaggactt caccacgtac     120
tgcaattcct caactacttt aagcaatata cagtggtata agcaaaggcc tggtggacat     180
cccgtttttt tgatacagtt agtgaagagt ggagaagtga agaagcagaa aagactgaca     240
tttcagtttg gagaagcaaa aagaacagc tccctgcaca tcacagccac ccagactaca      300
gatgtaggaa cctacttctg tgcaggg                                          327
```

<210> SEQ ID NO 77
<211> LENGTH: 328
<212> TYPE: DNA
<213> ORGANISM: Homo sapiens

<400> SEQUENCE: 77

```
atgaggctgg tggcaagagt aactgtgttt ctgacctttg gaactataat tgatgctaag      60
accacccagc cccctccat ggattgcgct gaaggaagag ctgcaaacct gccttgtaat      120
cactctacca tcagtggaaa tgagtatgtg tattggtatc gacagattca ctcccagggg     180
ccacagtata tcattcatgg tctaaaaaac aatgaaacca atgaaatggc ctctctgatc     240
atcacagaag acagaaagtc cagcaccttg atcctgcccc acgctacgct gagagacact     300
gctgtgtact attgcatcgt cagagtcg                                         328
```

<210> SEQ ID NO 78
<211> LENGTH: 327
<212> TYPE: DNA
<213> ORGANISM: Homo sapiens

<400> SEQUENCE: 78

```
atgaagttgg tgacaagcat tactgtactc ctatctttgg gtattatggg tgatgctaag      60
accacacagc caaattcaat ggagagtaac gaagaagagc tgttcactt gccttgtaac      120
cactccacaa tcagtggaac tgattacata cattggtatc gacagcttcc ctcccagggt     180
ccagagtacg tgattcatgg tcttacaagc aatgtgaaca acagaatggc ctctctggca     240
atcgctgaag acagaaagtc cagtaccttg atcctgcacc gtgctacctt gagagatgct     300
gctgtgtact actgcatcct gagagac                                          327
```

<210> SEQ ID NO 79
<211> LENGTH: 328

```
<212> TYPE: DNA
<213> ORGANISM: Homo sapiens

<400> SEQUENCE: 79
atggtcctga aattctccgt gtccattctt tggattcagt tggcatgggt gagcacccag      60
ctgctggagc agagccctca gtttctaagc atccaagagg gagaaaatct cactgtgtac     120
tgcaactcct caagtgtttt ttccagctta caatggtaca gacaggagcc tggggaaggt     180
cctgtcctcc tggtgacagt agttacgggt ggagaagtga agaagctgaa gagactaacc     240
tttcagtttg gtgatgcaag aaaggacagt tctctccaca tcactgcagc ccagcctggt     300
gatacaggcc tctacctctg tgcaggag                                        328

<210> SEQ ID NO 80
<211> LENGTH: 358
<212> TYPE: DNA
<213> ORGANISM: Homo sapiens

<400> SEQUENCE: 80
atggccatgc tcctgggggc atcagtgctg attctgtggc ttcagccaga ctgggtaaac      60
agtcaacaga gaatgatga ccagcaagtt aagcaaaatt caccatccct gagcgtccag      120
gaaggaagaa tttctattct gaactgtgac tatactaaca gcatgtttga ttatttccta     180
tggtacaaaa ataccctgc tgaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaagcg      358

<210> SEQ ID NO 81
<211> LENGTH: 337
<212> TYPE: DNA
<213> ORGANISM: Homo sapiens

<400> SEQUENCE: 81
atggagactc tcctgaaagt gctttcaggc accttgttgt ggcagttgac ctgggtgaga      60
agccaacaac cagtgcagag tcctcaagcc gtgatcctcc gagaagggga agatgctgtc     120
atcaactgca gttcctccaa ggctttatat tctgtacact ggtacaggca gaagcatggt     180
gaagcacccg tcttcctgat gatattactg aagggtggag aacagaaggg tcatgaaaaa     240
atatctgctt catttaatga aaaaaagcag caaagctccc tgtaccttac ggcctcccag     300
ctcagttact caggaaccta cttctgcggc acagaga                              337

<210> SEQ ID NO 82
<211> LENGTH: 337
<212> TYPE: DNA
<213> ORGANISM: Homo sapiens

<400> SEQUENCE: 82
atggagactg ttctgcaagt actcctaggg atattggggt tccaagcagc ctgggtcagt      60
agccaagaac tggagcagag tcctcagtcc ttgatcgtcc agagggaaa gaatctcacc     120 ataaactgca cgtcatcaaa gacgttatat ggcttatact ggtataagca aaagtatggt     180
gaaggtctta tcttcttgat gatgctacag aaaggtgggg aagagaaaag tcatgaaaag     240
ataactgcca gttggatga aaaaagcag caaagttccc tgcatatcac agcctcccag     300
cccagccatg caggcatcta cctctgtgga gcagaca                              337

<210> SEQ ID NO 83
<211> LENGTH: 330
```

```
<212> TYPE: DNA
<213> ORGANISM: Homo sapiens

<400> SEQUENCE: 83
atgctccttg aacatttatt aataatcttg tggatgcagc tgacatgggt cagtggtcaa      60
cagctgaatc agagtcctca atctatgttt atccaggaag gagaagatgt ctccatgaac     120
tgcacttctt caagcatatt aacacctggc tatggtaca agcaggaacc tgggaaggt      180
cctgtcctct tgatagcctt ataaaggct ggtgaattga cctcaaatgg aagactgact     240
gctcagtttg gtataaccag aaaggacagc ttcctgaata tctcagcatc catacctagt    300
gatgtaggca tctacttctg tgctgggcag                                      330

<210> SEQ ID NO 84
<211> LENGTH: 340
<212> TYPE: DNA
<213> ORGANISM: Homo sapiens

<400> SEQUENCE: 84
atgatgaagt gtccacaggc tttactagct atcttttggc ttctactgag ctgggtgagc      60
agtgaagaca aggtggtaca aagccctcta tctctggttg tccacgaggg agacaccgta     120
actctcaatt gcagttatga agtgactaac tttcgaagcc tactatggta caagcaggaa    180
aagaaagctc ccacatttct atttatgcta acttcaagtg gaattgaaaa gaagtcagga    240
agactaagta gcatattaga taagaaagaa cttttccagca tcctgaacat cacagccacc   300
cagaccggag actcggccat ctacctctgt gctgtggagg                           340

<210> SEQ ID NO 85
<211> LENGTH: 350
<212> TYPE: DNA
<213> ORGANISM: Homo sapiens

<400> SEQUENCE: 85
atgacacgag ttagcttgct gtgggcagtc gtggtctcca cctgtcttga atccggcatg      60
gcccagacag tcactcagtc tcaaccagag atgtctgtgc aggaggcaga gactgtgacc    120
ctgagttgca catatgacac cagtgagaat aattattatt tgttctggta caagcagcct    180
cccagcaggc agatgattct cgttattcgc caagaagctt ataagcaaca gaatgcaacg    240
gagaatcgtt tctctgtgaa cttccagaaa gcagccaaat ccttcagtct caagatctca    300
gactcacagc tgggggacac tgcgatgtat ttctgtgctt tcatgaagca                350

<210> SEQ ID NO 86
<211> LENGTH: 349
<212> TYPE: DNA
<213> ORGANISM: Homo sapiens

<400> SEQUENCE: 86
atggcatgcc ctggcttcct gtgggcactt gtgatctcca cctgtcttga atttagcatg      60
gctcagacag tcactcagtc tcaaccagag atgtctgtgc aggaggcaga gaccgtgacc    120
ctgagctgca catatgacac cagtgagagt gattattatt tattctggta caagcagcct    180
cccagcaggc agatgattct cgttattcgc caagaagctt ataagcaaca gaatgcaaca    240
gagaatcgtt tctctgtgaa cttccagaaa gcagccaaat ccttcagtct caagatctca    300
gactcacagc tgggggatgc cgcgatgtat ttctgtgctt ataggagcg                 349

<210> SEQ ID NO 87
<211> LENGTH: 331
```

```
<212> TYPE: DNA
<213> ORGANISM: Homo sapiens

<400> SEQUENCE: 87
atgaagaagc tactagcaat gattctgtgg cttcaactag accggttaag tggagagctg      60
aaagtggaac aaaaccctct gttcctgagc atgcaggagg gaaaaaacta taccatctac     120
tgcaattatt caaccacttc agacagactg tattggtaca ggcaggatcc tgggaaaagt     180
ctggaatctc tgtttgtgtt gctatcaaat ggagcagtga agcaggaggg acgattaatg     240
gcctcacttg ataccaaagc ccgtctcagc accctccaca tcacagctgc cgtgcatgac     300
ctctctgcca cctacttctg tgccgtggac a                                    331

<210> SEQ ID NO 88
<211> LENGTH: 317
<212> TYPE: DNA
<213> ORGANISM: Homo sapiens

<400> SEQUENCE: 88
atgaactcct ctctggactt tctaattctg atcttaatgt ttggaggaac cagcagcaat      60
tcagtcaagc agacgggcca ataaccgtc tcggagggag catctgtgac tatgaactgc     120
acatacacat ccacggggta ccctacccctt ttctggtatg tggaataccc cagcaaacct    180
ctgcagcttc ttcagagaga gacaatgaaa acagcaaaa acttcggagg cggaaatatt     240
aaagacaaaa actcccccat tgtgaaatat tcagtccagg tatcagactc agccgtgtac    300
tactgtcttc tgggaga                                                   317

<210> SEQ ID NO 89
<211> LENGTH: 336
<212> TYPE: DNA
<213> ORGANISM: Homo sapiens

<400> SEQUENCE: 89
atggtgaaga tccggcaatt tttgttggct attttgtggc ttcagctaag ctgtgtaagt      60
gccgccaaaa atgaagtgga gcagagtcct cagaacctga ctgcccagga aggagaattt    120
atcacaatca actgcagtta ctcggtagga ataagtgcct acactggct gcaacagcat     180 ccaggaggag gcattgtttc cttgtttatg ctgagctcag ggaagaagaa gcatggaaga    240
ttaattgcca caataaacat acaggaaaag cacagctccc tgcacatcac agcctcccat    300
cccagagact ctgccgtcta catctgtgct gtcaga                              336

<210> SEQ ID NO 90
<211> LENGTH: 533
<212> TYPE: DNA
<213> ORGANISM: Homo sapiens

<400> SEQUENCE: 90
aggacctgaa caaggtgttc ccacccgagg tcgctgtgtt tgagccatca gaagcagaga      60
tctcccacac ccaaaaggcc acactggtgt gcctggccac aggcttcttc cccgaccacg    120
tggagctgag ctggtgggtg aatgggaagg aggtgcacag tggggtcagc acagacccgc    180
agcccctcaa ggagcagccc gccctcaatg actccagata ctgcctgagc agccgcctga    240
gggtctcggc caccttctgg cagaaccccc gcaaccactt ccgctgtcaa gtccagttct    300
acgggctctc ggagaatgac gagtggaccc aggatagggc caaacccgtc acccagatcg    360
tcagcgccga ggcctgggt agagcagact gtggctttac ctcggtgtcc taccagcaag    420
gggtcctgtc tgccaccatc ctctatgaga tcctgctagg gaaggccacc ctgtatgctg    480
```

```
tgctggtcag cgcccttgtg ttgatggcca tggtcaagag aaaggatttc tga            533
```

<210> SEQ ID NO 91
<211> LENGTH: 539
<212> TYPE: DNA
<213> ORGANISM: Homo sapiens

<400> SEQUENCE: 91

```
aggacctgaa aaacgtgttc ccacccgagg tcgctgtgtt tgagccatca gaagcagaga     60
tctcccacac ccaaaaggcc acactggtat gcctggccac aggcttctac cccgaccacg    120
tggagctgag ctggtgggtg aatgggaagg aggtgcacag tggggtcagc acagacccgc    180
agcccctcaa ggagcagccc gccctcaatg actccagata ctgcctgagc agccgcctga    240
gggtctcggc caccttctgg cagaaccccc gcaaccactt ccgctgtcaa gtccagttct    300
acgggctctc ggagaatgac gagtggacc aggatagggc caaacccgtc acccagatcg    360
tcagcgccga ggcctggggt agagcagact gtggcttcac ctccgagtct taccagcaag    420
gggtcctgtc tgccaccatc ctctatgaga tcttgctagg aaggccacc ttgtatgccg     480
tgctggtcag tgccctcgtg ctgatggcca tggtcaagag aaaggattcc agaggctag    539
```

<210> SEQ ID NO 92
<211> LENGTH: 347
<212> TYPE: DNA
<213> ORGANISM: Homo sapiens

<400> SEQUENCE: 92

```
atggatacct ggctcgtatg ctgggcaatt tttagtctct tgaaagcagg actcacagaa     60
cctgaagtca cccagactcc cagccatcag gtcacacaga tgggacagga agtgatcttg    120
cgctgtgtcc ccatctctaa tcacttatac ttctattggt acagacaaat cttggggcag    180
aaagtcgagt ttctggtttc cttttataat aatgaaatct cagagaagtc tgaaatattc    240
gatgatcaat tctcagttga aaggcctgat ggatcaaatt tcactctgaa gatccggtcc    300
acaaagctgg aggactcagc catgtacttc tgtgccagca gtgaagc                  347
```

<210> SEQ ID NO 93
<211> LENGTH: 344
<212> TYPE: DNA
<213> ORGANISM: Homo sapiens

<400> SEQUENCE: 93

```
atgggctgca ggctcctctg ctgtgtggtc ttctgcctcc tccaagcagg tcccttggac     60
acagctgttt cccagactcc aaaatacctg gtcacacaga tgggaaacga caagtccatt    120
aaatgtgaac aaaatctggg ccatgatact atgtattggt ataaacagga ctctaagaaa    180
tttctgaaga taatgtttag ctacaataat aaggagctca ttataaatga aacagttcca    240
aatcgcttct cacctaaatc tccagacaaa gctcacttaa atcttcacat caattccctg    300
gagcttggtg actctgctgt gtatttctgt gccagcagcc aaga                     344
```

<210> SEQ ID NO 94
<211> LENGTH: 344
<212> TYPE: DNA
<213> ORGANISM: Homo sapiens

<400> SEQUENCE: 94

```
atgggctgca ggctgctctg ctgtgcggtt ctctgtctcc tgggagcagt tcccatagac     60
actgaagtta cccagacacc aaaacacctg gtcatgggaa tgacaaataa gaagtctttg    120
```

```
aaatgtgaac aacatatggg gcacagggct atgtattggt acaagcagaa agctaagaag      180
ccaccggagc tcatgtttgt ctacagctat gagaaactct ctataaatga aagtgtgcca      240
agtcgcttct cacctgaatg ccccaacagc tctctcttaa accttcacct acacgccctg      300
cagccagaag actcagccct gtatctctgc gccagcagcc aaga                      344

<210> SEQ ID NO 95
<211> LENGTH: 344
<212> TYPE: DNA
<213> ORGANISM: Homo sapiens

<400> SEQUENCE: 95
atgggctgca ggctgctctg ctgtgcggtt ctctgtctcc tgggagcggt ccccatggaa      60
acgggagtta cgcagacacc aagacacctg gtcatgggaa tgacaaataa gaagtctttg     120
aaatgtgaac aacatctggg gcataacgct atgtattggt acaagcaaag tgctaagaag     180
ccactggagc tcatgtttgt ctacaacttt aaagaacaga ctgaaaacaa cagtgtgcca     240
agtcgcttct cacctgaatg ccccaacagc tctcacttat ccttcacct acacaccctg      300 cagccagaag actcggccct gtatctctgt gccagcagcc aaga                      344

<210> SEQ ID NO 96
<211> LENGTH: 344
<212> TYPE: DNA
<213> ORGANISM: Homo sapiens

<400> SEQUENCE: 96
atgggctgca ggctgctctg ctgtgcggtt ctctgtctcc tgggagcggt ccccatggaa      60
acgggagtta cgcagacacc aagacacctg gtcatgggaa tgacaaataa gaagtctttg     120
aaatgtgaac aacatctggg tcataacgct atgtattggt acaagcaaag tgctaagaag     180
ccactggagc tcatgtttgt ctacagtctt gaagaacggg ttgaaaacaa cagtgtgcca     240
agtcgcttct cacctgaatg ccccaacagc tctcacttat ccttcacct acacaccctg      300 cagccagaag actcggccct gtatctctgc gccagcagcc aaga                      344

<210> SEQ ID NO 97
<211> LENGTH: 343
<212> TYPE: DNA
<213> ORGANISM: Homo sapiens

<400> SEQUENCE: 97
atgggctcca ggctgctctg ttgggtgctg ctttgtctcc tgggagcagg cccagtaaag      60
gctggagtca ctcaaactcc aagatatctg atcaaaacga gaggacagca agtgacactg     120
agctgctccc ctatctctgg gcataggagt gtatcctggt accaacagac cccaggacag     180
ggccttcagt tcctctttga atacttcagt gagacacaga gaaacaaagg aaacttccct     240
ggtcgattct caggcgcca gttctctaac tctcgctctg atgaatgt gagcaccttg        300 gagctggggg actcggccct ttatctttgc gccagcagct tgg                       343

<210> SEQ ID NO 98
<211> LENGTH: 341
<212> TYPE: DNA
<213> ORGANISM: Homo sapiens

<400> SEQUENCE: 98
atgggccccg gctcctctg ctgggaactg ctttatctcc tgggagcagg cccagtggag       60
gctggagtca cccaaagtcc cacacacctg atcaaaacga gaggacagca agtgactctg     120
```

-continued

| agatgctctc ctatctctgg gcacagcagt gtgtcctggt accaacaggc cccgggtcag | 180 |
| gggccccagt ttatctttga atatgctaat gagttaagga gatcagaagg aaacttccct | 240 |
| aatcgattct cagggcgcca gttccatgac tgttgctctg agatgaatgt gagtgccttg | 300 |
| gagctggggg actcggccct gtatctctgt gccagaagct t | 341 |

<210> SEQ ID NO 99
<211> LENGTH: 343
<212> TYPE: DNA
<213> ORGANISM: Homo sapiens

<400> SEQUENCE: 99

| atgggccctg ggctcctctg ctgggtgctg ctttgtctcc tgggagcagg ctcagtggag | 60 |
| actggagtca cccaaagtcc cacacacctg atcaaaacga gaggacagca agtgactctg | 120 |
| agatgctctt ctcagtctgg gcacaacact gtgtcctggt accaacaggc cctgggtcag | 180 |
| gggccccagt ttatctttca gtattatagg gaggaagaga atggcagagg aaacttccct | 240 |
| cctagattct caggtctcca gttccctaat tatagctctg agctgaatgt gaacgccttg | 300 |
| gagctggacg actcggccct gtatctctgt gccagcagct tgg | 343 |

<210> SEQ ID NO 100
<211> LENGTH: 343
<212> TYPE: DNA
<213> ORGANISM: Homo sapiens

<400> SEQUENCE: 100

| atgggccctg ggctcctctg ctgggtgctg ctttgtctcc tgggagcagg cccagtggac | 60 |
| gctggagtca cccaaagtcc cacacacctg atcaaaacga gaggacagca agtgactctg | 120 |
| agatgctctc ctatctctgg gcacaagagt gtgtcctggt accaacaggt cctgggtcag | 180 |
| gggccccagt ttatctttca gtattatgag aaagaagaga gaggaagagg aaacttccct | 240 |
| gatcgattct cagctcgcca gttccctaac tatagctctg agctgaatgt gaacgccttg | 300 |
| ttgctggggg actcggccct gtatctctgt gccagcagct tgg | 343 |

<210> SEQ ID NO 101
<211> LENGTH: 343
<212> TYPE: DNA
<213> ORGANISM: Homo sapiens

<400> SEQUENCE: 101

| atgggccccg ggctcctctg ctgggcactg ctttgtctcc tgggagcagg cttagtggac | 60 |
| gctggagtca cccaaagtcc cacacacctg atcaaaacga gaggacagca agtgactctg | 120 |
| agatgctctc ctaagtctgg gcatgacact gtgtcctggt accaacaggc cctgggtcag | 180 |
| gggccccagt ttatctttca gtattatgag gaggaagaga gacagagagg caacttccct | 240 |
| gatcgattct caggtcacca gttccctaac tatagctctg agctgaatgt gaacgccttg | 300 |
| ttgctggggg actcggccct ctatctctgt gccagcagct tgg | 343 |

<210> SEQ ID NO 102
<211> LENGTH: 343
<212> TYPE: DNA
<213> ORGANISM: Homo sapiens

<400> SEQUENCE: 102

| atgggccccg ggctcctctg ctgggtgctg ctttgtcccc taggagaagg cccagtggac | 60 |
| gctggagtca cccaaagtcc cacacacctg atcaaaacga gaggacagca cgtgactctg | 120 |

```
agatgctctc ctatctctgg gcacaccagt gtgtcctcgt accaacaggc cctgggtcag      180 gggcccagt ttatctttca gtattatgag aaagaagaga gaggaagagg aaacttccct      240
gatcaattct caggtcacca gttccctaac tatagctctg agctgaatgt gaacgccttg      300
ttgctagggg actcggccct ctatctctgt gccagcagct tgg                        343

<210> SEQ ID NO 103
<211> LENGTH: 343
<212> TYPE: DNA
<213> ORGANISM: Homo sapiens

<400> SEQUENCE: 103
atgggaccca ggctcctctt ctgggcactg ctttgtctcc tcggaacagg cccagtggag      60
gctggagtca cacaaagtcc cacacacctg atcaaaacga gaggacagca agcgactctg     120
agatgctctc ctatctctgg gcacaccagt gtgtactggt accaacaggc cctgggtctg     180
ggcctccagt tcctcctttg gtatgacgag ggtgaagaga gaaacagagg aaacttccct    240
cctagatttt caggtcgcca gttccctaat tatagctctg agctgaatgt gaacgccttg     300
gagctggagg actcggccct gtatctctgt gccagcagct tgg                        343

<210> SEQ ID NO 104
<211> LENGTH: 344
<212> TYPE: DNA
<213> ORGANISM: Homo sapiens

<400> SEQUENCE: 104
atgagcatcg ggctcctgtg ctgtgtggcc ttttctctcc tgtgggcaag tccagtgaat      60
gctggtgtca ctcagacccc aaaattccag gtcctgaaga caggacagag catgacactg    120
cagtgtgccc aggatatgaa ccataactcc atgtactggt atcgacaaga cccaggcatg    180
ggactgaggc tgatttatta ctcagcttct gagggtacca ctgacaaagg agaagtcccc    240
aatggctaca atgtctccag attaaacaaa cgggagttct cgctcaggct ggagtcggct    300
gctccctccc agacatctgt gtacttctgt gccagcagtg aagc                      344

<210> SEQ ID NO 105
<211> LENGTH: 344
<212> TYPE: DNA
<213> ORGANISM: Homo sapiens

<400> SEQUENCE: 105
atgagcctcg ggctcctgtg ctgtgggggcc ttttctctcc tgtgggcagg tccagtgaat     60
gctggtgtca ctcagacccc aaaattccgg gtcctgaaga caggacagag catgacactg    120
ctgtgtgccc aggatatgaa ccatgaatac atgtactggt atcgacaaga cccaggcatg    180
gggctgaggc tgattcatta ctcagttggt gagggtacaa ctgccaaagg agaggtccct    240
gatggctaca atgtctccag attaaaaaaa cagaatttcc tgctgggggtt ggagtcggct    300 gctccctccc aaacatctgt gtacttctgt gccagcagtt actc                      344

<210> SEQ ID NO 106
<211> LENGTH: 344
<212> TYPE: DNA
<213> ORGANISM: Homo sapiens

<400> SEQUENCE: 106
atgagcctcg ggctcctgtg ctgtgggggtc ttttctctcc tgtgggcagg tccagtgaat     60
gctggtgtca ctcagacccc aaaattccgg gtcctgaaga caggacagag catgacactg    120
```

```
ctgtgtgccc aggatatgaa ccatgaatac atgtactggt atcgacaaga cccaggcatg      180
gggctgaggc tgattcatta ctcagttggt gagggtacaa ctgccaaagg agaggtccct      240
gatggctaca atgtctccag attaaaaaaa cagaatttcc tgctggggtt ggagtcggct      300
gctccctccc aaacatctgt gtacttctgt gccagcagtt actc                      344

<210> SEQ ID NO 107
<211> LENGTH: 344
<212> TYPE: DNA
<213> ORGANISM: Homo sapiens

<400> SEQUENCE: 107
atgagaatca ggctcctgtg ctgtgtggcc ttttctctcc tgtgggcagg tccagtgatt      60
gctgggatca cccaggcacc aacatctcag atcctggcag caggacggcg catgacactg      120
agatgtaccc aggatatgag acataatgcc atgtactggt atagacaaga tctaggactg      180
gggctaaggc tcatccatta ttcaaatact gcaggtacca ctggcaaagg agaagtccct      240
gatggttata gtgtctccag agcaaacaca gatgatttcc ccctcacgtt ggcgtctgct      300
gtaccctctc agacatctgt gtacttctgt gccagcagtg actc                      344

<210> SEQ ID NO 108
<211> LENGTH: 344
<212> TYPE: DNA
<213> ORGANISM: Homo sapiens

<400> SEQUENCE: 108
atgagcatcg gcctcctgtg ctgtgcagcc ttgtctctcc tgtgggcagg tccagtgaat      60
gctggtgtca ctcagacccc aaaattccag gtcctgaaga caggacagag catgacactg      120
cagtgtgccc aggatatgaa ccatgaatac atgtcctggt atcgacaaga cccaggcatg      180
gggctgaggc tgattcatta ctcagttggt gctggtatca ctgaccaagg agaagtcccc      240
aatggctaca atgtctccag atcaaccaca gaggatttcc cgctcaggct gctgtcggct      300
gctccctccc agacatctgt gtacttctgt gccagcagtt actc                      344

<210> SEQ ID NO 109
<211> LENGTH: 344
<212> TYPE: DNA
<213> ORGANISM: Homo sapiens

<400> SEQUENCE: 109
atgagcatca gcctcctgtg ctgtgcagcc tttcctctcc tgtgggcagg tccagtgaat      60
gctggtgtca ctcagacccc aaaattccgc atcctgaaga taggacagag catgacactg      120
cagtgtaccc aggatatgaa ccataactac atgtactggt atcgacaaga cccaggcatg      180
gggctgaagc tgatttatta ttcagttggt gctggtatca ctgataaagg agaagtcccg      240
aatggctaca acgtctccag atcaaccaca gaggatttcc cgctcaggct ggagttggct      300
gctccctccc agacatctgt gtacttctgt gccagcagtt actc                      344

<210> SEQ ID NO 110
<211> LENGTH: 344
<212> TYPE: DNA
<213> ORGANISM: Homo sapiens

<400> SEQUENCE: 110
atgagcctcg ggctcctgtg ctgtgtggcc ttttctctcc tgtgggcagg tccaatgaat      60
gctggtgtca ctcagacccc aaaattccac gtcctgaaga caggacagag catgactctg      120
```

```
ctgtgtgccc aggatatgaa ccatgaatac atgtatcggt atcgacaaga cccaggcaag    180
gggctgaggc tgatttacta ctcagttgct gctgctctca ctgacaaagg agaagttccc    240
aatggctaca atgtctccag atcaaacaca gaggatttcc ccctcaagct ggagtcagct    300
gctccctctc agacttctgt ttacttctgt gccagcagtt actc                    344
```

<210> SEQ ID NO 111
<211> LENGTH: 341
<212> TYPE: DNA
<213> ORGANISM: Homo sapiens

<400> SEQUENCE: 111

```
atgagcctcg ggctcctgtg ctgtgcggcc ttttctctcc tgtgggcagg tcccgtgaat    60
gctggtgtca ctcagacccc aaaattccac atcctgaaga caggacagag catgacactg    120
cagtgtgccc aggatatgaa ccatggatac atgtcctggt atcgacaaga cccaggcatg    180
gggctgagac tgatttacta ctcagctgct gctggtacta ctgacaaaga agtccccaat    240
ggctacaatg tctctagatt aaacacagag gatttcccac tcaggctggt gtcggctgct    300
ccctcccaga catctgtgta cttgtgtgcc agcagttact c                        341
```

<210> SEQ ID NO 112
<211> LENGTH: 344
<212> TYPE: DNA
<213> ORGANISM: Homo sapiens

<400> SEQUENCE: 112

```
atgagcatcg ggctcctgtg ctgtgtggcc ttttctctcc tgtgggcagg tccagtgaat    60
gctggtgtca ctcagacccc aaaattccac atcctgaaga caggacagag catgacactg    120
cagtgtgccc aggatatgaa ccatggatac ttgtcctggt atcgacaaga cccaggcatg    180
gggctgaggc gcattcatta ctcagttgct gctggtatca ctgacaaagg agaagtcccc    240
gatggctaca atgtatccag atcaaacaca gaggatttcc cgctcaggct ggagtcagct    300
gctccctccc agacatctgt atacttctgt gccagcagtt attc                     344
```

<210> SEQ ID NO 113
<211> LENGTH: 347
<212> TYPE: DNA
<213> ORGANISM: Homo sapiens

<400> SEQUENCE: 113

```
atgggcacaa ggctcctctg ctgggcagcc atatgtctcc tgggggcaga tcacacaggt    60
gctggagtct cccagtccct gagacacaag gtagcaaaga agggaaagga tgtagctctc    120
agatatgatc caatttcagg tcataatgcc ctttattggt accgacagag cctggggcag    180
ggcctggagt ttccaattta cttccaaggc aaggatgcag cagacaaatc ggggcttccc    240
cgtgatcggt tctctgcaca gaggtctgag ggatccatct ccactctgaa gttccagcgc    300
acacagcagg gggacttggc tgtgtatctc tgtgccagca gctcagc                  347
```

<210> SEQ ID NO 114
<211> LENGTH: 347
<212> TYPE: DNA
<213> ORGANISM: Homo sapiens

<400> SEQUENCE: 114

```
atgggcacca ggctcctctt ctgggtggcc ttctgtctcc tgggggcaga tcacacagga    60
gctggagtct cccagtcccc cagtaacaag gtcacagaga agggaaagga tgtagagctc    120
```

```
aggtgtgatc caatttcagg tcatactgcc ctttactggt accgacagag cctggggcag    180
ggcctggagt ttttaattta cttccaaggc aacagtgcac cagacaaatc agggctgccc    240
agtgatcgct tctctgcaga gaggactggg ggatccgtct ccactctgac gatccagcgc    300
acacagcagg aggactcggc cgtgtatctc tgtgccagca gcttagc                  347
```

<210> SEQ ID NO 115
<211> LENGTH: 347
<212> TYPE: DNA
<213> ORGANISM: Homo sapiens

<400> SEQUENCE: 115

```
atgggcacca ggctcctctg ctgggcagcc ctgtgcctcc tggggcagat cacacaggt     60 gctggagtct cccagacccc cagtaacaag gtcacagaga agggaaaata tgtagagctc    120
aggtgtgatc caatttcagg tcatactgcc ctttactggt accgacaaag cctggggcag    180
ggcccagagt ttctaattta cttccaaggc acgggtgcgg cagatgactc agggctgccc    240
aacgatcggt tctttgcagt caggcctgag ggatccgtct ctactctgaa gatccagcgc    300
acagagcggg gggactcagc cgtgtatctc tgtgccagca gcttaac                  347
```

<210> SEQ ID NO 116
<211> LENGTH: 347
<212> TYPE: DNA
<213> ORGANISM: Homo sapiens

<400> SEQUENCE: 116

```
atgggcacca ggctcctctg ctgggtggtc ctgggtttcc tagggacaga tcacacaggt    60
gctggagtct cccagtcccc aaggtacaaa gtcgcaaaga ggggacggga tgtagctctc    120
aggtgtgatt caatttcggg tcatgtaacc ctttattggt accgacagac cctggggcag    180
ggctcagagg ttctgactta ctcccagagt gatgctcaac gagacaaatc agggcggccc    240
agtggtcggt tctctgcaga gaggcctgag agatccgtct ccactctgaa gatccagcgc    300
acagagcagg gggactcagc tgtgtatctc tgtgccagca gcttagc                  347
```

<210> SEQ ID NO 117
<211> LENGTH: 347
<212> TYPE: DNA
<213> ORGANISM: Homo sapiens

<400> SEQUENCE: 117

```
atgggcacca gtctcctatg ctgggtggtc ctgggtttcc tagggacaga tcacacaggt    60
gctggagtct cccagtctcc caggtacaaa gtcacaaaga ggggacagga tgtagctctc    120
aggtgtgatc caatttcggg tcatgtatcc ctttattggt accgacaggc cctggggcag    180
ggcccagagt ttctgactta cttcaattat gaagcccaac aagacaaatc agggctgccc    240
aatgatcggt tctctgcaga gaggcctgag ggatccatct ccactctgac gatccagcgc    300
acagagcagc gggactcggc catgtatcgc tgtgccagca gcttagc                  347
```

<210> SEQ ID NO 118
<211> LENGTH: 347
<212> TYPE: DNA
<213> ORGANISM: Homo sapiens

<400> SEQUENCE: 118

```
atgggtacca gtctcctatg ctgggtggtc ctgggtttcc tagggacaga tcacacaggt    60
gctggagtct cccagtctcc caggtacaaa gtcacaaaga ggggacagga tgtaactctc    120
```

```
aggtgtgatc caatttcgag tcatgcaacc ctttattggt atcaacaggc cctggggcag      180
ggcccagagt ttctgactta cttcaattat gaagctcaac cagacaaatc agggctgccc      240
agtgatcggt tctctgcaga gaggcctgag ggatccatct ccactctgac gattcagcgc      300
acagagcagc gggactcagc catgtatcgc tgtgccagca gcttagc                    347
```

<210> SEQ ID NO 119
<211> LENGTH: 347
<212> TYPE: DNA
<213> ORGANISM: Homo sapiens

<400> SEQUENCE: 119

```
atgggcacca ggctcctctg ctgggtggtc ctgggtttcc tagggacaga tcacacaggt      60
gctggagtct cccagtcccc taggtacaaa gtcgcaaaga aggacagga tgtagctctc       120 aggtgtgatc caatttcggg tcatgtatcc cttttttggt accaacaggc cctggggcag      180
gggccagagt ttctgactta tttcagaat gaagctcaac tagacaaatc ggggctgccc       240
agtgatcgct tctttgcaga aaggcctgag ggatccgtct ccactctgaa gatccagcgc      300
acacagcagg aggactccgc cgtgtatctc tgtgccagca gcttagc                    347
```

<210> SEQ ID NO 120
<211> LENGTH: 347
<212> TYPE: DNA
<213> ORGANISM: Homo sapiens

<400> SEQUENCE: 120

```
atgggcacca gcctcctctg ctggatggcc ctgtgtctcc tgggggcaga tcacgcagat      60
actggagtct cccagaaccc cagacacaag atcacaaaga ggggacagaa tgtaactttc      120
aggtgtgatc caatttctga acacaaccgc ctttattggt accgacagac cctggggcag      180
ggcccagagt ttctgactta cttcagaat gaagctcaac tagaaaaatc aaggctgctc       240
agtgatcggt tctctgcaga gaggcctaag ggatctttct ccaccttgga gatccagcgc      300
acagagcagg gggactcggc catgtatctc tgtgccagca gcttagc                    347
```

<210> SEQ ID NO 121
<211> LENGTH: 343
<212> TYPE: DNA
<213> ORGANISM: Homo sapiens

<400> SEQUENCE: 121

```
atgggcttca ggctcctctg ctgtgtggcc ttttgtctcc tgggagcagg cccagtggat      60
tctggagtca cacaaacccc aaagcacctg atcacagcaa ctggacagcg agtgacgctg      120
agatgctccc ctaggtctgg agacctctct gtgtactggt accaacagag cctggaccag      180
ggcctccagt tcctcattca gtattataat ggagaagaga gagcaaaagg aaacattctt      240
gaacgattct ccgcacaaca gttccctgac ttgcactctg aactaaacct gagctctctg      300
gagctggggg actcagcttt gtatttctgt gccagcagcg tag                        343
```

<210> SEQ ID NO 122
<211> LENGTH: 344
<212> TYPE: DNA
<213> ORGANISM: Homo sapiens

<400> SEQUENCE: 122

```
atgggcacga ggctcttctt ctatgtggcc ctttgtctgc tgtgggcagg acacagggat      60
gctgaaatca cccagagccc aagacacaag atcacagaga caggaaggca ggtgaccttg      120
```

```
gcgtgtcacc agacttggaa ccacaacaat atgttctggt atcgacaaga cctgggacat      180
gggctgaggc tgatccatta ctcatatggt gttcaagaca ctaacaaagg agaagtctca      240
gatggctaca gtgtctctag atcaaacaca gaggacctcc ccctcactct ggagtctgct      300
gcctcctccc agacatctgt atatttctgc gccagcagtg agtc                      344

<210> SEQ ID NO 123
<211> LENGTH: 344
<212> TYPE: DNA
<213> ORGANISM: Homo sapiens

<400> SEQUENCE: 123
atgggcacca ggctcttctt ctatgtggcc ctttgtctgc tgtgggcagg acacagggat       60
gctggaatca cccagagccc aagatacaag atcacagaga caggaaggca ggtgaccttg      120
atgtgtcacc agacttggag ccacagctat atgttctggt atcgacaaga cctgggacat      180
gggctgaggc tgatctatta ctcagcagct gctgatatta cagataaagg agaagtcccc      240
gatggctatg ttgtctccag atccaagaca gagaatttcc ccctcactct ggagtcagct      300
acccgctccc agacatctgt gtatttctgc gccagcagtg agtc                      344

<210> SEQ ID NO 124
<211> LENGTH: 344
<212> TYPE: DNA
<213> ORGANISM: Homo sapiens

<400> SEQUENCE: 124
atgggcacaa ggttgttctt ctatgtggcc ctttgtctcc tgtggacagg acacatggat       60
gctggaatca cccagagccc aagacacaag gtcacagaga caggaacacc agtgactctg      120
agatgtcacc agactgagaa ccaccgctat atgtactggt atcgacaaga cccggggcat      180
gggctgaggc tgatccatta ctcatatggt gttaaagata ctgacaaagg agaagtctca      240
gatggctata gtgtctctag atcaaagaca gaggatttcc tcctcactct ggagtccgct      300
accagctccc agacatctgt gtacttctgt gccatcagtg agtc                      344

<210> SEQ ID NO 125
<211> LENGTH: 347
<212> TYPE: DNA
<213> ORGANISM: Homo sapiens

<400> SEQUENCE: 125
atgagcacca ggcttctctg ctggatggcc ctctgtctcc tggggcaga actctcagaa        60 gctgaagttg cccagtcccc cagatataag attacagaga aaagccaggc tgtggctttt      120
tggtgtgatc ctatttctgg ccatgctacc ctttactggt accggcagat cctgggacag      180
ggcccggagc ttctggttca atttcaggat gagagtgtag tagatgattc acagttgcct      240
aaggatcgat tttctgcaga gaggctcaaa ggagtagact ccactctcaa gatccagcct      300
gcagagcttg gggactcggc catgtatctc tgtgccagca gcttagc                   347

<210> SEQ ID NO 126
<211> LENGTH: 347
<212> TYPE: DNA
<213> ORGANISM: Homo sapiens

<400> SEQUENCE: 126
atgggcacca ggctcctctg ctgggcggcc ctctgtctcc tgggagcaga actcacagaa        60
gctggagttg cccagtctcc cagatataag attatagaga aaaggcagag tgtggctttt      120
```

```
tggtgcaatc ctatatctgg ccatgctacc ctttactggt accagcagat cctgggacag      180
ggcccaaagc ttctgattca gtttcagaat aacggtgtag tggatgattc acagttgcct      240
aaggatcgat tttctgcaga gaggctcaaa ggagtagact ccactctcaa gatccagcct      300
gcaaagcttg aggactcggc cgtgtatctc tgtgccagca gcttaga                   347

<210> SEQ ID NO 127
<211> LENGTH: 347
<212> TYPE: DNA
<213> ORGANISM: Homo sapiens

<400> SEQUENCE: 127
atgggtacca ggctcctctg ctgggtggcc ttctgtctcc tggtggaaga actcatagaa       60
gctggagtgg ttcagtctcc cagatataag attatagaga aaaaacagcc tgtggctttt      120
tggtgcaatc ctatttctgg ccacaatacc ctttactggt acctgcagaa cttgggacag      180
ggcccggagc ttctgattcg atatgagaat gaggaagcag tagacgattc acagttgcct      240
aaggatcgat tttctgcaga gaggctcaaa ggagtagact ccactctcaa gatccagcct      300
gcagagcttg gggactcggc cgtgtatctc tgtgccagca gcttaga                   347

<210> SEQ ID NO 128
<211> LENGTH: 347
<212> TYPE: DNA
<213> ORGANISM: Homo sapiens

<400> SEQUENCE: 128
atggactcct ggaccttctg ctgtgtgtcc cttttgcatcc tggtagcgaa gcatacagat       60
gctggagtta tccagtcacc ccgccatgag gtgacagaga tgggacaaga agtgactctg      120
agatgtaaac caatttcagg ccacaactcc cttttctggt acagacagac catgatgcgg      180
ggactggagt tgctcattta ctttaacaac aacgttccga tagatgattc agggatgccc      240
gaggatcgat tctcagctaa gatgcctaat gcatcattct ccactctgaa gatccagccc      300
tcagaaccca gggactcagc tgtgtacttc tgtgccagca gtttagc                   347

<210> SEQ ID NO 129
<211> LENGTH: 347
<212> TYPE: DNA
<213> ORGANISM: Homo sapiens

<400> SEQUENCE: 129
atggactcct ggaccctctg ctgtgtgtcc cttttgcatcc tggtagcaaa gcacacagat       60
gctggagtta tccagtcacc ccggcacgag gtgacagaga tgggacaaga agtgactctg      120
agatgtaaac caatttcagg acacgactac cttttctggt acagacagac catgatgcgg      180
ggactggagt tgctcattta ctttaacaac aacgttccga tagatgattc agggatgccc      240
gaggatcgat tctcagctaa gatgcctaat gcatcattct ccactctgaa gatccagccc      300
tcagaaccca gggactcagc tgtgtacttc tgtgccagca gtttagc                   347

<210> SEQ ID NO 130
<211> LENGTH: 347
<212> TYPE: DNA
<213> ORGANISM: Homo sapiens

<400> SEQUENCE: 130
atggccacca ggctcctctg ctgtgtggtt ctttgtctcc tgggagaaga gcttatagat       60
gctagagtca cccagacacc aaggcacaag gtgacagaga tgggacaaga agtaacaatg      120
```

```
agatgtcagc caattttagg ccacaatact gttttctggt acagacagac catgatgcaa    180
ggactggagt tgctggctta cttccgcaac cgggctcctc tagatgattc ggggatgccg    240
aaggatcgat tctcagcaga gatgcctgat gcaactttag ccactctgaa gatccagccc    300
tcagaaccca gggactcagc tgtgtatttt tgtgctagtg gtttggt                  347
```

```
<210> SEQ ID NO 131
<211> LENGTH: 374
<212> TYPE: DNA
<213> ORGANISM: Homo sapiens

<400> SEQUENCE: 131
atgcttagtc ctgacctgcc tgactctgcc tggaacacca ggctcctctg ccatgtcatg     60
ctttgtctcc tgggagcagt ttcagtggct gctggagtca tccagtcccc aagacatctg    120
atcaaagaaa agagggaaac agccactctg aaatgctatc ctatccctag acacgacact    180
gtctactggt accagcaggg tccaggtcag gaccccccagt tcctcatttc gttttatgaa    240
aagatgcaga gcgataaagg aagcatccct gatcgattct cagctcaaca gttcagtgac    300
tatcattctg aactgaacat gagctccttg gagctggggg actcagccct gtacttctgt    360
gccagcagct tagg                                                      374
```

```
<210> SEQ ID NO 132
<211> LENGTH: 347
<212> TYPE: DNA
<213> ORGANISM: Homo sapiens

<400> SEQUENCE: 132 atggttttcca ggcttctcag tttagtgtcc ctttgtctcc tgggagcaaa gcacatagaa    60
gctggagtta ctcagttccc cagccacagc gtaatagaga agggccagac tgtgactctg    120
agatgtgacc caattctgg acatgataat ctttattggt atcgacgtgt tatgggaaaa    180
gaaataaaat ttctgttaca ttttgtgaaa gagtctaaac aggatgagtc cggtatgccc    240
aacaatcgat tcttagctga aaggactgga gggacgtatt ctactctgaa ggtgcagcct    300
gcagaactgg aggattctgg agtttatttc tgtgccagca gccaaga                  347
```

```
<210> SEQ ID NO 133
<211> LENGTH: 344
<212> TYPE: DNA
<213> ORGANISM: Homo sapiens

<400> SEQUENCE: 133
atgggtcctg gcttctcca ctggatggcc ctttgtctcc ttggaacagg tcatggggat     60
gccatggtca tccagaaccc aagataccag gttacccagt ttggaaagcc agtgaccctg    120
agttgttctc agactttgaa ccataacgtc atgtactggt accagcagaa gtcaagtcag    180
gccccaaagc tgctgttcca ctactatgac aaagatttta acaatgaagc agacacccct    240
gataacttcc aatccaggag gccgaacact tctttctgct tcttgacat ccgctcacca    300 ggcctggggg acacagccat gtacctgtgt gccaccagca gaga                     344
```

```
<210> SEQ ID NO 134
<211> LENGTH: 347
<212> TYPE: DNA
<213> ORGANISM: Homo sapiens

<400> SEQUENCE: 134
atgagcccaa tattcacctg catcacaatc ctttgtctgc tggctgcagg ttctcctggt     60
```

```
gaagaagtcg cccagactcc aaaacatctt gtcagagggg aaggacagaa agcaaaatta        120
tattgtgccc caataaaagg acacagttag gttttttggt accaacaggt cctgaaaaac        180
gagttcaagt tcttgatttc cttccagaat gaaaatgtct ttgatgaaac aggtatgccc        240
aaggaaagat tttcagctaa gtgcctccca aattcaccct gtagccttga gatccaggct        300
acgaagcttg aggattcagc agtgtatttt tgtgccagca gccaatc                      347

<210> SEQ ID NO 135
<211> LENGTH: 344
<212> TYPE: DNA
<213> ORGANISM: Homo sapiens

<400> SEQUENCE: 135
atggatatct ggctcctctg ctgggtgacc ctgtgtctct tggcggcagg acactcggag         60
cctggagtca gccagacccc cagacacaag gtcaccaaca tgggacagga ggtgattctg        120
aggtgcgatc catcttctgg tcacatgttt gttcactggt accgcagaa tctgaggcaa         180 gaaatgaagt tgctgatttc cttccagtac caaaacattg cagttgattc agggatgccc        240
aaggaacgat tcacagctga aagacctaac ggaacgtctt ccacgctgaa gatccatccc        300
gcagagccga gggactcagc cgtgtatctc tacagtagcg gtgg                          344

<210> SEQ ID NO 136
<211> LENGTH: 347
<212> TYPE: DNA
<213> ORGANISM: Homo sapiens

<400> SEQUENCE: 136
atggacacca gagtactctg ctgtgcggtc atctgtcttc tgggggcagg tctctcaaat         60
gccggcgtca tgcagaaccc aagacacctg gtcaggagga ggggacagga ggcaagactg        120
agatgcagcc caatgaaagg acacagtcat gtttactggt atcggcagct cccagaggaa        180
ggtctgaaat tcatggttta tctccagaaa gaaaatatca tagatgagtc aggaatgcca        240
aaggaacgat tttctgctga atttcccaaa gagggcccca gcatcctgag gatccagcag        300
gtagtgcgag gagattcggc agcttatttc tgtgccagct caccacc                      347

<210> SEQ ID NO 137
<211> LENGTH: 344
<212> TYPE: DNA
<213> ORGANISM: Homo sapiens

<400> SEQUENCE: 137
atgagcaacc aggtgctctg ctgtgtggtc ctttgtttcc tgggagcaaa caccgtggat         60
ggtggaatca ctcagtcccc aaagtacctg ttcagaaagg aaggacagaa tgtgaccctg        120
agttgtgaac agaatttgaa ccacgatgcc atgtactggt accgacagga cccagggcaa        180
gggctgagat tgatctacta ctcacagata gtaaatgact ttcagaaagg agatatagct        240
gaagggtaca gcgtctctcg ggagaagaag gaatcctttc ctctcactgt gacatcggcc        300
caaaagaacc cgacagcttt ctatctctgt gccagtagta taga                          344

<210> SEQ ID NO 138
<211> LENGTH: 335
<212> TYPE: DNA
<213> ORGANISM: Homo sapiens

<400> SEQUENCE: 138
atgctgctgc ttctgctgct tctggggcca ggctccgggc ttggtgctgt cgtctctcaa         60
```

```
catccgagct gggttatctg taagagtgga acctctgtga agatcgagtg ccgttccctg    120
gactttcagg ccacaactat gttttggtat cgtcagttcc cgaaacagag tctcatgctg    180
atggcaactt ccaatgaggg ctccaaggcc acatacgagc aaggcgtcga aaggacaag     240 tttctcatca accatgcaag cctgaccttg tccactctga cagtgaccag tgcccatcct    300
gaagacagca gcttctacat ctgcagtgct agaga                               335
```

<210> SEQ ID NO 139
<211> LENGTH: 347
<212> TYPE: DNA
<213> ORGANISM: Homo sapiens

<400> SEQUENCE: 139

```
atgggcacca ggctcctcgg ctgtgcagcc ctgtgtctcc tggcagcaga ctctttcat     60 gccaaagtca cacagactcc aggacatttg gtcaaaggaa aggacagaa aacaaagatg    120 gattgtaccc ccgaaaaagg acatactttt gtttattggt atcaacagaa tcagaataaa   180
gagtttatgc ttttgatttc ctttcagaat gaacaagttc ttcaagaaac ggagatgcac   240
aagaagcgat tctcatctca atgccccaag aacgcaccct gcagcctggc aatcctgtcc    300
tcagaaccgg gagacacggc actgtatctc tgcgccagca gtcaatc                  347
```

<210> SEQ ID NO 140
<211> LENGTH: 345
<212> TYPE: DNA
<213> ORGANISM: Homo sapiens

<400> SEQUENCE: 140

```
atggcctccc tgctcttctt ctgtgggggcc ttttatctcc tgggaacagg gtccatggat   60
gctgatgtta cccagacccc aaggaatagg atcacaaaga caggaaagag gattatgctg    120
gaatgttctc agactaaggg tcatgataga atgtactggt atcgacaaga cccaggactg   180
ggcctacggt tgatctatta ctcctttgat gtcaaagata taaacaaagg agagatctct   240
gatggataca gtgtctctcg acaggcacag gctaaattct ccctgtccct agagtctgcc   300
atccccaacc agacagctct ttacttctgt gccaccagtg atttg                   345
```

<210> SEQ ID NO 141
<211> LENGTH: 344
<212> TYPE: DNA
<213> ORGANISM: Homo sapiens

<400> SEQUENCE: 141

```
atgactatca ggctcctctg ctacatgggc ttttattttc tggggggcagg cctcatggaa    60 gctgacatct accagacccc aagataccct gttataggga caggaaagaa gatcactctg    120
gaatgttctc aaaccatggg ccatgacaaa atgtactggt atcaacaaga tccaggaatg    180
gaactacacc tcatccacta ttcctatgga gttaattcca cagagaaggg agatcttttcc   240 tctgagtcaa cagtctccag aataaggacg agcattttc ccctgacct ggagtctgcc     300 aggccctcac atacctctca gtacctctgt gccagcagtg aata                     344
```

<210> SEQ ID NO 142
<211> LENGTH: 344
<212> TYPE: DNA
<213> ORGANISM: Homo sapiens

<400> SEQUENCE: 142

```
atgggccccc agctccttgg ctatgtggtc ctttgccttc taggagcagg ccccctggaa    60
```

-continued

```
gcccaagtga cccagaaccc aagatacctc atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca aagtctctcg aaaagagaag aggaatttcc ccctgatcct ggagtcgccc    300
agccccaacc agacctctct gtacttctgt gccagcagtt tatc                    344
```

<210> SEQ ID NO 143
<211> LENGTH: 344
<212> TYPE: DNA
<213> ORGANISM: Homo sapiens

<400> SEQUENCE: 143

```
atgggaatca ggctcctctg tcgtgtggcc ttttgtttcc tggctgtagg cctcgtagat     60
gtgaaagtaa cccagagctc gagatatcta gtcaaaagga cgggagagaa agttttttctg   120 gaatgtgtcc aggatatgga ccatgaaaat atgttctggt atcgacaaga cccaggtctg    180
gggctacggc tgatctattt ctcatatgat gttaaaatga agaaaaagg agatattcct     240 gagggggtaca gtgtctctag agagaagaag gagcgcttct ccctgattct ggagtccgcc   300
agcaccaacc agacatctat gtacctctgt gccagcagtt tatg                    344
```

<210> SEQ ID NO 144
<211> LENGTH: 335
<212> TYPE: DNA
<213> ORGANISM: Homo sapiens

<400> SEQUENCE: 144

```
atgctgagtc ttctgctcct tctcctggga ctaggctctg tgttcagtgc tgtcatctct     60
caaaagccaa gcagggatat ctgtcaacgt ggaacctccc tgacgatcca gtgtcaagtc    120
gatagccaag tcaccatgat gttctggtac cgtcagcaac ctggacagag cctgacactg    180
atcgcaactg caaatcaggg ctctgaggcc acatatgaga gtggatttgt cattgacaag    240
tttcccatca gccgcccaaa cctaacattc tcaactctga ctgtgagcaa catgagccct    300
gaagacagca gcatatatct ctgcagcgtt gaaga                              335
```

<210> SEQ ID NO 145
<211> LENGTH: 335
<212> TYPE: DNA
<213> ORGANISM: Homo sapiens

<400> SEQUENCE: 145

```
atgctctgct ctctccttgc ccttctcctg ggcactttct ttggggtcag atctcagact     60
attcatcaat ggccagcgac cctggtgcag cctgtgggca gcccgctctc tctggagtgc    120
actgtggagg gaacatcaaa ccccaaccta tactggtacc gacaggctgc aggcaggggc    180
ctccagctgc tcttctactc cgttggtatt ggccagatca gctctgaggt gccccagaat    240
ctctcagcct ccagacccca ggaccggcag ttcatcctga gttctaagaa gctccttctc    300
agtgactctg gcttctatct ctgtgcctgg agtgt                              335
```

<210> SEQ ID NO 146
<211> LENGTH: 624
<212> TYPE: DNA
<213> ORGANISM: Artificial Sequence
<220> FEATURE:
<223> OTHER INFORMATION: DNA encoding soluble AH1.23 TCR alpha chain
      with introduced disulfide interchain bond -continued

<400> SEQUENCE: 146

```
atgaaggagg tggagcagaa ttctggaccc ctcagtgttc cagagggagc cattgcctct      60
ctcaactgca cttacagtga ccgaggttcc cagtccttct tctggtacag acaatattct     120
gggaaaagcc ctgagttgat aatgttcata tactccaatg gtgacaaaga agatggaagg     180
tttacagcac agctcaataa agccagccag tatgtttctc tgctcatcag agactcccag     240
cccagtgatt cagccaccta cctctgtgcc gtgaaggggg ggtctggggg ttaccagaaa     300
gttacctttg aactggaac aaagctccaa gtcatcccaa atatccagaa cccggatcct      360
gccgtgtacc agctgagaga ctctaaatcc agtgacaagt ctgtctgcct attcaccgat     420
tttgattctc aaacaaatgt gtcacaaagt aaggattctg atgtgtatat cacagacaaa     480
tgtgtgctag acatgaggtc tatggacttc aagagcaaca gtgctgtggc ctggagcaac     540
aaatctgact ttgcatgtgc aaacgccttc aacaacagca ttattccaga agacaccttc     600
ttccccagcc agaaagttc ctaa                                              624
```

<210> SEQ ID NO 147
<211> LENGTH: 735
<212> TYPE: DNA
<213> ORGANISM: Artificial Sequence
<220> FEATURE:
<223> OTHER INFORMATION: DNA encoding soluble AH1.23 TCR beta chain with introduced disulfide interchain bond

<400> SEQUENCE: 147

```
atgggcgtca tgcagaaccc aagacacctg gtcaggagga ggggacagga ggcaagactg      60
agatgcagcc aatgaaagg acacagtcat gtttactggt atcggcagct cccagaggaa      120
ggtctgaaat tcatggttta ctccagaaa gaaaatatca tagatgagtc aggaatgcca      180
aaggaacgat tttctgctga atttcccaaa gagggcccca gcatcctgag gatccagcag     240
gtagtgcgag gagattcggc agcttatttc tgtgccagct caccacagac aggggggcaca     300 gatacgcagt attttggccc aggcacccgg ctgacagtgc tcgaggacct gaaaaacgtg     360
ttcccacccg aggtcgctgt gtttgagcca tcagaagcag agatctccca cacccaaaag     420
gccacactgg tgtgcctggc cacaggcttc taccccgacc acgtggagct gagctggtgg     480
gtgaatggga aggaggtgca cagtggggtc tgcacagacc cgcagcccct caaggagcag     540
cccgccctca tgactccag atacgctctg agcagccgcc tgagggtctc ggccaccttc     600
tggcaggacc cccgcaacca cttccgctgt caagtccagt ctacgggct ctcggagaat     660 gacgagtgga cccaggatag ggccaaaccc gtcacccaga tcgtcagcgc cgaggcctgg     720
ggtagagcag actaa                                                       735
```

<210> SEQ ID NO 148
<211> LENGTH: 207
<212> TYPE: PRT
<213> ORGANISM: Artificial Sequence
<220> FEATURE:
<223> OTHER INFORMATION: Soluble AH1.23 TCR alpha chain with introduced disulfide interchain bond

<400> SEQUENCE: 148

```
Met Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45
```

```
Phe Ile Tyr Ser Asn Gly Asp Lys Glu Asp Gly Arg Phe Thr Ala Gln
         50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val Lys Gly Gly Ser Gly
                 85                  90                  95

Gly Tyr Gln Lys Val Thr Phe Gly Thr Gly Thr Lys Leu Gln Val Ile
                100                 105                 110

Pro Asn Ile Gln Asn Pro Asp Pro Ala Val Tyr Gln Leu Arg Asp Ser
                115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
                180                 185                 190

Ser Ile Ile Pro Glu Asp Thr Phe Phe Pro Ser Pro Glu Ser Ser
                195                 200                 205

<210> SEQ ID NO 149
<211> LENGTH: 244
<212> TYPE: PRT
<213> ORGANISM: Artificial Sequence
<220> FEATURE:
<223> OTHER INFORMATION: Soluble AH1.23 TCR beta chain with introduced
      disulfide interchain bond

<400> SEQUENCE: 149

Met Gly Val Met Gln Asn Pro Arg His Leu Val Arg Arg Arg Gly Gln
  1               5                  10                  15

Glu Ala Arg Leu Arg Cys Ser Pro Met Lys Gly His Ser His Val Tyr
                 20                  25                  30

Trp Tyr Arg Gln Leu Pro Glu Glu Gly Leu Lys Phe Met Val Tyr Leu
             35                  40                  45

Gln Lys Glu Asn Ile Ile Asp Glu Ser Gly Met Pro Lys Glu Arg Phe
 50                  55                  60

Ser Ala Glu Phe Pro Lys Glu Gly Pro Ser Ile Leu Arg Ile Gln Gln
 65                  70                  75                  80

Val Val Arg Gly Asp Ser Ala Ala Tyr Phe Cys Ala Ser Ser Pro Gln
                 85                  90                  95

Thr Gly Gly Thr Asp Thr Gln Tyr Phe Gly Pro Gly Thr Arg Leu Thr
                100                 105                 110

Val Leu Glu Asp Leu Lys Asn Val Phe Pro Pro Glu Val Ala Val Phe
                115                 120                 125

Glu Pro Ser Glu Ala Glu Ile Ser His Thr Gln Lys Ala Thr Leu Val
130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
                180                 185                 190

Arg Leu Arg Val Ser Ala Thr Phe Trp Gln Asp Pro Arg Asn His Phe
                195                 200                 205
```

```
Arg Cys Gln Val Gln Phe Tyr Gly Leu Ser Glu Asn Asp Glu Trp Thr
    210                 215                 220
Gln Asp Arg Ala Lys Pro Val Thr Gln Ile Val Ser Ala Glu Ala Trp
225                 230                 235                 240
Gly Arg Ala Asp
```

CELLS EXPRESSING A MODIFIED T CELL RECEPTOR

This application is a National Stage application of co-pending PCT application PCT/GB2005/002570 filed Jan. 5 2005, which was published in English under PCT Article 21(2) on Jun. 29, 2005, and which claims the benefit of Great Britain patent applications Serial No. GB 0414499.4 filed Jun. 29, 2004; Serial No. 0421831.9 filed Oct. 1, 2004; and Serial No. 0511123.2 filed Jun. 1, 2005. These applications are incorporated herein by reference in their entireties.

This application incorporates by reference the contents of a 80.6 KB text file created on Oct. 22, 2009 and named "Ser. No. 11/597,252_sequencelisting.txt," which is the sequence listing for this application.

The present invention relates to cells, particularly T cells, expressing modified T cell receptors (TCRs), their preparation, and their use in therapy.

BACKGROUND TO THE INVENTION

Native TCRs

As is described in, for example, WO 99/60120 TCRs mediate the recognition of specific Major Histocompatibility Complex (MHC)-peptide complexes by T cells and, as such, are essential to the functioning of the cellular arm of the immune system.

Antibodies and TCRs are the only two types of molecules which recognise antigens in a specific manner, and thus the TCR is the only receptor for particular peptide antigens presented in MHC, the alien peptide often being the only sign of an abnormality within a cell. T cell recognition occurs when a T-cell and an antigen presenting cell (APC) are in direct physical contact, and is initiated by ligation of antigen-specific TCRs with pMHC complexes.

The native TCR is a heterodimeric cell surface protein of the immunoglobulin superfamily which is associated with invariant proteins of the CD3 complex involved in mediating signal transduction. TCRs exist in $\alpha\beta$ and $\gamma\delta$ forms, which are structurally similar but have quite distinct anatomical locations and probably functions. The MHC class I and class II ligands are also immunoglobulin superfamily proteins but are specialised for antigen presentation, with a highly polymorphic peptide binding site which enables them to present a diverse array of short peptide fragments at the APC cell surface.

Two further classes of proteins are known to be capable of functioning as TCR ligands. (1) CD1 antigens are MHC class I-related molecules whose genes are located on a different chromosome from the classical MHC class I and class II antigens. CD1 molecules are capable of presenting peptide and non-peptide (eg lipid, glycolipid) moieties to T cells in a manner analogous to conventional class I and class II-MHC-pep complexes. See, for example (Barclay et al, (1997) The Leucocyte Antigen Factsbook $2^{nd}$ Edition, Academic Press) and (Bauer (1997) Eur J Immunol 27 (6) 1366-1373)) (2) Bacterial superantigens are soluble toxins which are capable of binding both class II MHC molecules and a subset of TCRs. (Fraser (1989) Nature 339 221-223) Many superantigens exhibit specificity for one or two Vbeta segments, whereas others exhibit more promiscuous binding. In any event, superantigens are capable of eliciting an enhanced immune response by virtue of their ability to stimulate subsets of T cells in a polyclonal fashion.

The extracellular portion of native heterodimeric $\alpha\beta$ and $\gamma\delta$ TCRs consist of two polypeptides each of which has a membrane-proximal extracellular constant domain, and a membrane-distal variable region. Each of the extracellular constant domain and variable region includes an intra-chain disulfide bond. The variable regions contain the highly polymorphic loops analogous to the complementarity determining regions (CDRs) of antibodies. CDR3 of $\alpha\beta$ TCRs interact with the peptide presented by MHC, and CDRs 1 and 2 of $\alpha\beta$ TCRs interact with the peptide and the MHC. The diversity of TCR sequences is generated via somatic rearrangement of linked variable (V), diversity (D), joining (J), and constant genes, the genes products thereof making up the variable region.

Functional $\alpha$ and $\gamma$ chain polypeptides are formed by rearranged V-J-C domains, whereas $\beta$ and $\delta$ chains consist of V-D-J-C domains. (See FIG. 1) Each functional TCR possessing one of the possible variants of each domain. (See FIGS. 7 and 8 for the DNA sequences of all known TCR C and V domains from TCR $\alpha$ and $\beta$ chains respectively, also see (LeFranc et al, (2001) The T cell receptor Factsbook, Academic Press) for a complete listing of the DNA and amino acid sequences of all known TCR domains) A further level of diversity is introduced to $\alpha\beta$ TCRs by the in-vivo recombination of shortened TCR domains. The extracellular constant domain has a membrane proximal motif and an immunoglobulin motif. There are single $\alpha$ and $\beta$ chain constant domains, known as TRAC and TRDC respectively. The $\beta$ chain constant domain is composed of one of two different $\beta$ constant domains, known as TRBC1 and TRBC2 (IMGT nomenclature). There are four amino acid changes between these $\beta$ constant domains, three of which are in exon 1 of TRBC1 and TRBC2: $N_4K_5$->$K_4N_5$ and $F_{37}$->$Y$, the final amino acid change between the two TCR $\beta$ chain constant regions being in exon 3 of TRBC1 and TRBC2: $V_1$->$E$. (IMGT numbering, differences TRBC1->TRBC2) The constant $\gamma$ domain is composed of one of either TRGC1, TRGC2 (2×) or TRGC2 (3×). The two TRGC2 constant domains differ only in the number of copies of the amino acids encoded by exon 2 of this gene that are present. TCR constant domains include a transmembrane sequence, the amino acids of which anchor the TCR chains into the cell surface membrane. There are 46 different TRAV domains and 56 TRBV domains. 52 different functional genes encode the TRAJ domains, whereas 12-13 functional genes encode the TRBJ domains. 2 different functional genes encode the TRBD domains.

The extent of each of the TCR extracellular constant domains, bounded by the transmembrane sequences, is somewhat variable. However, a person skilled in the art can readily determine the position of the domain boundaries using a reference such as The T Cell Receptor Facts Book, Lefranc & Lefranc, Publ. Academic Press 2001.

Immunotherapy

Immunotherapy involves enhancing the immune response of a patient to cancerous or infected cells. Active immunotherapy is carried out by stimulation of the endogenous immune system of tumour bearing patients. Passive, or adoptive, immunotherapy involves the transfer of immune competent cells into the patient. (Paul (2002) Curr Gene Therapy 2 91-100) There are three broad approaches to adoptive immunotherapy which have been applied in the clinic for the treatment of metastatic diseases; lymphokine-activated killer (LAK) cells, auto-lymphocyto therapy (ALT) and tumour-infiltrating lymphocutes (TIL). (Paul (2002) *Curr Gene Therapy* 2 91-100).

A recent proposed variation of T cell adoptive therapy is the use of gene therapy techniques to introduce TCRs specific for known cancer-specific MHC-peptide complexes into the T cells of cancer patients. For example, (WO 01/55366) discloses retrovirus-based methods for transfecting, preferably, T cells with heterologous TCRs. This document states that these transfected cells could be used for either the cell surface display of TCR variants as a means of identifying high affinity TCRs or for immunotherapy. Methods for the molecular cloning of cDNA of a human p53-specific, HLA restricted murine TCR and the transfer of this cDNA to human T cells are described in published US patent application no. 20020064521. This document states that the expression of this murine TCR results in the recognition of endogenously processed human p53 expressed in tumour cells pulsed with the p53-derived peptide 149-157 presented by HLA A*0201 and claims the use of the murine TCR in anti-cancer adoptive immunotherapy. However, the concentration of peptide pulsing required achieving half maximal T cell stimulation of the transfected T cells was approximately 250 times that required by T cells expressing solely the murine TCR. As the authors noted "The difference in level of peptide sensitivity is what might be expected of a transfectant line that contained multiple different TCR heterodimers as a result of independent association of all four expressed hu and mu TCR chains."

There are also a number of recent papers relating to T cell adoptive therapy. In one study (Rosenberg (1988) *N Engl J Med* 319 (25) 1676-80) lymphocytes from melanomas were expanded in vitro and these tumor-infiltrating lymphocytes, in combination with IL-2 were used to treat 20 patients with metastatic melanoma by means of adoptive transfer. The authors note that objective regression of the cancer was observed in 9 of 15 patients (60 percent) who had not previously been treated with interleukin-2 and in 2 of 5 patients (40 percent) in whom previous therapy with interleukin-2 had failed. Regression of cancer occurred in the lungs, liver, bone, skin, and subcutaneous sites and lasted from 2 to more than 13 months. A farther study describes the administration of an expanded population of Melan-A specific cytotoxic T cells to eight patients with refractory malignant melanoma. These T cells were administered by i.v. infusion at fortnightly intervals, accompanied by s.c. administration of IL-2. The T cell infusions were well tolerated with clinical responses noted as one partial, one mixed with shrinkage of one metastatic deposit and one no change (12 months) among the eight patients. (Meidenbauer (2003) *J Immunol* 170 2161-2169) As noted in this study, recent advances regarding the in vitro stimulation T cells for the generation of cell populations suitable for T cell adoptive therapy have made this approach more practical. See, for example (Oelke (2000) *Clin Cancer Res* 6 1997-2005) and (Szmania (2001) *Blood* 98 505-12).

BRIEF DESCRIPTION OF THE INVENTION

The present invention relates to cells presenting at least one T cell receptor (TCR) anchored to the membrane by a transmembrane sequence, said TCR comprising an interchain disulfide bond between extracellular constant domain residues which is not present in native TCRs. Such T cells are expected to be particularly suited for use in T cell adoptive immunotherapy.

DETAILED DESCRIPTION OF THE INVENTION

This invention provides a cell presenting at least one T cell receptor (TCR) anchored to the membrane by a transmembrane sequence, said TCR comprising an interchain disulfide bond between extracellular constant domain residues which is not present in native TCRs.

As noted above native TCRs exist in $\alpha\beta$ and $\gamma\delta$ forms, the present invention encompasses cells presenting either of these TCR forms, wherein said TCR comprises an interchain disulfide bond between extracellular constant domain residues which is not present in native TCRs.

Another embodiment provides a cell presenting at least one $\alpha\beta$ T cell receptor (TCR) anchored to the membrane by a transmembrane sequence, said TCR comprising a disulfide bond between $\alpha$ and $\beta$ extracellular constant domain residues which is not present in native TCRs.

The presence of the novel cysteine residues (creating the novel disulfide bond) in the transfected heterodimeric TCR (dTCR) chains favour the production of the desired transfected TCRs over TCRs comprising a native TCR chain associated with a transfected TCR chain. Without wishing to be bound by theory, this result is interpreted as being due to the two transfected TCR chains preferentially self-associating due to the formation of the novel inter-chain disulfide bond between the introduced cysteine residues. The formation of any TCR comprising a mismatched pair of TCR chains (one native and one from the transfected TCR) may be further inhibited by ensuring the transfected chains lack the cysteine residue involved in the formation of the native inter-chain disulfide bond. Cells expressed such transfected TCR chains therefore provide a preferred embodiment of the invention.

Use of a single chain TCR (scTCR) in accordance with the invention also avoids formation of mismatched pairs.

The $\alpha\beta$ TCRs which comprise a disulfide bond between $\alpha$ and $\beta$ extracellular constant domain residues which is not present in native TCRs presented by the cells of the invention are targeting moieties. The TCRs of the invention target TCR ligands such as peptide-MHC or CD1-antigen complexes. As such, it would be desirable if the affinity of these TCR could be altered. For example it may be desirable if these TCR had a higher affinity and/or a slower off-rate for the TCR ligands than native TCRs specific for that ligand. The inventors co-pending application WO 2004/044004 details methods of producing and testing TCRs having a higher affinity and/or a slower off-rate for the TCR ligand than native TCRs specific for that ligand.

The TCR functionality of cells transfected to express and present the membrane anchored scTCRs and dTCRs may be tested by confirming that transfected cells bind to the relevant TCR ligand (PMHC complex, CD1-antigen complex, superantigen or superantigen/pMHC complex)—if it binds, then the requirement is met. The binding of the transfected cells to a TCR ligand can be detected by a number of methods. These include attaching a detectable label to the TCR ligand. For example, where the method uses pMHC tetramers, the pMHC may include a fluorescent label. Protocol 6 herein provides a detailed description of the methods required to analyse the binding of cells transfected to express disulfide-linked TCRs to MHC-peptide complexes. This method is equally applicable to the study of TCR/CD1 interactions. In order to apply this method to the study of TCR/CD1 interactions soluble forms of CD1 are required, the production of which are described in (Bauer (1997) *Eur J Immunol* 27 (6) 1366-1373).

The Cell Membrane Anchored dTCR

In the case of a dTCR, the TCR $\alpha$ and $\beta$ chains may each comprise a transmembrane sequence, fused at its N terminus to an extracellular constant domain sequence, in turn fused at its N terminus to a variable region sequence. Furthermore, at least the said sequences of the TCR $\alpha$ and $\beta$ chains other than the complementarity determining regions of the variable region, may correspond to human TCR $\alpha$ and $\beta$ sequences.

The Cell Membrane Anchored scTCR

In the case of an scTCR, the scTCR comprises (i) a first segment constituted by an $\alpha$ chain variable region sequence fused to the N terminus of an $\alpha$ chain extracellular constant domain sequence, and a second segment constituted by a β chain variable region sequence fused to the N terminus of a sequence β chain extracellular constant and transmembrane sequence, and a linker sequence linking the C terminus of the first segment to the N terminus of the second segment, or (ii) a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and a linker sequence linking the C terminus of the first segment to the N terminus of the second segment.

Again, in the scTCR embodiment, the said sequences of the TCR α and β chains other than the complementarity determining regions of the variable region, correspond to human TCR α and β sequences.

Linker in the Membrane Anchored scTCR Polypeptide

For the cell presented scTCRs of the present invention, a linker sequence links the first and second TCR segments, to form a single polypeptide strand. The linker sequence may, for example, have the formula -P-AA-P- wherein P is proline and AA represents an amino acid sequence wherein the amino acids are glycine and serine.

For the cell presented scTCRs of the present invention to bind to a TCR ligand, such as MHC-peptide or CD1-antigen complexes, the first and second segments must be paired so that the variable region sequences thereof are orientated for such binding. Hence the linker should have sufficient length to span the distance between the C terminus of the first segment and the N terminus of the second segment, or vice versa. On the other hand excessive linker length should preferably be avoided, in case the end of the linker at the N-terminal variable region sequence blocks or reduces bonding of the scTCR to the target ligand.

For example, in the case where the constant region extracellular sequences present in the first segment correspond to the constant regions of the α and β chains of a native TCR truncated at their C termini such that the cysteine residue that forms the native interchain disulfide bond of the TCR is excluded, and the linker sequence links the C terminus of the first segment to the N terminus of the second segment, the linker may consist of from 26 to 41, for example 29, 30, 31 or 32 amino acids, and a particular linker has the formula -PGGG-(SGGGG)$_5$-P- Wherein P is proline, G is glycine and S is serine (SEQ ID NO:1).

The Cell Membrane Anchored scTCR and dTCR

As mentioned above, preferred embodiments the dTCR or scTCR α and β chain sequences correspond to human TCR α and β sequences, with the exception of the complementarity determining regions (CDRs) of the variable regions which may or may not correspond to human CDR sequences. However, correspondence between such sequences need not be 1:1 on an amino acid level. N- or C-truncation, and/or amino acid deletion and/or substitution relative to corresponding human TCR sequences is acceptable, provided the overall result is a cell membrane anchored TCR comprising mutual orientation of the α and β variable region sequences is as in native αβ T cell receptors respectively. In particular, because the constant domain extracellular sequences are not directly involved in contacts with the ligand to which the cell membrane anchored scTCR or dTCR binds, they may be shorter than, or may contain substitutions or deletions relative to, extracellular constant domain sequences of native TCRs.

Included in the scope of this invention are cells presenting membrane anchored TCRs comprising amino acids encoded by any appropriate combination of the nucleic acid sequences corresponding to those disclosed in FIGS. 7 and 8. As is known to those skilled in the art, TCRs can also be produced by combination of amino acid sequences encoded by truncated variants of the sequences disclosed in FIGS. 7 & 8. Such TCRs form an additional embodiment of the present invention. Also included within the scope of this invention are membrane anchored TCRs encoded by any variants of these nucleic acid molecules.

Usually, cells according to the invention will present a plurality of the said scTCR or dTCR (the exogenous TCRs). Each of the plurality of the said scTCRs or dTCRs is preferably identical, but if the cell is a T-cell, it may also present some native (endogenous) TCRs, residually encoded by the T cell chromosomes.

Another preferred embodiment provides T cells having the said membrane anchored scTCR or dTCR, or a plurality thereof. In a further preferred embodiment these T cells are cytotoxic T cells.

Another preferred embodiment provides cells that reduces the cellular or pro-inflammatory arms of an auto-immune response having the said membrane anchored scTCR or dTCR, or a plurality thereof. Examples of such cells, include, but are not limited to macrophages, γδ T cells, Th3 T cells, Tr1 T cells, NK T cells, macrophages and regulatory T cells. In a further preferred embodiment these cells are regulatory T cells.

Regulatory T cells are characterised by the cell-surface expression of CD4 and CD25. (Bluestone and Tang *Proc Natl Acad Sci USA*. 2004 101 Suppl 2: 14622-6.) provides a review of regulatory T cells.

In a further embodiment of the invention the cells present scTCR or dTCR which contains a covalent disulfide bond linking a residue of the immunoglobulin region of the constant domain of the α chain to a residue of the immunoglobulin region of the constant domain of the β chain.

A further embodiment of the invention provides a cell presenting scTCR or dTCR wherein in the said TCR an inter-chain disulfide bond in native TCR is not present.

A further embodiment of the invention provides a cell presenting scTCR or dTCR wherein in the said TCR cysteine residues which form the native interchain disulfide bond are substituted to another residue.

A further embodiment of the invention provides a cell presenting scTCR or dTCR wherein in the said TCR cysteine residues which form the native interchain disulfide bond are substituted to serine or alanine.

A further embodiment of the invention provides a cell presenting scTCR or dTCR wherein in the said TCR an unpaired cysteine residue present in native TCR β chain is not present.

Inter-Chain Disulfide Bond

A principal characterising feature of the cell membrane anchored scTCRs and dTCRs of the present invention, is a disulfide bond between the constant region extracellular sequences of the dTCR polypeptide pair or first and second segments of the scTCR polypeptide. That bond may correspond to the native inter-chain disulfide bond present in native dimeric αβ TCRs, or may have no counterpart in native TCRs, being between cysteines specifically incorporated into the constant region extracellular sequences of dTCR polypeptide pair or first and second segments of the scTCR polypeptide. In some cases, both a native and a non-native disulfide bond may be desirable.

The position of the disulfide bond is subject to the requirement that the variable region sequences of dTCR polypeptide pair or first and second segments of the scTCR polypeptide are mutually orientated substantially as in native αβ T cell receptors.

The disulfide bond may be formed by mutating non-cysteine residues on the first and second segments to cysteine, and causing the bond to be formed between the mutated residues. Residues whose respective β carbons are approximately 6 Å (0.6 nm) or less, and preferably in the range 3.5 Å (0.35 nm) to 5.9 Å (0.59 nm) apart in the native TCR are preferred, such that a disulfide bond can be formed between cysteine residues introduced in place of the native residues. It is preferred if the disulfide bond is between residues in the constant immunoglobulin region, although it could be between residues of the membrane proximal region. Preferred sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
| --- | --- | --- |
| Thr 48 | Ser 57 | 0.473 |
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

Now that the residues in human TCRs which can be mutated into cysteine residues to form a new interchain disulfide bond in cell membrane bound dTCRs or scTCRs according to the invention have been identified, those of skill in the art will be able to mutate TCRs of other species in the same way to produce a dTCR or scTCR of that species for cell membrane bound expression. In humans, the skilled person merely needs to look for the following motifs in the respective TCR chains to identify the residue to be mutated (the shaded residue is the residue for mutation to a cysteine).

α Chain Thr 48: DSDVYITDKTVLDMRSMDFK (amino acids 39-58 of exon 1 of the TRAC*01 gene)(SEQ ID NO:2)

α Chain Thr 45: QSKDSDVYITDKTVLDMRSM (amino acids 36-55 of exon 1 of the TRAC*01 gene)(SEQ ID NO:3)

α Chain Tyr 10: DIQNPDPAVYQLRDSKSSDK (amino acids 1-20 of exon 1 of the TRAC*01 gene)(SEQ ID NO:4)

α Chain Ser 15: DPAVYQLRDSKSSDKSVCLF (amino acids 6-25 of exon 1 of the TRAC*01 gene)(SEQ ID NO:5)

β Chain Ser 57: NGKEVHSGVSTDPQPLKEQP (amino acids 48-67 of exon 1 of the TRBC1*01 & TRBC2*01 genes)(SEQ ID NO:6)

β Chain Ser 77: ALNDSRYALSSRLRVSATFW (amino acids 68-87 of exon 1 of the TRBC1*01 & TRBC2*01 genes)(SEQ ID NO:7)

β Chain Ser 17: PPEVAVFEPSEAEISHTQKA (amino acids 8-27 of exon 1 of the TRBC1*01 & TRBC2*01 genes)(SEQ ID NO:8)

β Chain Asp 59: KEVHSGVSTDPQPLKEQPAL (amino acids 50-69 of exon 1 of the TRBC1*01 & TRBC2*01 genes gene)(SEQ ID NO:9)

β Chain Glu 15: VFPPEVAVFEPSEAEISHTQ (amino acids 6-25 of exon 1 of the TRBC1*01 & TRBC2*01 genes)(SEQ ID NO:10)

In other species, the TCR chains may not have a region which has 100% identity to the above motifs. However, those of skill in the art will be able to use the above motifs to identify the equivalent part of the TCR α or β chain and hence the residue to be mutated to cysteine. Alignment techniques may be used in this respect. For example, ClustalW, available on the European Bioinformatics Institute website (http://www.ebi.ac.uk/index.html) can be used to compare the motifs above to a particular TCR chain sequence in order to locate the relevant part of the TCR sequence for mutation.

The present invention includes within its scope cell membrane bound αβ scTCRs and dTCRs, as well as those of other mammals, including, but not limited to, mouse, rat, pig, goat and sheep. As mentioned above, those of skill in the art will be able to determine sites equivalent to the above-described human sites at which cysteine residues can be introduced to form an inter-chain disulfide bond. For example, the following shows the amino acid sequences of the mouse Cα and Cβ soluble domains, together with motifs showing the murine residues equivalent to the human residues mentioned above that can be mutated to cysteines to form a TCR interchain disulfide bond (where the relevant residues are shaded):

(SEQ ID NO:11)
Mouse Cα soluble domain:
PYIQNPEPAVYQLKDPRSQDSTLCLFTDFDSQINVPKTMESGTFITDKTV

LDMKAMDSKSNGAIAWSNQTSFTCQDIFKETNATYPSSDVP (SEQ ID NO:12)
Mouse Cβ soluble domain:
EDLRNVTPPKVSLFEPSKAEIANKQKATLVCLARGFFPDHVELSWWVNGR

EVHSGVSTDPQAYKESNYSYCLSSRLRVSATFWHNPRNHFRCQVQFHGLS

EEDKWPEGSPKPVTQNISAEAWGRAD

Murine equivalent of human α Chain Thr 48: ESGTFITDKTVLDMKAMDSK (SEQ ID NO:13)
Murine equivalent of human α Chain Thr 45: KTMESGTFITDKTVLDMKAM (SEQ ID NO:14)
Murine equivalent of human α Chain Tyr 10: YIQNPEPAVYQLKDPRSQDS (SEQ ID NO:15)
Murine equivalent of human α Chain Ser 15: AVYQLKDPRSQDSTLCLFTD (SEQ ID NO:16)
Murine equivalent of human β Chain Ser 57: NGREVHSGVSTDPQAYKESN (SEQ ID NO:17)
Murine equivalent of human β Chain Ser 77: KESNYSYCLSSRLRVSATFW (SEQ ID NO:18)
Murine equivalent of human β Chain Ser 17: PPKVSLFEPSKAEIANKQKA (SEQ ID NO:19)
Murine equivalent of human β Chain Asp 59: REVHSGVSTDPQAYKESNYS (SEQ ID NO:20)
Murine equivalent of human β Chain Glu 15: VTPPKVSLFEPSKAEIANKQ (SEQ ID NO:21)

A nucleic acid molecule or molecules comprising a sequence or sequences encoding a membrane anchored scTCR or dTCR are also provided, as are vectors comprising said nucleic acid molecules. Included in the scope of this invention are nucleic acid sequences encoding membrane anchored TCR comprising any appropriate combination of nucleic acid sequence corresponding to those disclosed in FIGS. 7 and 8. As is known to those skilled in the art, TCRs can also be produced that comprise combinations of amino acids encoded by truncated variants of the nucleic sequences disclosed in FIGS. 7 and 8, such nucleic acid sequences form an additional embodiment of the present invention. Also included within the scope of this invention are variants of these nucleic acid molecules that encode membrane anchored TCRs.

The nucleic acid or nucleic acids encoding TCRs of the invention may be provided in a form which has been adapted for expression in a prokaryote or eukaryote host cell. Suitable host cells include, but are not limited to, bacterial, yeast, mammalian or insect cells. For example, the host cell may be a human T cell or a human haematopoietic stem cell.

Such adapted nucleic acid or nucleic acids is/are mutated to reflect the codon preference of the host cell in to which it is introduced. The mutations introduced are silent mutations which do not affect the amino acid sequence of the polypeptide or polypeptides thereby encoded. GeneArt (Regensburg, Germany) offer a suitable nucleic acid optimisation service (GeneOptimizer™). WO 2004/059556, owned by GeneArt, provides further details of the optimisation process. Nucleic acid complementary to any such adapted nucleic acid sequence or a RNA sequence corresponding thereto also forms part of this invention. Furthermore, as will be obvious to those skilled in the art such nucleic acid or nucleic acids encoding TCRs of the invention may also comprise non-coding (intron) sequences.

As will be obvious to those skilled in the art such full-length TCR chain DNA sequences encode for the following sequences:
  A leader sequence and the extracellular, transmembrane, and cytoplasmic TCR sequences.

A method for obtaining a cell expressing a membrane anchored scTCR or dTCR is also provided, said method comprises incubating a host cell harbouring a vector encoding the membrane anchored scTCR or dTCR under conditions causing expression of the scTCR or dTCR.

Preparation of Cells Expressing TCRs Comprising a Non-Native Disulfide Interchain Bond Another embodiment provides a method for the preparation of cells of the invention said method comprising:
  (a) isolation of a population of cells, preferably a population of T cells
  (b) in vitro transfection of said population of cells with an expression vector encoding a TCR of the invention specific for a target cell,
  (c) optional in vitro growth of the transfected cells.

In a preferred embodiment the population of cells is isolated from a patient to be treated by a method of directing said cells to a population of target cells.

The following provides details of the isolation, transformation and optional in-vitro growth of T cells.

Isolation of T Cells

T cells are found in both the bloodstream and lymphatic system. Generally, in order to obtain a suitable sample of T cells a venous blood sample is first obtained. In a preferred embodiment of the invention this blood sample is obtained from the patient requiring treatment.

The skilled person will be able to prepare a suitable sample of T cells for use in the present invention. For example, the sample may be whole blood, or a sample prepared from blood including, but not limited to, peripheral blood leucocytes (PBLs) or peripheral blood mononuclear cells (PBMC).

The T cells in the blood sample obtained are then be isolated by fluorescent activated cell sorting (FACS). Briefly, this involves the addition of florescent labels which specifically bind to T cell-specific 'marker' proteins and sorting the cells into populations based on the presence or absence of these labels. These fluorescent labels typically comprise an antibody, or fragment thereof, to which is attached a fluorescent moiety such as phycoerythicin (PE). The choice of label, or labels, used will determine the cell types present in the sorted populations:

| Label Used | Cell Population isolated |
| --- | --- |
| Anti CD3 fluorescent label | All (cytotoxic and helper) T cells |
| Anti CD8 fluorescent label | $CD8^+$ (cyto-toxic) T cells |
| Anti CD4 fluorescent label | $CD4^+$ (helper) T cells |
| Anti CD4 and anti CD25 fluorescent label | Regulatory T cells | in vitro transfection T cells with a vector encoding a TCR specific for the target cell There are many techniques suitable for the transfection of mammalian cells, such as human T cells, that are known to those skilled in the art. Textbooks including the following provide experimental protocols that describe the methods involved: Sambrook et al. *Molecular Cloning: A Laboratory Manual,* 2nd Ed., Cold Spring Harbor Laboratory, Cold Spring Harbor, N.Y., 1989; Ausubel et al. *Current Protocols in Molecular Biology*, John Wiley & Sons, New York, 1992; Glover *DNA Cloning, I and II*, Oxford Press, Oxford, 1985; B. D. Hames & S. J. Higgins *Nucleic Acid Hybridization* 1984; J. H. Miller and M. P. Calos, *Gene Transfer Vectors For Mammalian Cells*, Cold Spring Harbor Laboratory, Cold Spring Harbor, N.Y., 1987).

As stated above two recent patent applications are directed to the transfection of T cells with TCRs. (WO 01/55366 and US 20020064521) The methods disclosed in these applications are also applicable to the transfection of T cells with the TCRs of this invention that comprise a disulfide bond between residues not present in native TCRs. Briefly, WO 01/55366 discloses a retro-viral method for the introduction of TCRs with defined specificity into T cells. The application describes methods for the production of a retro-viral vector containing the α and β chains of a high affinity murine TCR specific for a nucleoprotein peptide (ASNENMDAM) (SEQ ID NO:22) presented by the murine class I MHC $H-2D^b$. This vector was then replicated in a human embryonic kidney cell line and the retroviral supernatant was collected to provide the material required for T cell transfection. US 20020064521 describes methods for the molecular cloning of cDNA of a human p53-specific, HLA restricted murine TCR and the transfer of this cDNA to human T cells. α and β chain TCR cDNAs were subcloned separately into a mammalian expression vector. This vector was then transferred into Jurkat cells using standard liposome transfection procedures. Surface expression Of the transfected TCR was then confirmed by flow cytometry.

In vitro Growth of the Transfected T Cells

Once the T cells required for adoptive therapy have been transfected with the required TCR they can optionally be cultured in vitro to provide an expanded population of T cells using standard techniques.

One preferred method for the expansion of transfected T cells of the invention relies on the use of magnetic beads coated with the specific TCR ligand recognised by the introduced TCR, and a combination of anti CD28 and anti-CD3. Briefly, the use of these beads allows the selective expansion of T cells possessing functional transfected TCRs. The beads are commercially available in an anti-biotin coated form (Miltenyi Biotec, Bisley UK) which can then be coated with the biotinylated ligands of choice. (Protocol 9 herein details the required methodology)

Once the T cells have been prepared using the above methods they can be administered to patients together with a pharmaceutically acceptable carrier.

Administration of the Transfected Cells to the Patient

The invention provides a method of directing cells to a population of target cells in a patient, said method comprising administering to a patient a plurality of cells expressing a surface anchored TCR, wherein said TCR comprises a disulfide interchain bond between extracellular constant domain residues which is not present in native TCRs and wherein the TCR presented by such cells is specific for a TCR ligand on the population of target cells.

The invention also provides a method of directing a T cell response to a target cell phenotype in a patient, said method comprising administering to a patient a plurality of T cells expressing a surface anchored TCR, wherein said TCR comprises a disulfide interchain bond between extracellular constant domain residues which is not present in native TCRs and wherein the TCR presented by such T cells is specific for a TCR ligand on the target cell type.

In another embodiment of the invention the TCR ligand on the target cell type is a peptide-MHC complex or a CD1-antigen complex.

In a further embodiment of the invention the administered cells are not cytotoxic T cells.

In a further embodiment of the invention the target cell is a cancer cell or infected cell and the administered cells are cytotoxic T cells.

In a further embodiment of the invention the TCR ligand is unique to one tissue-type or to cells characteristic of one organ of the body.

In another embodiment of the invention the target cell is a target for auto-reactive T cells in autoimmune disease, organ rejection or Graft Versus Host Disease (GVHD). In a specific embodiment the target cells is an islet cell.

Examples of suitable MHC-peptide targets for the TCR according to the invention include, but are not limited to, viral epitopes such as HTLV-1 epitopes (e.g. the Tax peptide restricted by HLA-A2; HTLV-1 is associated with leukaemia), HIV epitopes, EBV epitopes, CMV epitopes; insulin and/or IGRP-derived diabetes epitopes; melanoma epitopes (e.g. MAGE-1 HLA-A1 restricted epitope) and other cancer-specific epitopes (e.g. the renal cell carcinoma associated antigen G250 restricted by HLA-A2). Further disease-associated pMHC targets, suitable for use in the present invention, are listed in the HLA Factsbook (Barclay (Ed) Academic Press), and many others are being identified.

In a further embodiment of the invention the population of T cells is isolated from a patient to be treated.

T cells expressing the transfected TCRs can be administered to the patients by a number of routes. For example, i.v. infusion at regular intervals, optionally accompanied by the administration of a cytokine such as IL-2.

A further embodiment of the invention provides an infusible or injectable pharmaceutical composition comprising a plurality of cells expressing a surface anchored TCR, said TCR comprises a disulfide bond between α and β extracellular constant domain residues which is not present in native TCRs together with a pharmaceutically acceptable carrier.

Such pharmaceutical compositions adapted for parenteral administration include aqueous and non-aqueous sterile injection formulations which may contain suspending agents, anti-oxidants, buffers, bacteriostats and solutes which render the formulation substantially isotonic with the blood of the intended recipient.

Dosages of the cells of the present invention can vary between wide limits, depending upon the disease or disorder to be treated, the age and condition of the individual to be treated, etc. and a physician will ultimately determine appropriate dosages to be used. For example, a effective dosage may vary between $10^5$ to $10^{10}$ cells/kg body weight. The practice of therapeutic administration by infusion is described in a number of papers. See, for example (Rosenberg 1988 New Eng. J Med 319 1676-1680). The dosage may be repeated as often as appropriate. If side effects develop the amount and/or frequency of the dosage can be reduced, in accordance with normal clinical practice.

Additional Aspects

The invention provides a method of treatment of cancer, GVHD, infection, organ rejection, or auto-immune disease comprising administering a plurality of cells presenting at least one αβ T cell receptor (TCR) anchored to the membrane by a transmembrane sequence, said TCR comprising a disulfide interchain bond between extracellular constant domain residues which is not present in native TCRs. A specific embodiment is provided wherein the auto-immune disease is a disease selected from Rheumatoid Arthritis, Diabetes, Multiple Sclerosis or Reactive Arthritis Another aspect of the invention is provided by the use of a cell presenting at least one αβ T cell receptor (TCR) anchored to the membrane by a transmembrane sequence, said TCR comprising a disulfide interchain bond between extracellular constant domain residues which is not present in native TCRs in the preparation of a medicament for treatment of cancer, GVHD, infection, organ rejection, or auto-immune disease.

Cancers which may benefit the methods of the present invention include: leukaemia, head, neck, lung, breast, colon, cervical, liver, pancreatic, ovarian and testicular.

Auto-immune diseases which may benefit the methods of the following invention include:
Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune Neutrogena
Autoimmune thrombocytopenic purpura
Behcet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis Preferred features of each aspect of the invention are as for each of the other aspects mutatis mutandis. The prior art documents mentioned herein are incorporated to the fullest extent permitted by law.

METHODS

Reference is made in the following to the accompanying drawings in which:

FIG. 1 illustrates the domains that comprise TCR α and β chains: wherein "S" denotes the signal peptide, "V" denotes the variable domain, "J" denotes the joining domain, D denotes the diversity domain, and "C" denotes the constant domain which contains the transmembrane sequence;

FIG. 2 illustrates the structure of a cell surface TCR containing a non-native interchain disulfide bond;

FIGS. 3a and 3b show respectively the nucleic acid sequences of the α (SEQ ID NO:34) and β (SEO ID NO:35) chains of a soluble A6 TCR, mutated so as to introduce a cysteine codon. The shading indicates the introduced cysteine codons;

FIG. 4a shows the amino acid sequence (SEQ ID NO:36) encoded by the DNA sequence of FIG. 3a, including the $T_{48} \rightarrow C$ mutation (underlined) used to produce the novel disulfide inter-chain bond, and FIG. 4b shows the amino acid sequence (SEQ ID NO:37) encoded by the DNA sequence of FIG. 3b, including the $S_{57} \rightarrow C$ mutation (underlined) used to produce the novel disulfide inter-chain bond;

FIG. 5 graphically illustrates the PCR reactions required to produce a DNA sequence encoding a full-length disulfide-linked A6 Tax TCR using DNA encoding soluble disulfide-linked A6 Tax TCR and wild-type A6 Tax TCR as templates;

FIG. 6a shows the nucleic acid (SEQ ID NO:38) and protein sequences (SEQ ID NO:39) of the membrane anchored α chain of A6 TCR, mutated so as to introduce a new cysteine codon and mutate the Cys involved in forming the native inter-chain disulfide bridge to Ser. The first shading indicates the introduced cysteine codon; the underlined Ser codon indicates the position of the Cys->Ser mutation disrupting the capacity to form the native inter-chain disulfide link.

FIG. 6b shows nucleic acid (SEQ ID NO:40) and protein (SEQ ID NO:41) sequences of the membrane anchored β chain of A6 TCR, using the native constant domain, TRBC2 (nomenclature according to the IMGT format as described in (LeFranc et al, (2001) The T cell receptor Factsbook, Academic Press), mutated so as to introduce a new cysteine codon and mutate the Cys involved in forming the native inter-chain disulfide bridge to Ser. The first shading indicates the introduced cysteine codon; the underlined Ser codon indicates the position of the Cys->Ser mutation disrupting the capacity to form the native inter-chain di-sulfide link.

FIGS. 7a-7h detail the DNA sequence of all known TCR α chain constant and variable domains.

FIGS. 8a-8j detail the DNA sequence of all known TCR β chain constant and variable domains.

FIGS. 9a and 9b show respectively the DNA sequences of the α (SEQ ID NO:146) and β (SEQ ID NO:147) chains of a soluble AH-1.23 TCR, mutated so as to introduce a novel cysteine codon (indicated by shading).

FIGS. 10a and 10b show respectively the AH-1.23 TCR α (SEQ ID NO:148) and β (SEQ ID NO:149) chain extracellular amino acid sequences produced from the DNA sequences of FIGS. 9a and 9b.

The following protocol describes the preparation of the DNA sequences of FIGS. 3a and 3b. This protocol is usable for the preparation of the coding sequences of any given αβ TCR including a non-native disulfide interchain bond.

Protocol 1—Design of Primers and Mutagenesis of A6 Tax TCR α and β Chains to Introduce the Cysteine Residues Required for the Formation of a Novel Inter-Chain Disulfide Bond For mutating A6 Tax serine 48 of exon 1 in TRAC*01 to cysteine, the following primers were designed (mutation shown in lower case):

```
5'-C ACA GAC AAA tgT GTG CTA GAC AT

5'-AT GTC TAG CAC Aca TTT GTC TGT G
```

For mutating A6 Tax serine 57 of exon 1 in TRBC1*01 or TRBC2*01 to cysteine, the following primers were designed (mutation shown in lower case):

```
5'-C AGT GGG GTC tGC ACA GAC CC

5'-GG GTC TGT GCa GAC CCC ACT G
```

PCR Mutagenesis:

Expression plasmids containing the genes for the A6 Tax TCR α or β chain were mutated using the α-chain primers or the β-chain primers respectively, as follows. 100 ng of plasmid was mixed with 5 μl 10 mM dNTP, 25 μl 10×Pfu-buffer (Stratagene), 10 units Pfu polymerase (Stratagene) and the final volume was adjusted to 240 μl with H$_2$O. 48 μl of this mix was supplemented with primers diluted to give a final concentration of 0.2 μM in 50 μl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 μl of the digested reaction was transformed into competent E. coli XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l K$_2$HPO$_4$, 100 mg/l Ampicillin). Plasmid DNA was purified on a Qiagen mini-prep column according to the manufacturer's instructions and the sequence was verified by automated sequencing. The respective mutated nucleic acid and amino acid sequences are shown in FIGS. 3a and 4a for the α chain and FIGS. 3b and 4b for the β chain.

The following protocol describes the extension of the DNA of FIGS. 3a and 3b to add sequences coding for the remainder of the constant domains of the A6 TCR. Again, this protocol is usable for the extension of the constant domain encoding sequences of a corresponding soluble variant of any given αβ TCR.

Protocol 2—Design of A6 Tax TCR α and β Chain Nucleic Acid Sequences Required to Produce a Cell Surface Membrane Anchored A6 Tax TCR Including Cysteine Residues Required for the Formation of a Novel Inter-Chain Disulfide Bond The constructs encoding the α and β chains of a soluble disulfide-linked A6 Tax TCR molecule prepared as described in protocol 1 are used, along with cDNA from human peripheral blood mononuclear cells (PBMCs), in the production of constructs encoding the α and β chains of a membrane anchored A6 Tax TCR including cysteine residues required for the formation of a novel inter-chain disulfide bond. (Refer to FIG. 5 for a diagrammatic representation of the method involved).

TCR α chain DNA corresponding to Fragment 1 (See FIG. 5a) is amplified from cDNA encoding wild-type TRAV 12-2 TCR by PCR using the following primer pair specific for the TRAV 12-2 TCR signal peptide (Fwd primer) and the TRAV 12-2 TCR variable domain (Rev primer):

```
5' Fwd α primer:
5' - ATG ATG AAA TCC TTG AGA GTTTT - 3'

5' Rev α primer:
5' - GTA AGT GCA GTT GAGAGAGG - 3'
```

TCR β chain DNA corresponding to Fragment 1 (See FIG. 5a) is amplified from cDNA encoding wild-type TRBV 6-5 TCR by PCR using the following primer pair specific for the TRBV 6-5 TCR signal peptide (Fwd primer) and the TRBV 6-5 TCR variable domain (Rev primer):

```
5' Fwd β primer:
5' - ATG AGC ATC GGC CTC CTG T - 3'

5' Rev β primer:
5' - TT CAT ATC CTGGGC ACA CTG - 3'
```

The above primers are designed to produce a PCR product that incorporates an overlap with the DNA encoding the variable region of the soluble disulfide-linked A6 Tax TCR produced in protocol 1.

TCR α chain DNA corresponding to Fragment 2 (See FIG. 5b) is amplified from cDNA from PBMC using the following primer pair specific for the 3' end of TRAC, this primer pair also introduces a Cys to Ser mutation disrupting the formation of the native inter-chain disulfide bond:

```
3' Fwd α primer:
5' - TC CCC AGC CCA GAA AGT TCC TCT GAT GTC AAG
CTG GTC GAG AAA AG - 3'

3' Rev α primer:
5' - TTA GCT GGA CCA CAG CCG CAG - 3'
```

TCR β chain DNA corresponding to Fragment 2 (See FIG. 5b) is amplified from cDNA from PBMC using the following primer pair specific for the 3' end of TRBC2, this primer pair also introduces a Cys to Ser mutation disrupting the formation of the native inter-chain disulfide bond:

```
3' Fwd β primer:
5' - CC GAG GCC TGG GGT AGA GCA GAC TCT GGC TTC
ACC TCG GAG TCT TAC C - 3'

3' Rev β primer:
5' - TTA GCC TCT GGA ATC CTT TCT C- 3'
```

These primers are designed to produce a PCR product that incorporates an overlap with the DNA encoding the constant region of the soluble disulfide-linked A6 Tax TCR produced in protocol 1.

Final PCRs are required to assemble the entire genes for the two TCR-chains. For the alpha chain fragments 1 and 2 are mixed with the plasmid coding for the soluble alpha-chain and the full length coding region is amplified using the 5' Fwd α primer and the 3' Rev α primer with suitable restriction site sequences added to the primers as flanking sequences to facilitate sub-cloning in the required vector (for example, the retroviral pLXSN vector, BD Clontech, UK). The fragment is sub-cloned into the expression vector and sequenced.

For the beta chain fragments 1 and 2 are mixed with the plasmid coding for the soluble beta-chain and the full length coding region is amplified using the 5' Fwd β primer and the 3' Rev β primer with suitable restriction site sequences added to the primer as flanking sequences to facilitate sub-cloning into the required vector (for example, the retroviral pLXSN vector, BD Clontech, UK). The fragment is sub-cloned into the expression vector and sequenced.

FIGS. 6a and 6b show the nucleic acid and protein sequences of the membrane anchored α and β chain of A6 TCR respectively, mutated so as to introduce a new cysteine codon and mutate the cysteine residues involved in forming the native inter-chain disulfide bridge to Ser.

The above PCR reactions are all carried out using the following methodology.

For a 100 μl reaction mix:
1. 18 MΩ quality H$_2$O to 100 μl.
2. 50 pmol Forward Primer
3. 50 pmol Reverse Primer
4. 2 μl 10 mM dNTP (10 mM each of dATP, dTTP, dCTP, dGTP).
5. 10 μl 10×Buffer (Pfu buffer for cloning purposes and Taq buffer for diagnostic PCR).
6. 5 units of enzyme (Pfu DNA Polymerase or Taq polymerase according to the particular application).

PCR program:
1. A denaturation step where the sample is heated to 94° for 10 minutes.
2. A number of cycles (20-40) including
   a denaturation step 1 minute @ 94°
   an annealing step 1 minute @ 45-60° (use the gradient block in PCR-1 if you need to establish the optimal annealing temperature).
   an elongation step 5-10 minutes @ 72-73°.
3. A final elongation step 10 minutes @ 72-73° to ensure that all products are full length
4. followed by a soak step at 4°.

The following protocol describes the preparation of the DNA sequences of FIGS. 9a and 9b. This protocol is usable for the preparation of the coding sequences of any given αβ TCR which includes a non-native disulfide interchain bond.
Protocol 3—Production of DNA Encoding a Soluble AH-1.23 TCR Comprising a Non-Native Disulfide Inter-Chain Bond Synthetic genes encoding the TCR α and TCR β chains of a soluble AH1.23 TCR can be manufactured to order. There are a number of companies which carry out this service such as GeneArt (Germany).

FIGS. 9a and 9b show respectively the DNA sequences of the α and β chains of a soluble AH-1.23 TCR, mutated so as to introduce a novel cysteine codon (indicated by shading).

FIGS. 10a and 10b show respectively the AH-1.23 TCR α (SEQ ID NO:148) and β (SEQ ID NO:149) chain extracellular amino acid sequences produced from the DNA sequences of FIGS. 9a and 9b.

The DNA sequences shown in FIGS. 9a and 9b can then be sub-cloned into the required vector containing the DNA sequences of FIGS. 3a and 3b respectively in such a way as to replace the DNA encoding the corresponding extracellular portions of the A6 TCR.

The following protocol describes a means of preparing DNA sequences encoding full-length TCRs containing a non-native disulfide interchain bond for use in the current invention. Preferably, said DNA sequences will comprise restriction enzyme recognition site to facilitate ligation of the sequences into the vector of choice. This protocol is usable for the production of any αβ or γδ TCR.
Protocol 4—Production of Nucleic Acids Encoding Alternative TCR α and β Chains of Membrane Anchored TCRs Including Cysteine Residues Required for the Formation of a Novel Inter-Chain Disulfide Bond.

To incorporate DNA encoding an alternative TCR into the vector(s) of choice synthetic genes encoding the required full-length TCR α and TCR β chains, altered in order to encode the required introduced cysteine residues in the constant domains thereof, can be manufactured to order. There are a number of companies which carry out this service such as GeneArt (Germany). Such DNA sequences can be produced which incorporate restriction enzyme recognition sequences to facilitate ligation of the DNA produced into the vector of choice.

For transfection of the desired cells with the expression vectors prepared according to protocol 6, selection of the appropriate vector is required:
Protocol 5—Vector Choice for the Transfection of T Cells with DNA Encoding TCRs Containing Cysteine Residues Required for the Formation of a Novel Inter-Chain Disulfide Bond.

As will be obvious to those skilled in the art the primary difference between transient and stable transfection methods is the choice of vector. The following table provides a summary of a number of vectors suitable for the transient transfection and/or stable transfection of T cells with DNA encoding TCRs containing cysteine residues required for the formation of a novel inter-chain disulfide bond:

| Vector and Supplier | Transient Expression | Random Stable Integration | Stable Site-Specific Integration | Stable Episomal Maintenance |
|---|---|---|---|---|
| pCI (Promega) | ✓ | ✓* | x | x |
| pCI$_{neo}$ (Promega) | ✓ | ✓* | x | x |
| pREP4 (Invitrogen) | ✓ | x | x | ✓ |
| pCEP4 (Invitrogen) | ✓ | x | x | ✓ |
| pcDNA5/FRT (Invitrogen) | ✓ | (✓) | ✓ | x |
| FRT Retroviral Vectors | ✓ | ✓ | ✓ | x |
| Standard Retroviral Vectors | ✓ | ✓ | x | x |

✓* - Suitable when in combination with an appropriate vector (e.g. pCI$_{neo}$ with pCI).
(✓) - Capable of random integration, but designed for site-specific integration into specialised recipient cells.

Ligation of the DNA sequences encoding a TCR containing a non-native disulfide interchain bond, prepared for example, as described in protocols 1 and 2, or protocols 3 or 4, into the desired vector or vectors is required. These vectors may be one of those listed in protocol 5. This protocol is usable for the ligation of the coding sequences of any given αβ or γδ TCR including a non-native disulfide interchain bond into the vector(s) of choice:
Protocol 6—Ligation of DNA Sequences Encoding a TCR Containing a Non-Native Disulfide Interchain Bond into the Desired Vector In order to facilitate the insertion of DNA encoding the TCR chains in the desired orientation into the vector or vectors of choice the vector(s) and DNA encoding the TCR chains should each have the same pair of different complementary ends. To achieve this the desired recipient vector or vectors, and the DNA sequences encoding the TCR chains are digested with the same appropriate pair of differing restriction enzymes. The cut DNA chains and the cut vector or vectors are then ligated using the Rapid DNA Ligation kit (Roche) following the manufacturers instructions.

Protocol 7 describes a general procedure for the isolation of T cell sub-populations for transformation to produce cells in accordance with the invention.
Protocol 7—Isolation of T cell Sub-Populations PBMCs are isolated from venous blood samples using Leucosep® tubes (Greiner Bio-one, Germany) following the manufacturer's instruction. The isolated PBMCs are washed and used immediately. Freshly isolated PBMCs are washed twice in 10% autologous human serum/RPMI (Gibco BRL). Finally, the cells are re-suspended in RPMI medium.

T cell sub-populations are isolated from PBMCs by FACS using the relevant combination of antibodies in the table below for the T cell sub-population required and the following procedure:

| Label Used | Cell Population isolated |
|---|---|
| Anti CD3 fluorescent label | All (cytotoxic and helper) T cells |
| Anti CD8 fluorescent label | CD8$^+$ (cyto-toxic) T cells |
| Anti CD4 fluorescent label | CD4$^+$ (helper) T cells |

| Label Used | Cell Population isolated |
| --- | --- |
| Anti CD4 and anti CD25 fluorescent label | Regulatory T cells |

Under sterile conditions, the relevant fluorescently-labeled antibodies (0.01 mg/ml final concentration) are incubated with PBMCs ($1 \times 10^7$/ml) for 30 mins at 37° C., 5% $CO_2$. Cells are then washed using medium (37° C.), centrifuged for 10 mins at 250×g and the supernatant discarded. The pellet is re-suspended and the cells are then bulk-sorted by FACS. The selected T cells are collected in either medium containing 10% autologous serum (for in-vitro culturing), or in the appropriate infusion medium, such as Hank's balanced buffer solution (Sigma, UK) with 10% autologous human serum albumin for immediate therapeutic use.

Alternatively, the required T cell sub-population may be isolated using magnetic beads coated with the same antibodies and antibody combinations described above. Minimacs beads, produced by Miltenyi Biotech, are suitable for use in the isolation of T sub-populations and the manufacturer provides instructions for their use. This method "positively" selects and isolates the desired T cell sub-population. It is also possible to "negatively" select the desired T cell sub-population. This is achieved by coating the beads with a range of antibodies that will bind to all but the required T cell population in PBMCs.

Protocol 8 describes one method, usable in accordance with the invention, of modifying isolated cells for expression of TCRs containing a non-native disulfide interchain bond.

Protocol 8—Retro-Viral Transduction of T Cell with TCRs Containing Introduced Cysteine Residues Capable of forming a Non-Native Disulfide Interchain Bond Primary T cells or T cell lines/clones are transduced with an appropriate retroviral vector, (e.g. the pLXSN retrovirus (BD ClonTech, UK)) following a T cell transduction methodology based on that described in (Clay (1999) *J. Immunol* 163 507-513 and Bunnel (1995) *PNAS USA* 92 7739)

Production of Retroviral Supernatant

Briefly, in order to produce retroviral supernatant, the PG13 retrovirus producer cell line is transduced with the retroviral vector (PLXSN, BD Clontech, UK) produced in protocol 2 that contains DNA encoding the α and β chains of a membrane anchored A6 Tax TCR including cysteine residues required for the formation of a novel inter-chain disulfide bond. High titre clones are then isolated using standard techniques familiar to those skilled in the art. (See, for example (Miller (1991) *J. Virol* 65 2220)

A high titre clone is then grown to 80% confluence and the supernatant is then harvested.

Transduction of T Cells with Retroviral Supernatant

T cells are then re-suspended at $1 \times 10^6$ cells/ml in microtitre well plates in retroviral supernatant containing 8 μg/ml polybrene and 600 IU/ml IL-2. The plates are then centrifuged at 1000×g for 90 mins and incubated overnight at 37° C. in a humidified 5% $CO_2$ incubator. This transduction procedure is repeated after 2 days. The transduction procedure described in (Clay (1999) *J. Immunol* 163 507-513) is then followed, thereby providing transfected T cells ready for in-vitro testing.

Protocol 9 describes a general method for enriching and enlarging a population of T cells in accordance with the invention. This method is not TCR specific.

Protocol 9—In-Vitro Growth of Transfected T Cells

After the transfection of T cells to express modified TCRs as described in Protocol 8 these T cells can, if necessary, be grown in-vitro to produce an enriched and enlarged populations of cells for in-vitro evaluation or therapeutic use using the following method.

Anti-biotin coated Clinimacs beads (Miltenyi Biotec, Germany) are coated with biotinylated anti-CD28 and anti-CD3 antibodies. 500,000 T cells and 500,000 autologous irradiated (33 Gy) APCs pulsed with the appropriate peptide (Tax peptide), are added to RPMI 1640 buffer containing 10-50 U/ml IL-2 and 10% autologous serum. $5 \times 10^6$/ml anti-CD28 and anti-CD3 antibody coated Clinibeads are then added to the cells.

The cells are then incubated under sterile conditions at 37° C., 5% CO2 for 7 days. During this incubation period the buffer is replaced every 3 days. The cells can be re-stimulated the following week with the same ratio of beads to T-cells and fresh peptide-pulsed APCs. Once the required total number of transfected T cells has been reached the T cells are then re-suspended in the appropriate buffer for in-vitro evaluation or therapeutic use.

Protocol 10 describes one method of testing for successful cell surface expression of the desired TCRs on the chosen modified cell. This method is generally applicable, and not restricted to any particular cell surface TCR.

Protocol 10—Fluorescence Activated Cell Sorting (FACS)—Based Assay to Demonstrate Specific Binding of Cognate Peptide—MHC Complexes to T Cells Transfected to Express an A6 Tax TCR Incorporating Cysteine Residues Required for the Formation of a Novel Inter-Chain Disulfide Bond Preparation of T Cell Samples for Staining The transfected T cells are re-suspended in FACS staining buffer (2% FCS/PBS, at 37° C.) and counted. The cells are aliquoted into FACS tubes and pre-incubated at 37° C. for 5-10 minutes prior to staining.

Staining of T Cells with HLA-A2 Tax Tetramers to Assess TCR-pMHC Binding

In order to stain the transfected T cells HLA-A2 Tax monomers are prepared using the methods described in WO 99/60120, and tetramerised using Phycoerythrin (PE)—labelled streptadivin via the methods described in (O'Callaghan (1999) *Anal Biochem* 266 9-15)

The following fluorescently labelled molecules are also used in the FACS assay as controls:

FITC-labelled isotype controls

PE-labelled "irrelevant" peptide-HLA-A2 tetramers

PE-labelled HLA-A2 Tax tetramer (48 μg) is incubated with $1 \times 10^6$ transfected T cells and 5 μg anti-CD8-FITC labelled antibody (or 5 μg anti-CD4-FITC labelled antibody) for 20 mins at 37° C. Cells are then washed using FACS buffer (37° C.), centrifuged for 10 mins at 250×g and the supernatant discarded.

After the wash, transfected T cells are re-suspended in 0.5 ml PBS. The T cell populations present in the samples are then analysed by flow cytometry.

Any T cells that are double-labelled by both the PE-HLA-A2 Tax tetramers and the αCD8-FITC labels (or anti-CD4-FITC labelled antibody) are $CD8^+$ T cells (or CD4+T cells) expressing the transfected A6 Tax TCR.

The above HLA tetramer FACs staining method can be adapted to assess the expression level of any exogenous TCR on the surface of T cells by using tetramers of the cognate peptide-HLA for the desired exogenous TCR.

Staining of Transfected T Cells with Antibodies to Assess Exogenous TCR Expression As will be obvious to those skilled in the art there are other binding agent that can be utilised in such FACS methods, or any other suitable detection methods, for the assessment of exogenous TCR. The following table provides a summary of some antibodies suitable for this purpose:

| Antibody Specificity | Usage |
| --- | --- |
| Specific TCR variable domain (e.g. anti-Vβ30) | Assessment of exogenous TCR expression on T cells posessing an endogenous TCR of differing V domain usage |
| Pan TCR | Assessment of exogenous TCR expression on TCR− cells |
| CD3 | Assessment of exogenous TCR expression on CD3− TCR− cells. The presence of the exogenous TCR should "rescue" cell surface CD3 presentation |

Protocol 11 describes one method of testing for successful cell surface expression of functional exogenous TCRs on the surface of a CTL. This method is specific for such CTL cells. However, the method is not limited to a specific TCR.

Protocol 11—Europium-Release Method for Assessing the Ability of CTL 'Killer' T Cells Transfected to Express the Membrane-Anchored A6 Tax TCR to Specifically Lyse Target Cells.

The following assay is used to assess the ability of CTLs transfected to express the membrane-anchored A6 Tax TCR to specifically lyse HLA-A*0201$^+$ target cells.

The following mixtures are prepared for the assays:

Experimental wells: 50 µl of Transfected CTLs, 50 µl of media, 50 µl targets cells pulsed with the cognate HLA-A2 peptide.

Negative control wells: 50 µl of Transfected CTLs (effector cells), 50 µl of media, 50 µl targets cells pulsed with an irrelevant HLA-A2 peptide.

Background wells: APC Target cells are spun down after dilution to final concentration and the 50 µl of supernatant added to 100 µl media.

Spontaneous release wells: Target cells alone (no effector cells)+100 µl media

Maximum release wells: spontaneous release wells+15 µl of 10% Triton (Sigma T-9284)

Briefly, the above mixtures of effector and target cells are incubated for 2 to 4 hours and the Europium release assay is then carried out following the instructions supplied with the Delfia EuTDA Cytotoxicity Kit (Perkin Elmer).

Protocol 12 describes one method of testing for successful cell surface expression of functional exogenous TCRs on the surface of regulatory T cells or CTLs. The method is not limited to a specific TCR.

Protocol 12—Thymidine Incorporation Assay for Assessing the Ability of T Cells Transfected to Express the Membrane-Anchored AH1.23 TCR to Specifically Alter T Cell Proliferation.

$5\times10^6$ PMBCs are pulsed with 1 µM of the cognate peptide for the AH1.23 TCR and then cultured in RPMI 1640 medium at 37° C., 5% $CO_2$ for 14 days. A control group of $5\times10^6$ PMBCs cultured at 37° C., 5% $CO_2$ for 14 days without peptide pulsing. Both cultures are fed with 40 units/ml recombinant human IL-2 every 3 days.

The following are then added to $1\times10^5$ cells in a 96 well plate both the cultures prepared above:

$1\times10^5$ fresh autologous irradiated (33 Gy) PBMCs, and a range (0 cells, $5\times10^4$, $1\times10^5$, $2\times10^5$, $5\times10^5$) of T cells transfected with the AH1.23 TCR using the methods described in the previous protocols. These cultures are then incubated in RPMI 1640 medium for 3 days at 37° C., 5% $CO_2$.

1.85 MBq/ml of $H^3$ Thymidine is then added to these cultures and they are incubated for a further 8 hours at 37° C., 5% $CO_2$. The cells are harvested using a cell-harvester, and the level of thymidine incorporation into the cells is measured using a TopCount scintillation counter.

A reduction in thymidine incorporation into the previously peptide-pulsed PBMCs, compared to that seen in the non-pulsed PMBCs indicates that the transfected Regulatory T cells are causing a pMHC-specific down-regulation of cell proliferation.

An increase in thymidine incorporation into the previously peptide-pulsed PBMCs, compared to that seen in the non-pulsed PMBCs indicates that the transfected CTLs are causing a pMHC-specific up-regulation of cell proliferation.

Protocol 13 describes the treatment of patients with cells in accordance with the invention. This treatment method can be used for T cells transfected with any exogenous TCR.

Protocol 13—Infusion into Patients of T Cells Transfected to Express TCRs Including Cysteine Residues Required for the Formation of a Novel Inter-Chain Disulfide Bond In order to infuse the transfected T cells expressing TCRs including cysteine residues required for the formation of a novel inter-chain disulfide bond into patients the following methodology, as described in (Haque (2002) Lancet 360 436-442), is used. Briefly, the transfected T cells are washed in Hank's balanced buffer solution (Sigma, UK) with 10% autologous human serium albumin and then re-suspended in 20 ml of the same buffer solution. The transfected T cells are then slowly infused into the patient requiring treatment at a dose of $10^6$ cells per kg bodyweight over a 15 minute period. The patient's vital signs are regularly checked over the next 4 hours to detect any toxic effects.

These infusions are then repeated periodically, and the condition of the patient assessed by the most appropriate method. For example, in the case of a patient receiving the transfected TCRs as a means of treating a tumour these could include one or more of the following palpation, radiography, CT scanning or biopsy. The dosage and frequency of the infusions is varied if required. Finally the outcome of the treatment at 6 months after the final infusion is also recorded in accordance with WHO criteria.

The invention claimed is:

1. A mammalian cell comprising a membrane presenting at least one modified T cell receptor (TCR) anchored to the membrane by a transmembrane sequence, wherein the modified TCR comprises an interchain disulfide bond between extracellular constant domain residues which is not present in native TCRs.

2. A mammalian cell comprising a membrane, presenting at least one modified αβ T cell receptor (TCR) anchored to the membrane by a transmembrane sequence, wherein the modified αβ TCR comprises a disulfide bond between α and β extracellular constant domain residues which is not present in native TCRs.

3. A cell as claimed in claim 1 wherein the modified TCR is an αβ heterodimeric TCR.

4. A cell as claimed in claim 3 wherein the modified TCR comprises α and β chains and wherein each chain comprises a transmembrane sequence, fused at its N terminus to an extracellular constant domain sequence, in turn fused at its N terminus to a variable region sequence.

5. A cell as claimed in claim 4 wherein at least sequences of the modified TCR α and β chains, other than complementarity determining regions of the variable region, correspond to human TCR α and β sequences.

6. A cell as claimed in claim 1 wherein the modified TCR is an αβ single chain TCR.

7. A cell as claimed in claim 6 wherein the modified TCR comprises:
   (i) a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequences, and a linker sequence linking the C terminus of the first segment to the N terminus of the second segment, or
   (ii) a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequences, and a linker sequence linking the C terminus of the first segment to the N terminus of the second segment.

8. A cell as claimed in claim 7 wherein at least the sequences of the modified TCR α and β chains, other than complementarity determining regions of the variable region, correspond to human TCR α and β sequences.

9. A cell as claimed in claim 1 displaying a plurality of modified TCRs.

10. A cell as claimed in claim 1 wherein the cell is a T cell.

11. A cell as claimed in claim 1 wherein the cell is a cytotoxic T cell.

12. A cell as claimed in claim 1 wherein the cell reduces cellular or proinflammatory arms of an auto-immune response.

13. A cell as claimed in claim 12 wherein the cell is a regulatory T cell.

14. A cell as claimed in claim 1 wherein in the modified TCR a covalent disulfide bond links a residue of an immunoglobulin region of a constant domain of the α chain to a residue of an immunoglobulin region of a constant domain of the β chain.

15. A cell as claimed in claim 1 wherein the modified TCR has no equivalent of the interchain disulfide bond present in native TCRs.

16. A cell as claimed in claim 15 wherein in the modified TCR the cysteine residues which form the interchain disulfide bond present in native TCRs are replaced by noncysteine residues.

17. A cell as claimed in claim 15, wherein in the modified TCR cysteine residues which form the interchain disulfide bond present in native TCRs are replaced by serine or alanine.

18. A cell as claimed in claim 1 wherein in the modified TCR, an unpaired cysteine residue present in native TCR β chains is not present.

19. A cell as claimed in claim 1 wherein in the modified TCR the disulfide bond is between cysteine residues substituted for residues whose β carbon atoms are less than 0.6 nm apart in the native TCR structure.

20. A cell as claimed in claim 1 wherein in the modified TCR the disulfide bond is between cysteine residues substituted for Thr 48 of exon 1 of TRAC*01 and Ser 57 of exon 1 of TRBC1*01 or TRBC2*01.

21. A cell as claimed in claim 1, wherein in the modified TCR the disulfide bond is between cysteine residues substituted for Thr 45 of exon 1 of TRAC*01 and Ser 77 of exon 1 of TRBC1*01 or TRBC2*01.

22. A cell as claimed in claim 1, wherein in the modified TCR the disulfide bond is between cysteine residues substituted for Tyr 10 of exon 1 of TRAC*01 and Ser 17 of exon 1 of TRBC1*01 or TRBC2*01.

23. A cell as claimed in claim 1, wherein in the modified TCR the disulfide bond is between cysteine residues substituted for Thr 45 of exon 1 of TRAC*01 and Asp 59 of exon 1 of TRBC1*01 or TRBC2*01.

24. A cell as claimed in claim 1, wherein in the modified TCR the disulfide bond is between cysteine residues substituted for Ser 15 of exon 1 of TRAC*01 and Glu 15 of exon 1 of TRBC1*01 or TRBC2*01.

25. An infusible or injectable pharmaceutical composition comprising a plurality of T cells as claimed in claim 1 together with a pharmaceutically acceptable carrier.

* * * * *

UNITED STATES PATENT AND TRADEMARK OFFICE
CERTIFICATE OF CORRECTION

| | |
|---|---|
| PATENT NO. | : 8,361,794 B2 |
| APPLICATION NO. | : 11/597252 |
| DATED | : January 29, 2013 |
| INVENTOR(S) | : Bent Karsten Jakobsen |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1695 days.

Signed and Sealed this
Twenty-fourth Day of March, 2015

Michelle K. Lee
*Director of the United States Patent and Trademark Office*